US006958222B2

(12) United States Patent
Koffas et al.

(10) Patent No.: US 6,958,222 B2
(45) Date of Patent: Oct. 25, 2005

(54) PRODUCTION OF FEED USING A DENITRIFYING METHANOTROPHIC BACTERIAL STRAIN

(75) Inventors: Mattheos Koffas, Wilmington, DE (US); James M. Odom, Kennett Square, PA (US); Andreas Schenzle, Zurich (CH)

(73) Assignee: E. I. du Pont de Nemours and Company, Wilmington, DE (US)

(*) Notice: Subject to any disclaimer, the term of this patent is extended or adjusted under 35 U.S.C. 154(b) by 17 days.

(21) Appl. No.: 10/701,200

(22) Filed: Nov. 4, 2003

(65) Prior Publication Data

US 2004/0147011 A1 Jul. 29, 2004

Related U.S. Application Data

(62) Division of application No. 09/934,868, filed on Aug. 22, 2001, now Pat. No. 6,689,601.

(60) Provisional application No. 60/229,858, filed on Sep. 1, 2000.

(51) Int. Cl.[7] ........................... C12P 1/00; C12P 21/04; C12N 9/12; A23L 1/28; A12L 1/00

(52) U.S. Cl. ........................ 435/41; 435/194; 435/71.2; 426/61; 426/7

(58) Field of Search ......................... 435/41, 194, 71.2; 426/61, 7

(56) References Cited

U.S. PATENT DOCUMENTS

| | | | |
|---|---|---|---|
| 4,348,476 | A | 9/1982 | Hou |
| 5,750,821 | A | 5/1998 | Inomata et al. |
| 2002/0110885 | A1 | 8/2002 | Koffas |

FOREIGN PATENT DOCUMENTS

| | | | |
|---|---|---|---|
| EP | 0220 951 | A2 | 5/1987 |
| WO | WO 90 12105 | A2 | 10/1990 |
| WO | WO 9633821 | A1 | 10/1996 |
| WO | WO 2000007718 | A1 | 2/2000 |

OTHER PUBLICATIONS

Ladror et al Cloning, sequencing, and expression of pyrophosphate–dependent phosphofructokinase from Propionibacterium freudenreichii. J Biol Chem. Sep. 5, 1991;266(25):16550–5.*

UniProt_03 Database Accession No. P29495 Apr. 1, 1993 from Ladror et al J Biol Chem. Sep. 5, 1991;266(25):16550–5. Alignment with SEQ ID No.: 6.*

Methane and Methanol Utilizers (Biotechnology Handbook 5, J. Colin Murrell and Howard Dalton eds. 1992, Pleanum Press NY, pp. 23–84.

Murrell et al., Molecular biology and regulation of methane monooxygenase, Arch. Microbiol. , 2000, 173(5–6), 325–332.

Grigoryan, E. A., Kinet Catal. , Catalytic Activation and Functionalization of Methane, 1999, 40(3), 350–363.

Sharpe, D. H. Bio Protein Manfacture, 1989, Ellis Horwood series in applied science and industrial technology, New York: Halstead Press.

Villadsen, J., Recent Trends Chem. React. Eng., (Proc. Int. Chem. React. Eng. Conf.), 2$^{nd}$ 1987, vol. 2, 320–333.

Editor(s) Kuikami, B. D.: Mashelkar, R. A.; Sharma, M. M. Publisher; Wiley East, New Delhi, India; Naguib, M., Proc. OAPEC Symp. Petroprotein (Pap), 1980, Meeting Date 1979, 253–77 Publisher: Organ. Arab Pet. Exporting Countries, Kuwait.

Tsien et al., Gas, Oil, Coal, Environ. Biotechnol. 2, Pap. Int. IGT Symp. Gas, Oil Coal, Environ. Biotechnol., 2$^{nd}$, 1990, 83–104. Editors Akin et al. , Publisher: Inst. Gas. Technol., Chicago, IL.

Merkley et al., Biorem. Recalcitrant Org., Pap. Int. In Situ On–Site Bioreclam. Symp., 3$^{rd}$, 1995, 165–74, Editors Hinchee et al., Publisher: Battelle Press, Columbus, OH.

Meyer et al., Development of techniques for the bioremediation of soil, air and groundwater polluted with chlorinated hydrocarbons: the demonstration project at the model site in Eppelheim, Microb. Releases, 1993, 2(1), 11–22.

Ivanova et al., Production of Organic Exometabolities by Diverse Cultures of Obligate Methanotrophs, Mikrobiologiya, 1988, 57(4), 600–5.

Kilbane, John J., Gas, Oil, Coal, Environ. Biotechnol. 3 (Pap. IGT's Int. Symp.), 3$^{rd}$ 1991, Meeting Date 1990, 207–28, Editors Akin et al., Publisher: IGT, Chicago, IL.

Urakami et al., Occurrence of Isoprenoid Compounds in Gramnegative Methanol–, Methane–, and Methylamine–Utilizing Bacteria, J. Gen. Appl. Microbiol. 1986, 32(4), 317–41.

Dijkhuizen, L. P. R. Levering, G. E. DeVries, 1992, In:Methane and Methanol Utilizers, Biotechnology Handbooks 5, J. Colin Murrell and Howard Dalton eds, 1992 Pleanum Press NY pp. 149–181.

(Continued)

*Primary Examiner*—Rebecca E. Prouty
*Assistant Examiner*—Sheridan L. Swope

(57) ABSTRACT

A high growth methanotrophic bacterial strain capable of growth on a C1 carbon substrate has been isolated and characterized. The strain has the unique ability to utilize both methane and methanol as a sole carbon source and has been demonstrated to possess a functional Embden-Meyerhof carbon flux pathway. The possession of this pathway conveys an energetic advantage to the strain, making it particularly suitable as a production platform for the production of biomass from a C1 carbon source.

1 Claim, 6 Drawing Sheets

OTHER PUBLICATIONS

Beschastnyl et al., Inst. Biochem. Physiol. Microor., Pushchino, Russia, Biokhimiya (Moscow) 1992, 57(8), pp. 1215–1221.

Shishkina et al., Inst. Bikhim. Fiziol. Mikroorg., Pushchino, Russia, Mikrobiologiya, 1990, 59(4), 533–8.

Trotsenko et al., Studies on Phosphate metabolism in obligate methanotrophs, Fems Microbiology Reviews 87, 1990, pp. 267–272.

Shishkina et al., Effect of Glucose on the Growth and Metabolism of Obligate Methanotrophs, vol. 57, No. 6, 1988, ppl. 917–923.

Alexandra et al., "Characterization and Phylogency of the *PFP* Gene of Amycolatopsis Methanolice Encoding PPI–Dependent Phosphofructokinase" Journal of Bacteriology, Washington, D.C. vol. 178, No. 1, Jan. 1996, pp. 149–155, XP002935145.

* cited by examiner

PRODUCTION OF FEED USING A DENITRIFYING METHANOTROPHIC BACTERIAL STRAIN

This application is a divisional of U.S. application Ser. No. 09/934,868, filed Aug. 22, 2001, which issued as U.S. Pat. No. 6,689,601 on Jan. 22, 2004, which claims the benefit of U.S. Provisional Application No. 60/229,858, filed Sep. 1, 2000.

FIELD OF THE INVENTION

The invention relates to the field of microbiology. More specifically, the invention relates to the use of a novel methanotrophic bacterial strain capable of utilizing a central carbon pathway for more efficient production of commercially useful products.

BACKGROUND OF THE INVENTION

Methanotrophic bacteria are defined by their ability to use methane as their sole source of carbon and energy. Although methanol is an obligate intermediate in the oxidation of methane, the ability to grow on methanol alone is highly variable among the obligate methanotrophs due to its toxicity (Green, Peter. Taxonomy of Methylotrophic Bacteria. In: Methane and Methanol Utilizers (Biotechnology Handbooks 5) J. Colin Murrell and Howard Dalton eds. 1992 Pleanum Press NY, pp. 23–84). Methane monooxygenase is the enzyme required for the primary step in methane activation and the product of this reaction is methanol (Murrell et al., *Arch. Microbiol.* (2000), 173(5–6), 325–332). This reaction occurs at ambient temperatures and pressures, whereas chemical transformation of methane to methanol requires temperatures of hundreds of degrees and high pressure (Grigoryan, E. A., *Kinet. Catal.* (1999), 40(3), 350–363; WO 2000007718; U.S. Pat. No. 5,750,821). It is this ability to transform methane under ambient conditions along with the abundance of methane that makes the biotransformation of methane a potentially unique and valuable process.

The commercial applications of biotransformation of methane have historically fallen broadly into three categories: 1) Production of single cell protein, (Sharpe D. H. BioProtein Manufacture (1989). Ellis Horwood series in applied science and industrial technology. New York: Halstead Press) (Villadsen, John, *Recent Trends Chem. React. Eng.*, [Proc. Int. Chem. React. Eng. Conf.], 2nd (1987), Volume 2, 320–33. Editor(s): Kulkarni, B. D.; Mashelkar, R. A.; Sharma, M. M. Publisher: Wiley East., New Delhi, India; Naguib, M., Proc. OAPEC Symp. Petroprotein, [Pap.] (1980), Meeting Date 1979, 253–77 Publisher: Organ. Arab Pet. Exporting Countries, Kuwait, Kuwait); 2) epoxidation of alkenes for production of chemicals (U.S. Pat. No. 4,348,476); and 3) biodegradation of chlorinated pollutants (Tsien et al., *Gas, Oil, Coal, Environ. Biotechnol.* 2, [Pap. Int. IGT Symp. *Gas, Oil, Coal, Environ. Biotechnol.*], 2nd (1990), 83–104. Editor(s): Akin, Cavit; Smith, Jared. Publisher: Inst. Gas Technol., Chicago, Ill.; WO 9,633,821; Merkley et al., *Biorem. Recalcitrant Org.*, [Pap. Int. In Situ On-Site Bioreclam. Symp.], 3rd (1995), 165–74. Editor(s): Hinchee, Robert E; Anderson, Daniel B.; Hoeppel, Ronald E. Publisher: Battelle Press, Columbus, Ohio.: Meyer et al., *Microb. Releases* (1993), 2(1), 11–22). Only epoxidation of alkenes has experienced little commercial success due to low product yields, toxicity of products and the large amount of cell mass required to generate products.

Large-scale protein production from methane, termed single cell protein or SCP has been technically feasible and commercialized at large scale (Villadsen supra). However, SCP has been less than economically successful due to the relatively high cost to produce microbial protein compared to agriculturally derived protein (i.e. soy protein). Single cell protein is a relatively low value product and therefore economic production cannot tolerate heavy bioprocessing costs. For this reason the yield of the methanotrophic strain may be critical to the overall economic viability of the process. Microbial biomass produced by methanotrophic bacteria is typically very high in protein content (~70–80% by weight), which can restrict the direct use of this protein to certain types of animal feed.

The conversion of C1 compounds to complex molecules with C—C bonds is a difficult and capital intensive process by traditional chemical synthetic routes. Traditionally, methane is first converted to synthesis gas (mixtures of hydrogen, carbon monoxide and carbon dioxide), which is then used to produce other small molecular weight industrial precursors. Typically these are “commodity” type chemicals such as acetate, formaldehyde, or methanol. The basic problem is activation of the methane molecule which is thermodynamically very difficult to achieve by chemical means. “Activation” refers to the process of making the chemically unreactive methane molecule more reactive.

Methanotrophic bacteria contain enzymes (methane monooxygenases) which are capable of methane activation at ambient temperatures and pressures. Methane activation consists of oxygen insertion into methane to form methanol which is much more readily metabolized to more complex molecules within the cell. Two types of methane monooxygenase are found in methanotrophic bacteria. A particulate methane monooxygenase (pMMO) has a narrow substrate specificity and is incapable of oxygen insertion into more complex molecules. Some, but not all methanotrophs may also contain a soluble methane monooxygenase (sMMO). This enzyme has been the subject of much investigation and proprietary claims due to its ability to oxygenate, or functionalize, a wide variety of aliphatic and aromatic molecules. This characteristic has been utilized for co-metabolic production processes where methanotrophs are fed both methane and a more complex molecule to be transformed by the sMMO. Numerous examples are reported of processes requiring both methane and, typically, a petroleum-derived feedstock such as toluene, naphthalene, or decane, where sMMO plays a role. However, the art is silent with respect to using methanotrophs for net synthesis of chemicals from methane as opposed to these co-metabolic transformations. For net synthesis, only inexpensive methane is required along with the ability to genetically engineer the strain to produce the desired chemical.

Methanotrophic cells can further build the oxidation products of methane (i.e. methanol and formaldehyde) into more complex molecules such as protein, carbohydrate and lipids. For example, under certain conditions methanotrophs are known to produce exopolysaccharides (Ivanova et al., *Mikrobiologiya* (1988), 57(4), 600–5; Kilbane, John J., II Gas, *Oil, Coal, Environ. Biotechnol.* 3, [Pap. IGT's Int. Symp.], 3rd (1991), Meeting Date 1990, 207–26. Editor(s): Akin, Cavit; Smith, Jared. Publisher: IGT, Chicago, Ill.). Similarly, methanotrophs are known to accumulate both isoprenoid compounds and carotenoid pigments of various carbon lengths (Urakami et al., *J. Gen. Appl. Microbiol.* (1986), 32(4), 317–41). Although these compounds have been identified in methanotrophs, they have not been microbial platforms of choice for production as these organisms have very poorly developed genetic systems, thereby limiting metabolic engineering for chemicals.

A necessary prerequisite to metabolic engineering of methanotrophs is a full understanding, and optimization, of the carbon metabolism for maximum growth and/or product yield. Obligate methanotrophs are typically thought to channel carbon from methane to useful products and energy via the Entner-Douderoff Pathway which utilizes the keto-deoxy phosphogluconate aldolase enzyme (Dijkhuizen, L., P. R. Levering, G. E. DeVries 1992. In: Methane and Methanol Utilizers (Biotechnology Handbooks 5) J. Colin Murrell and Howard Dalton eds. 1992 Pleanum Press NY pp 149–181). This pathway is not energy-yielding as is the case for the Embden-Meyerhof pathway. Thus, utilization of the Entner-Douderoff pathway results in lower cellular production yields and a greater proportion of the carbon produced as carbon dioxide compared to organisms that use the Embden-Meyerhof pathway. Therefore, a more energy efficient carbon processing pathway would greatly enhance the commercial viability of a methanotrophic platform for the generation of materials.

As noted above, methanotrophic bacteria possess the potential to be commercially effective production platforms for materials such as single cell protein, exopolysaccharides, and long chain carbon molecules such as isoprenoids and carotenoid pigments. The usefulness of methanotrophs for production of a larger range of chemicals is constrained however, by several limitations including, relatively slow growth rates of methanotrophs, limited ability to tolerate methanol as an alternative substrate to methane, difficulty in genetic engineering, poor understanding of the roles of multiple carbon assimilation pathways present in methanotrophs, and potentially high costs due to the oxygen demand of fully saturated substrates such as methane. The problem to be solved therefore is to develop a fast-growing, high yielding methanotroph capable of receiving foreign genes via standard genetic procedures. Full and rapid resolution of central carbon pathways is essential for enabling pathway engineering and carbon flux management for new products.

Applicants have solved the stated problem by providing a methanotrophic bacterial strain capable of efficiently using either methanol or methane as a carbon substrate. The strain is also metabolically versatile in that it contains multiple pathways for the incorporation of carbon from formaldehyde into 3-C units. The discovery of a phosphofructokinase and fructose 1,6bisphosphate aldolase in this strain suggests that it can utilize the more energetically favorable Embden-Meyerhof pathway in addition to the Entner-Douderoff pathways. The present strain is shown to be useful for the production of a variety of materials beyond single cell protein to include carbohydrates, pigments, terpenoid compounds and aromatic compounds. The formation of large amounts of carbohydrates from methane or methanol can be carried out by this strain. This is surprising and also enables this strain to be used for the production of typical carbohydrate or sugar fermentation end-products such as alcohols, acids and ketones. The present strain was also shown to be capable of genetic exchange with donor species such as *Escherichia coli* via a standard genetic procedure known as bacterial conjugation. In this way, the strain can be engineered for net synthesis from methane to produce new classes of products other than those naturally produced.

SUMMARY OF THE INVENTION

The present invention provides a methanotrophic bacterial strain capable of growth on a C1 carbon substrate. The instant bacterial strain may be further characterized by the ability to grow rapidly and efficiently on either methanol or methane as a sole carbon source. This efficiency is due to the presence of a pyrophosphate linked phosphofructokinase enzyme within an operative Embden-Meyerhof pathway. This is a novel observation for methanotrophic bacteria. Functionally, the utilization of the Emben-Meyerhof pathway and pyrophosphate, instead of the Entner-Douderoff pathway reaction results in highly favorable cellular energetics which is manifested in higher yields, carbon conversion efficiency and growth rate.

The present strain also contains an enzyme system capable of reducing nitrate or nitrite with formation of gaseous nitrogen oxides. This capability is useful for reducing oxygen demand as well as for removing nitrates and nitrites in methane-containing environments such as landfills, wastewater treatment systems or anywhere that methane, oxygen and nitrates are present.

The ability to form large amounts of carbohydrates in the form of starch, polyglucose and/or extracellular polysaccharide is also useful for the production of carbohydrate-based products. Additionally *Methylomonas* 16a is only capable of growth on methane or methanol and is incapable of proliferating in the human body and thus is completely harmless and non-pathogenic. These characteristics make the strain ideally useful for the production of a wide range of products including animal feeds comprising variable carbohydrate/protein ratios.

The strain is shown to be capable of genetic exchange and expression of foreign genes. Additionally the present strain may be identified by the characteristic 16sRNA sequence as set forth in SEQ ID NO:81.

Additionally the present invention provides methods for the production of single cell protein, carbohydrates, and carotenoid pigments, or higher value mixtures of protein, pigments and carbohydrates. Additionally the strain may be used as a denitrifying agent for the conversion of nitrate or nitrite to nitrous oxide with methane or methanol as carbon source.

Accordingly the invention provides a high growth methanotrophic bacterial strain which:

(a) grows on a C1 carbon substrate selected from the group consisting of methane and methanol; and (b) comprises a functional Embden-Meyerhof carbon pathway, said pathway comprising a gene encoding a pyrophosphate dependent phosphofructokinase enzyme, the gene selected from the group consisting of:

(a) an isolated nucleic acid molecule encoding the amino acid sequence as set forth in SEQ ID NO:6;

(b) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS;

(c) an isolated nucleic acid molecule comprising a first nucleotide sequence encoding a polypeptide of at least 437 amino acids that has at least 63% identity based on the Smith-Waterman method of alignment when compared to a polypeptide having the sequence as set forth in SEQ ID NO:6; and (d) an isolated nucleic acid molecule that is complementary to (a), (b) or (c).

Optionally the present strain may comprise at least one gene encoding a fructose bisphosphate aldolase enzyme as part of the functional Embden-Meyerhof carbon pathway. Additionally, the present strain may optionally contain a functional Entner-Douderoff carbon pathway, where the Entner-Douderoff carbon pathway comprises at least one gene encoding a keto-deoxy phosphogluconate aldolase.

In one embodiment the present strain may optionally contain other carbon flux genes encoding polypeptides selected from the group consisting of SEQ ID NO:2, 4, 6, 8, 10, 12, 14, 16, 18 and 20.

In another embodiment the present strain may possess a denitrification pathway where the pathway may optionally comprise genes encoding polypeptides having the amino acid sequences selected from the group consisting of SEQ ID NO:40, 42, 44, 46, 48, 50, 52, 54, 56, 58 and 60.

In another embodiment the present strain may contain a set of exopolysaccharide synthesizing enzymes where the exopolysaccharide synthesizing enzymes may have the amino acid sequences selected from the group consisting of SEQ ID NO:22, 24, 26, 28, 30, 32, 34, 36, and 38.

In a more specific embodiment the present strain may comprise genes encoding isoprenoid synthesizing enzymes where the enzymes are selected from the group consisting of SEQ ID NO:62, 64, 66, 68, 70, 72, 74, 86, and 78.

In a preferred embodiment the invention provides a method for the production of single cell protein comprising:

a) contacting the present high growth methanotrophic bacterial strain with a C1 carbon substrate, selected from the group consisting of methane and methanol, in a suitable medium for a time sufficient to permit the expression and accumulation of single cell protein; and b) optionally recovering the single cell protein.

It is an additional object of the invention to provide a method for the biotransformation of a nitrogen containing compound selected from the group consisting of ammonia, nitrate, nitrite, and dinitrogen comprising, contacting the present high growth methanotrophic bacterial strain with a C1 carbon substrate selected from the group consisting of methane or methanol, in the presence of the nitrogen containing compound, in a suitable medium for a time sufficient to permit the biotransformation of the nitrogen containing compound.

Similarly it is an object of the present invention to provide a method for the production of a feed product comprising protein, carbohydrates and pigment comprising the steps of:

a) contacting the high growth methanotrophic bacterial strain of the present invention with a C1 carbon substrate in a suitable medium for a time sufficient to permit the expression and accumulation of the feed product; and b) optionally recovering the feed product.

Optionally the relative compositions of protein, carbohydrate and pigment are altered through the up-regulation or down-regulation of any one of the genes encoding the proteins selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, and 69.

In a preferred embodiment the invention provides a method of identifying a high growth methanotrophic bacterial strain comprising:

(a) growing a sample suspected of containing a high growth methanotrophic bacterial strain on a suitable growth medium in the presence of methane as a sole carbon source;

(b) identifying colonies that grow under the conditions of step (a);

(c) analyzing the colonies identified in step (b) for the presence of pyrophosphate dependent phosphofructokinase activity.

BRIEF DESCRIPTION OF THE DRAWINGS SEQUENCE DESCRIPTIONS AND BIOLOGICAL DEPOSITS

Figure 1:
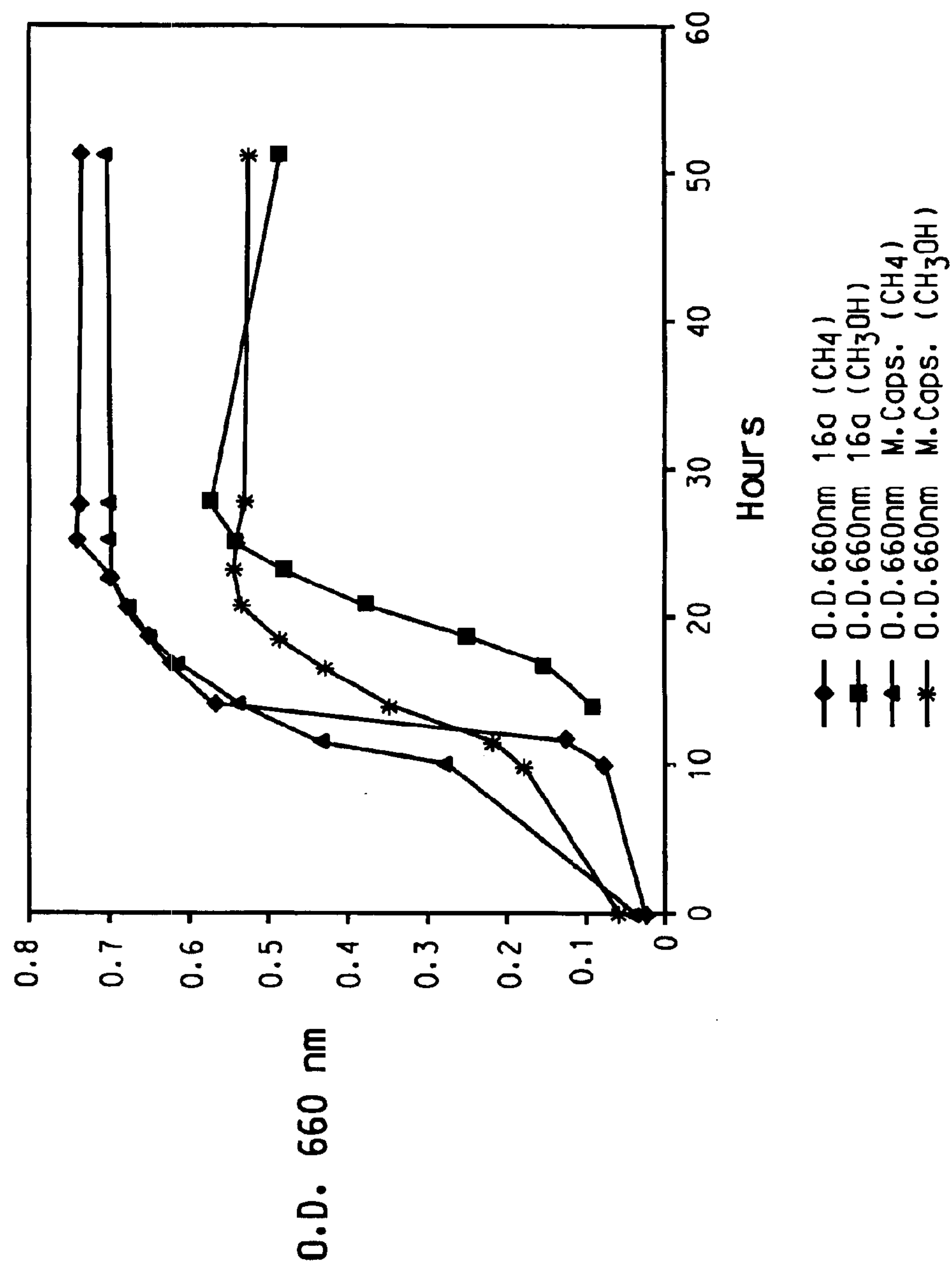
FIG. 1 shows the growth of *Methylomonas* 16a compared to the growth of *Methylococcus capsulatus* under identical growth conditions.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

| Description | SEQ ID Nucleic acid | SEQ ID Peptide |
|---|---|---|
| Phosphoglucomutase: carbon Flux | 1 | 2 |
| Glucose 6 phosphate isomerase: Carbon flux | 3 | 4 |
| Phosphofructokinase pyrophosphate dependent: Carbon Flux | 5 | 6 |
| 6-Phosphogluconate dehydratase: Carbon flux | 7 | 8 |
| Glucose 6 phosphate 1 dehydrogenase: Carbon Flux | 9 | 10 |
| Transaldolase: Carbon Flux | 11 | 12 |
| Transaldolase: Carbon Flux | 13 | 14 |
| Fructose bisphosphate aldoslase: Carbon Flux | 15 | 16 |
| Fructose bisphosphate aldoslase: Carbon Flux | 17 | 18 |
| KHG/KDPG Aldolase: Carbon Flux | 19 | 20 |
| ugp: Exopolysaccharaide | 21 | 22 |
| gumD: Exopolysaccharaide | 23 | 24 |
| wza: Exopolysaccharaide | 25 | 26 |
| epsB: Exopolysaccharaide | 27 | 28 |
| epsM: Exopolysaccharaide | 30 | 20 |
| waaE: Exopolysaccharaide | 31 | 32 |
| epsV: Exopolysaccharaide | 33 | 34 |
| gumH: Exopolysaccharaide | 35 | 36 |
| glycosyl transferase: Exopolysaccharaide | 37 | 38 |
| nirF: Denitrification | 39 | 40 |
| nirD: Denitrification | 41 | 42 |
| nirL: Denitrification | 43 | 44 |
| nirG: Denitrification | 45 | 46 |
| nirH: Denitrification | 47 | 48 |
| nirJ: Denitrification | 49 | 50 |

-continued

| Description | SEQ ID Nucleic acid | SEQ ID Peptide |
|---|---|---|
| nasA: Denitrification | 51 | 52 |
| norC: Denitrification | 53 | 54 |
| norB: Denitrification | 55 | 56 |
| norZ: Denitrification | 57 | 58 |
| norS: Denitrification | 59 | 60 |
| dxs: Terpenoid synthesis | 61 | 62 |
| dxr: Terpenoid synthesis | 63 | 64 |
| ispF: Terpenoid synthesis | 65 | 66 |
| ispD: Terpenoid synthesis | 67 | 68 |
| pyrG: Terpenoid synthesis | 69 | 70 |
| IspA: Terpenoid synthesis | 71 | 72 |
| IspE: Terpenoid synthesis | 73 | 74 |
| crtN: Terpenoid synthesis | 75 | 76 |
| crtN1: Terpenoid synthesis | 77 | 78 |
| Particulate monooxygenase | 79 | 80 |
| 16sRNA for Methylomonas 16a | 81 | — |

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
|---|---|---|
| Methylomonas 16a | ATCC PTA 2402 | Aug. 22, 2000 |

DETAILED DESCRIPTION OF THE INVENTION

The present invention describes the isolation and characterization of a high growth methanotrophic bacterial strain useful for the production of biomass including proteins, carbohydrates and pigments. The present strain is typed by 16sRNA as a *Methylomonas* sp. and is referred to herein as *Methylomonas* 16a. In addition, the strain may be useful for the production of mixtures of proteins, carbohydrates and pigments for the purpose of generating animal feeds. The strain possesses the advantage of an active Embden-Meyerhof carbon flux pathway having a pyrophosphate dependent phosphofructokinase gene, which conveys certain energetic advantages to the strain as a production platform for various materials and biomass. Additionally the strain naturally possesses an active isoprenoid pathway for the generation of pigments indigenous to the strain. In this disclosure, a number of terms and abbreviations are used. The following definitions are provided.

The term "Embden-Meyerhof pathway" refers to the series of biochemical reactions for conversion of hexoses such as glucose and fructose to important cellular 3 carbon intermediates such as glyceraldehyde-3-phosphate, dihydroxyacetone phosphate, phosphophenol pyruvate and pyruvate. These reactions typically proceed with net yield of biochemically useful energy in the form of ATP. The key enzymes unique to the Embden-Meyerhof pathway are phosphofructokinase and fructose-1,6bisphosphate aldolase.

The term "Entner-Douderoff pathway" refers to a series of biochemical reactions for conversion of hexoses such as glucose or fructose to important 3 carbon cellular intermediates such as pyruvate and glyceraldehyde-3-phosphate without any net production of biochemically useful energy. The key enzymes unique to the Entner-Douderoff pathway are the 6 phosphogluconate dehydratase and the ketodeoxyphosphogluconate aldolase.

The term "diagnostic" as it relates to the presence of a gene in a pathway means where a gene having that activity is identified, it is evidence of the presence of that pathway. Within the context of the present invention the presence of a gene encoding a pyrophosphate dependant phosphofructokinase is "diagnostic" for the presence of the Embden-Meyerhof carbon pathway and the presence of gene encoding a ketodeoxyphosphogluconate aldolase is "diagnostic" for the presence of the Entner-Douderoff carbon pathway.

The term "Yield" is defined herein as the amount of cell mass produced per gram of carbon substrate metabolized.

The term "carbon conversion efficiency" is a measure of how much carbon is assimilated into cell mass and is calculated assuming a biomass composition of $CH_2O_{0.5}N_{0.25}$.

The term "high growth methanotrophic bacterial strain" refers to a bacterium capable of growth with methane or methanol as a sole carbon and energy source and which possesses a functional Embden-Meyerhof carbon flux pathway resulting in a yield of cell mass per gram of C1 substrate metabolized. The specific "high growth methanotrophic bacterial strain" described herein is referred to as "*Methylomonas* 16a" or "16a", which terms are used interchangeably.

The term "a C1 carbon substrate" refers to any carbon-containing molecule that lacks a carbon-carbon bond. Examples are methane, methanol, formaldehyde, formic acid, methylated amines, and methylated thiols.

The term "functional denitrifying enzymatic pathway" refers to a series of enzymes which sequentially reduce nitrate or nitrite to more reduced products such as nitric oxide, nitrous oxide or ultimately dinitrogen. This process may or may not be energy yielding.

The term "denitrification" refers to the process of converting nitrates or nitrites to gaseous dinitrogen or other gaseous nitrogen oxides. To facilitate denitrification the present strain comprises genes encoding a number of enzymes in the denitrification pathway including: the nir genes (nirD, nirF, nirG, nirH, nirJ, nirL and nirS) encoding the nitrite reductase which catalyzes the reduction of nitrite ($NO_2$) to nitric oxide, the nasA gene, encoding nitrate reductase which catalyzes the reduction of nitrate ($NO_3$) to nitrite ($NO_2$); and the nor genes (norB, norC or norZ) encoding a nitric oxide reductase which catalyzes the reduction of nitric oxide (NO) to nitrous oxide ($N_2O$).

The term "isoprenoid compound" refers to any compound which is derived via the pathway beginning with isopentenyl pyrophosphate and formed by the head to tail condensation of isoprene units which may be of 5, 10, 15, 20, 30 or 40 carbons in length. The term "isoprenoid pigment" refers to a class of compounds which typically have strong light absorbing properties and are derived from the head to tail condensation of 5, 10, 15, 20, 25, 30 or 40 carbon isoprene chains. These isoprene chains are ultimately derived from isopentenyl pyrophosphate. A number of genes and gene products are associated with the present strain encoding the isoprenoid biosynthetic pathway including the dxs gene, encoding 1-deoxyxylulose-5-phosphate synthase, the dxr gene, encoding 1-deoxyxylulose-5-phosphate reductoisomerase, the "ispD," gene encoding the 2C-methyl-D-erythritol cytidyltransferase enzyme, the "ispE"gene encoding the 4-diphosphocytidyl-2-C-methylerythritol kinase, the "ispF" gene encoding a 2C-methyl-d-erythritol 2,4-cyclodiphosphate synthase, the "pyrG" gene, encoding a CTP synthase, the "ispA" gene, encoding geranyltransferase or farneseyl diphosphate synthase and the "ctrN" and "ctrN 1" genes, encoding diapophytoene dehydrogenase.

The term "single cell protein" will be abbreviated "SCP" and refers to a protein derived from organisms that exist in the unicellular, or single cell, state. This includes unicellular bacteria, yeasts, fungi or eukaryotic single cell organisms such as algae.

The term "extracellular polysaccharide" or "exocellular polysaccharide" will be abbreviated "ESP" and refers to a polysaccharide produced by methanotrophic bacteria typically comprising a carbohydrate "backbone" polymer as cross-linking carbohydrate polymers. These polymers are excreted on the outside of the microbial cell and may function in adhesion to surfaces or as a response to environmental stress. The present strain comprises a number of genes encoding various steps in the synthesis of extracellular polysaccharide including the "ugp" gene encoding UDP-glucose pyrophosphorylase, the "gumD" and "WaaE" genes encoding glycosyltransferases, the "wza" and "epsB" genes, encoding polysaccharide export proteins, the "epsM" gene, encoding a polysaccharide biosynthesis related protein, and the "epsV"gene, encoding a sugar transferase.

The term "carbohydrate" refers to any sugar containing constituent, particularly storage forms, such as glycogen or starch and extracellular polysaccharides.

The term "fermentation product" refers to products derived from the fermentation of any carbohydrate formed by the methanotrophic bacterium from methane or methanol.

The term "particulate methane monooxygenase" will be abbreviated as "pMMO" and will refer to a membrane-associated methane monooxygenase which inserts oxygen in to the enzyme substrate.

The terms "soluble methane monooxygenase" will be abbreviated as "sMMO" and will refer a to soluble or cytoplasmic methane monooxygenase—localized in the cytoplasm.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data. Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional preferred set of stringent conditions include 0.1×SSC, 0.1% SDS, 65° C. and washed with 2×SSC, 0.1% SDS followed by 0.1×SSC, 0.1% SDS).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987).

The present invention provides a unique methanotrophic bacterial strain, useful for the production of a variety materials from C1 carbon sources such as methane and methanol. The strain is referred to herein as *Methylomonas* 16a, and is characterized by rapid doubling time, high yield and the presence of genes encoding both the Entner-Douderoff carbon pathway as well as the Embden-Meyerhof pathway, allowing for versatility in carbon flux management and higher efficiency of carbon incorporation. The strain has been shown to produce a variety of food and feed products such as single cell protein, exopolysaccharide and starch. The strain has particularly high value in the production of food and feed materials as it is possible to manipulate the various concentrations of protein, carbohydrate and starch all within the same organism. This capability will permit strains to be uniquely tailored for individual specific food and feed applications. Additionally the strain has demonstrated utility in the production of terpenoid and carotenoid compounds, useful as pigments and as monomers in polymeric materials.

Isolation of *Methylomonas* 16a

The original environmental sample containing *Methylomonas* 16a was obtained from pond sediment. The pond sediment was inoculated directly into a defined mineral medium under 25% methane in air. Methane was used as the sole source of carbon and energy. Growth was followed until the optical density at 660 nm was stable, whereupon the culture was transferred to fresh medium such that a 1:100 dilution was achieved. After 3 successive transfers with methane as the sole carbon and energy source the culture was plated onto defined minimal medium agar and incubated under 25% methane in air. Many methanotrophic bacterial species were isolated in this manner. However, *Methylomonas* 16a was selected as the organism to study due to the rapid growth of colonies, large colony size, its ability to grow on minimal media, and pink pigmentation indicative of an active biosynthetic pathway for carotenoids.

Methanotrophs are classified into three metabolic groups ("Type I", "Type X" or "Type II") based on the mode of carbon incorporation, morphology, % GC content and the presence or absence of key specific enzymes. Example 4, Table 2 shows key traits determined for *Methylomonas* 16a in relation to the three major groupings of methanotrophs. The strain clearly falls into the Type I grouping based on every trait, with the exception of nitrogen fixation. It is generally well accepted that these organisms do not fix nitrogen. Therefore, *Methylomonas* 16a appears unique in this aspect of nitrogen metabolism.

16SrRNA extracted from the strain was sequenced and compared to known 16SrRNAs from other microorganisms. The data showed 96% identity to sequences from *Methylomonas* sp. KSP III and *Methylomonas* sp. strain LW13. Based on this evidence, as well as the other physiological traits described in Table 2 (Example 4), it was concluded that the strain was a member of the genus *Methylomonas.*

Metabolic and Physiological Characterization of *Methylomonas* 16a

Carbon Metabolism: The present methanotrophic bacterial strain, *Methylomonas* 16a, converts methane to methanol via a methane monooxygenase as the first step in carbon utilization. The methane monooxygenase present in the strain is a particulate, as opposed to a soluble, monooxygenase. Particulate methane monooxygenases (pMMO) are well known in the art (Murrell et al., *Arch. Microbiol.* (2000), 173(5–6), 325–332) and many have been isolated and sequenced. pMMO's are characterized by their narrow substrate specificity as opposed to sMMO's which are less discriminating. For this reason the pMMO enzyme is favored for the production of bulk chemicals since the sMMO is likely to modify many of the chemical intermediates needed for the efficient production of a specific product.

The gene and gene product corresponding to the pMMO isolated from the present strain have been sequenced and functionally identified on the basis of homology comparisons to sequences in publicly available databases. The instant sequence is highly homologous to that isolated from *Methylococcus capsulatus* (GenBank B57266).

The present strain contains several anomalies in the carbon utilization pathway. For example, based on genome sequence data, the strain is shown to contain genes for two pathways of hexose metabolism. The Entner-Douderoff Pathway utilizing the keto-deoxy phosphogluconate aldolase enzyme is present in the strain. Is generally well accepted that this is the operative pathway in obligate methanotrophs. Also present, however, is the Embden-Meyerhof pathway which utilizes the fructose bisphosphate aldolase enzyme. It is well known that this pathway is either not present or not operative in obligate methanotrophs. Energetically, the latter pathway is most favorable and allows greater yield of biologically useful energy, ultimately resulting in greater yield production of cell mass and other cell mass-dependent products in *Methylomonas* 16a. The activity of this pathway in the present 16a strain has been confirmed through microarray data and biochemical evidence measuring the reduction of ATP. Although the 16a strain has been shown to possess both the Embden-Meyerhof and the Entner-Douderoff pathway enzymes the data suggests that the Embden-Meyerhof pathway enzymes are more strongly expressed than the Entner-Douderoff pathway enzymes. This result is surprising and counter to existing beliefs concerning the glycolytic metabolism of methanotrophic bacteria. Applicants have discovered other methanotrophic bacteria having this characteristic, including for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain 16a is that the key phosphofructokinase step is pyrophosphate dependent instead of ATP dependent. This feature adds to the energy yield of the pathway by using pyrophosphate instead of ATP (Example 6). Because of its significance in providing an energetic advantage to the strain, this gene in the carbon flux pathway is considered diagnostic for the present strain.

Comparison of the pyrophosphate dependent phosphofructokinase gene sequence (SEQ ID NO:5) and deduced amino acid sequence (SEQ ID NO:6) to public databases reveals that the most similar known sequences is about 63% identical to the amino acid sequence reported herein over a length of 437 amino acid using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). More preferred amino acid fragments are at least about 80%–90% identical to the sequences herein. Most preferred are nucleic acid fragments that are at least 95% identical to the amino acid fragments reported herein. Similarly, preferred pyrophosphate dependent phosphofructokinase encoding nucleic acid sequences corresponding to the instant gene are those encoding active proteins and which are at least 80% identical to the nucleic acid sequences of reported herein. More preferred pyrophosphate dependent phosphofructokinase nucleic acid fragments are at least 90% identical to the sequences herein. Most preferred are pyrophosphate dependent phosphofructokinase nucleic acid fragments that are at least 95% identical to the nucleic acid fragments reported herein.

Accordingly the invention provides a high growth methanotrophic bacterial strain which:

(a) grows on a C1 carbon substrate selected from the group consisting of methane and methanol; and (b) comprises a functional Embden-Meyerhof carbon pathway, said pathway comprising a gene encoding a pyrophosphate dependent phosphofructokinase enzyme, the gene selected from the group consisting of:

(a) an isolated nucleic acid molecule encoding the amino acid sequence as set forth in SEQ ID NO:6;

(b) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS;

(c) an isolated nucleic acid molecule comprising a first nucleotide sequence encoding a polypeptide of at least 437 amino acids that has at least 63% identity based on the Smith-Waterman method of alignment when compared to a polypeptide having the sequence as set forth in SEQ ID NO:6; and (d) an isolated nucleic acid molecule that is complementary to (a), (b) or (c).

Figure 2:
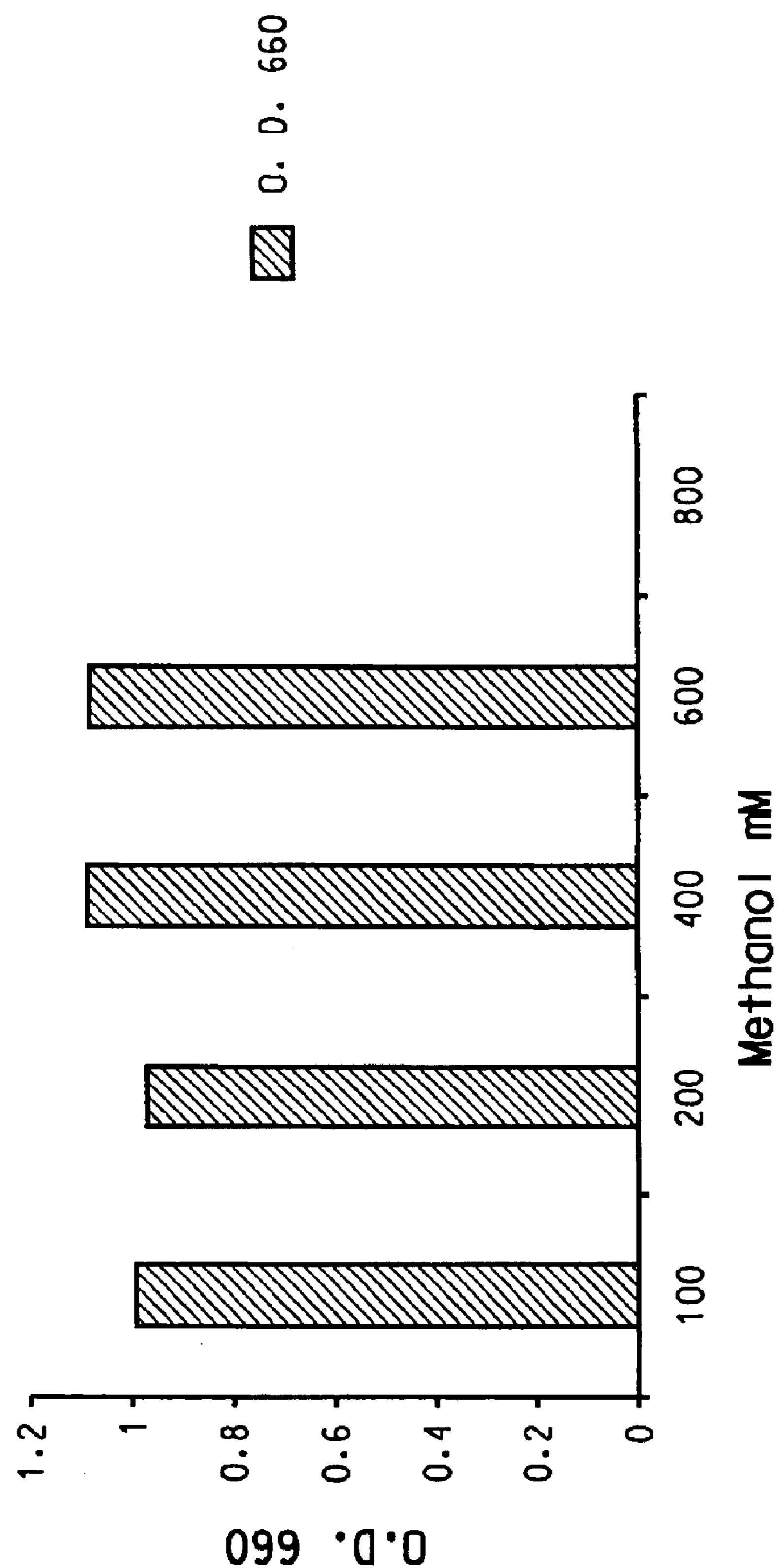
FIG. 2 is a plot of optical density vs. methanol concentration for a culture of *Methylomonas* 16a grown on methanol alone.

Methane and methanol are the only substrates shown to support growth of *Methylomonas* 16a. The strain is grown on defined medium without the addition of complex growth factors. Methanol utilization is reported to typically require "adaptation" and growth on methanol concentration ranging from 0.1% to 3% is also reported as "variable". *Methylomonas* 16a was shown to grow on methanol concentrations as high as 600 mM (2.4%) without adaptation and with good yield. (FIG. 2).

In methanotrophic bacteria methane is converted to biomolecules via a cyclic set of reactions known as the ribulose monophosphate pathway or RuMP cycle. This pathway is comprised of three phases, each phase being a series of enzymatic steps. The first step is "fixation" or incorporation of C-1 (formaldehyde) into a pentose to form a hexose or six carbon sugar. This occurs via a condensation reaction between a 5 carbon sugar (pentose) and formaldehyde and is catalyzed by hexulose monophosphate synthase. The second phase is termed "cleavage" and results in splitting of that hexose into two 3 carbon molecules. One of those three carbon molecules is recycled back through the RuMP pathway and the other 3 carbon fragment is utilized for cell growth. In methanotrophs and methylotrophs the RuMP pathway may occur as one of three variants. However, only two of these variants are commonly found: the FBP/TA (fructose bisphosphotase/Transaldolase) or the KDPG/TA (keto deoxy phosphogluconate/transaldolase) pathway. (Dijkhuizen L., G. E. Devries. The physiology and biochemistry of aerobic methanol-utilizing gram negative and gram positive bacteria. In: Methane and Methanol Utilizers 1992, ed. Colin Murrell and Howard Dalton. Plenum Press, NY).

The present strain is unique in the way it handles the "cleavage" steps as genes were found that carry out this conversion via fructose bisphosphate as a key intermediate. The genes for fructose bisphosphate aldolase and transaldolase were found clustered together on one piece of DNA.

Secondly the genes for the other variant involving the keto deoxy phosphogluconate intermediate were also found clustered together. Available literature teaches that these organisms (methylotrophs and methanotrophs) rely solely on the KDPG pathway and that the FBP-dependent fixation pathway is utilized by facultative methylotrophs (Dijkhuizen et al., supra). Therefore the latter observation is expected, whereas the former is not. The finding of the FBP genes in an obligate methane utilizing bacterium is both surprising and suggestive of utility. The FBP pathway is energetically favorable to the host microorganism due to the fact that less energy (ATP) is utilized than is utilized in the KDPG pathway. Thus organisms that utilize the FBP pathway may have an energetic advantage and growth advantage over those that utilize the KDPG pathway. This advantage may also be useful for energy-requiring production pathways in the strain. By using this pathway, a methane-utilizing bacterium may have an advantage over other methane utilizing organisms as production platforms for either single cell protein or for any other product derived from the flow of carbon through the RuMP pathway.

Accordingly the present invention provides a *Methylomonas* having two distinct carbon flux pathways, comprising genes and gene products as set forth in SEQ ID NO:1–20, and encoding both a pyrophosphate dependent phosphofructokinase pyrophosphate and a keto-deoxy phosphogluconate (KDPG) aldolase. Comparison of the KDPG aldolase gene sequence (SEQ ID NO:19) and deduced amino acid sequence (SEQ ID NO:20) to public databases reveals that the most similar known sequences is about 59% identical to the amino acid sequence of reported herein over a length of 212 amino acid using a Smith-Waterman alignment algorithm (W. R. Pearson, supra). More preferred amino acid fragments are at least about 80%–90% identical to the sequences herein. Most preferred are nucleic acid fragments that are at least 95% identical to the amino acid fragments reported herein. Similarly, preferred KDPG aldolase encoding nucleic acid sequences corresponding to the instant gene are those encoding active proteins and which are at least 80% identical to the nucleic acid sequences of reported herein. More preferred KDPG aldolase nucleic acid fragments are at least 90% identical to the sequences herein. Most preferred are KDPG aldolase nucleic acid fragments that are at least 95% identical to the nucleic acid fragments reported herein.

It is thus an object of the invention to provide a high growth methanotrophic bacterial strain having the ability to grow exclusively on either methane or methanol, comprising a functional Embden-Meyerhof carbon pathway, said pathway comprising a gene encoding a pyrophosphate dependent phosphofructokinase enzyme and at least one gene encoding a keto-deoxy phosphogluconate aldolase enzyme, selected from the group consisting of:

(a) an isolated nucleic acid molecule encoding the amino acid sequence as set forth in SEQ ID NO:20;

(b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS;

(c) an isolated nucleic acid molecule comprising a first nucleotide sequence encoding a polypeptide of at least 212 amino acids that has at least 59% identity based on the Smith-Waterman method of alignment when compared to a polypeptide having the sequence as set forth in SEQ ID NO:20; and (d) an isolated nucleic acid molecule that is complementary to (a), (b) or (c).

Figure 3:
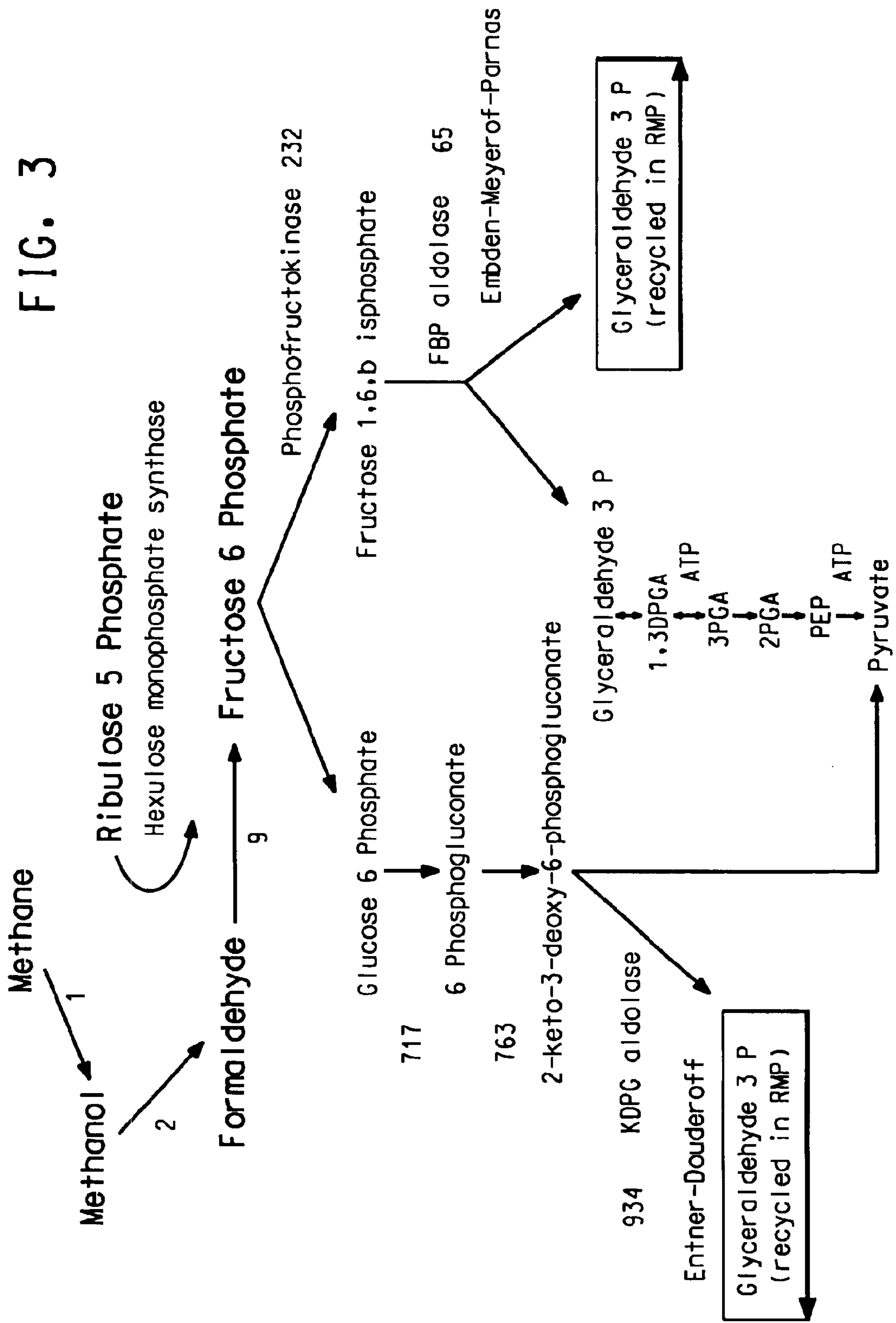
FIG. 3 represents a schematic of the Entner-Douderoff and Embden-Meyerhof pathways in *Methylomonas* 16a showing microarray expression results numerically ranked in order of decreasing expression level.

In addition to the pyrophosphate dependent phosphofructokinase enzyme and keto-deoxy phosphogluconate aldolase enzyme, the strain comprises other carbon flux genes including an FBP aldolase, phosphoglucomutase, pyrophosphate dependent phosphofructokinase pyrophosphate, 6-Phosphogluconate dehydratase, and a glucose-6 phosphate-1dehydrogenase. The phosphoglucomutase is responsible for the interconversion of glucose-6-phosphate to glucose-1-phosphate, which feeds into either the Entner-Douderoff or Embden-Meyerhof carbon flux pathways. As shown in FIG. 3, fructose-6-phosphate may be convert to either glucose-6-phosphase by glucose phosphate isomerase (Entner-Douderoff) or to fructose-1,6-bisphosphate (FBP) by a phosphofructokinase (Embden-Meyerhof). Following the Embden-Meyerhof pathway, FBP is then taken to two three-carbon moieties (dihydroxyacetone and 3-phosphoglyceraldehyde) by the FBP aldolase. Returning to the Entner-Douderoff system, glucose-6-phosphate is taken to 6-phosphogluconate by a glucose-6-phosphate dehydrogenase which is subsequently taken to 2-keto-3-deoxy-6-phosphogluconate (KDPG) by a 6 phosphogluconate dehydratase. The KDPG is then converted to two three-carbon moieties (pyruvate and 3-phosphoglyceraldehyde) by a KDPG aldolase. Thus the Embden-Meyerhof and Entner-Douderoff pathways are rejoined at the level of 3-phosphoglyceraldehyde.

Identification of High Growth Methanotrophic Bacteria

Although the present 16a strain has been isolated fortuitously, it is contemplated that the present teaching will enable the general identification and isolation of similar strains. For example, the key characteristics of the present high growth strain are that it is an obligate methanotroph, using only either methane or methanol as a sole carbon source; and it possesses a functional Embden-Meyerhof pathway, and particularly a gene encoding a pyrophosphate dependent phosphofructokinase. Methods for the isolation of methanotrophs are common and well known in the art (See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.,* 36, 227, (1992)). Similarly pyrophosphate dependent phosphofructokinase has been well characterized in mammalian systems and assay methods have been well developed (see for example Schliselfeld et al. *Clin. Biochem.* (1996), 29(1), 79–83; Clark et al., *J. Mol. Cell. Cardiol.* (1980), 12(10), 1053–64). The contemporary microbiologist will be able to use these techniques to identify the present high growth strain.

The specific strain of the present invention possesses a specific pyrophosphate dependent phosphofructokinase having the amino acid sequence as set forth in SEQ ID NO:6. The present strain may be further characterized by analyzing a methanotrophic bacterial strain for the presence of the gene encoding this enzyme.

It is therefore an object of the invention to provide a method of identifying a high growth methanotrophic bacterial strain comprising:

(a) growing a sample suspected of containing a high growth methanotrophic bacterial strain on a suitable growth medium in the presence of methane as a sole carbon source;

(b) identifying colonies that grow on the conditions of step (a);

(c) analyzing the colonies identified in step (b) for the presence of pyrophosphate dependent phosphofructokinase activity.

Growth Characteristics: The presence of the above mentioned carbon flux characteristics was previously unknown in methanotrophic bacteria and may explain the rapid growth rate and the increased carbon conversion efficiency of this strains and other strains possessing this pathway, relative to strain that do not have this pathway. The present *Methylomonas* 16a has been shown to grow on methane with a doubling time of only 2.5 h. This is a very high growth rate and is an obvious advantage for commercial use as well as for the genetic manipulations performed in development of the strain. Additionally, *Methylomonas* has no requirement for organic growth factors such as yeast extract or other costly fermentation additives. The strain requires only methane or methanol, inorganic minerals, oxygen and water for optimum growth, giving the present strain an advantage for large scale growth at low cost.

Particularly noteworthy is the high yield of the present strain. Yield is defined herein as the amount of cell mass produced per gram of carbon substrate metabolized. The present strain has shown the ability to produce greater than 0.8 and preferably greater than 1.0 grams of cell mass per gram of methane metabolized. Similarly the present strain has shown the ability to produce greater than 0.30 and preferably greater than 0.45, more preferably greater than 0.5 grams of cell mass per gram of methanol metabolized.

Carbon conversion efficiency is another measure of how much carbon is assimilated into cell mass. Carbon conversion efficiency is expressed in units of g/mol methane (1 g dry wt/g methane)/g/mol biomass. Carbon conversion efficiency is calculated assuming a biomass composition of $CH_2—O_{0.5}—N_{0.25}$. The present strain will have a particularly high carbon conversion efficiency where an efficiency of greater than 40 is common, an efficiency of greater than 50 is preferred, a conversion of greater than 65 is highly preferred and an efficient of greater than 70 g/mol methane is most preferred.

Methanol Utilization: *Methylomonas* 16a is shown to grow at methanol concentrations as high as 600 mM. Typically methanol can be toxic at these concentrations to some methanotrophic bacteria. *Methylomonas* 16a can tolerate up to about 2.4% methanol which is at the upper end of the known spectrum of methanol tolerance for methanotrophic bacteria (Green, Peter, Taxonomy of Methylotrophic Bacteria. In: Methane and Methanol Utilizers (Biotechnology Handbooks 5) J. Colin Murrell and Howard Dalton eds., 1992 Pleanum Press NY, pp 23–84). This feature again allows for much lower capital costs in reactor design since tolerance for methanol is higher necessitating reactors with fewer mixing ports (i.e. lower construction costs). This issue (high reactor costs due to mixing requirements to overcome methanol toxicity) is a major drawback to growth of methanotrophic bacteria on methanol.

Glycogen Production: *Methylomonas* 16a has been shown to produce in excess of 50% of its weight as glycogen during active growth on methanol and significant amounts of glycogen during active (non-stress associated) growth on methane. This aspect is useful for the production of mixtures of protein and carbohydrate to serve a wider array of animal feed nutritional needs as compared to other obligate methanotrophs producing only protein as the sole product. Alternatively, this trait enables *Methylomonas* 16a to serve as a host strain for the production of glycogen from methane or methanol. Furthermore, internal hexose metabolism is clearly occurring in *Methylomonas* 16a. Thus the organism can serve as host for the production of chemical products typically considered to be only produced by carbohydrate metabolism. Accordingly the invention provides a *Methylomonas* strain having the ability to produce in excess of 50% of its weight of glycogen when grown on methanol, where about 20% to about 40% is typical.

Pigment and Terpenoid Production: The present *Methylomonas* strain is useful for the production of a variety of pigments and particularly the isoprenoid pigments. This class of pigments are known to have strong light absorbing properties and are derived from the head to tail condensation of 5, 10, 15, 20, 25, 30 or 40 carbon isoprene chains. One specific pigment identified in the present strain is a C-30 carotenoid. The content of this pigment is very high in the cell and is indicative of naturally high carbon flow through the isoprenoid pathway. This aspect provides the basis for viewing the isoprenoid pathway as a "backbone production pathway" for isoprenoid-derived products. It is contemplated for example that high value carotenoids such as astaxanthin, β-carotene, canthaxanthin, and lutein may be produced by the instant organism.

Additionally the present strain is expected to have the ability to produce various isoprenoid compounds. Isoprenoids are an extremely large and diverse group of natural products that have a common biosynthetic origin based on a single metabolic precursor known as isopentenyl diphosphate (IPP). The group of natural products known as isoprenoids includes all substances that are derived biosynthetically from the 5-carbon compound isopentenyl diphosphate. Isoprenoid compounds are also referred to as "terpenes" or "terpenoids", which is the term used in the designation of the various classes of these examples (Spurgeon and Porter, Biosynthesis of Isoprenoid Compounds, pp 3–46, A Wiley-Interscience Publication (1981)). Isoprenoids are ubiquitous compounds found in all living organisms. Some of the well-known examples of isoprenoids are steroids (triterpenes), carotenoids (tetraterpenes), and squalene, just to name a few.

The biosynthesis of such compounds typically involve the enzyme isopentenyl pyrophosphate and are formed by the head to tail condensation of isoprene units which may be of 5, 10, 15, 20, 30 or 40 carbons in length.

It is contemplated that other, related, small cyclic molecules such as limonene, menthol and geraniol may be produced in the present strain via the introduction of the appropriate plant-derived terpene synthases. Thus the isoprenoid pathway may be viewed as a platform pathway for production of complex cyclic and unsaturated molecules from methane or methanol. This capability is unique to biology, purely chemical processes cannot convert C-1 compounds to cyclic molecules with any degree of specificity.

Many steps in isoprenoid pathways are known. For example, the initial steps of the alternate pathway involve the condensation of 3-carbon molecules (pyruvate and C1 aldehyde group, D-glyceraldehyde 3-Phosphate), to yield a 5-carbon compound (D-1-deoxyxylulose-5-phosphate). Lois et al. has reported a gene, dxs, that encodes D-1-deoxyxylulose-5-phosphate synthase (DXS) that catalyzes the synthesis of D-1-deoxyxylulose-5-phosphate in *E. coli* (*Proc. Natl. Acad. Sci. USA* 95: 2105–2110 (1998)).

Next, the intramolecular rearrangement of D-1-deoxyxylulose-5-phosphate occurs by an unspecified reduction process for the formation of 2-C-methyl-D-erythritol-4-phosphate. One of the enzymes involved in the reduction process is D-1-deoxyxylulose-5-phosphate reductoisomerase (DXR). Takahashi et al. reported the dxr gene product catalyzes the formation of 2-C-methyl-D-erythritol-4-phosphate in the alternate pathway in *E. coli* (*Proc. Natl. Acad. Sci. USA* 95: 9879–9884 (1998)).

Steps converting 2-C-methyl-D-erythritol-4-phosphate to isopentenyl monophosphate are not well characterized although some steps are known. 2-C-methyl-D-erythritol-4-phosphate is converted into 4-diphosphocytidyl-2C-methyl- D-erythritol in a cytosine triphosphate (CTP) dependent reaction by the enzyme encoded by non-annotated gene ygbP, encoding a 2C-methyl-d-erythritol cytidylyltransferase. Rondich et al. reported a YgbP protein in *E. coli* that catalyzes the reaction mentioned above (*Proc. Natl. Acad. Sci. USA* 96:11758–11763 (1999)). Recently, ygbP gene was renamed as ispD as a part of the isp gene cluster. The 2 position hydroxy group of 4-diphosphocytidyl-2C-methyl-D-erythritol can be phosphorylated in an ATP dependent reaction by a 4-diphosphocytidyl-2-C-methylerythritol kinase encoded by the ychB gene. Luttgen et al. has reported a YchB protein in *E. coli* that phosphorylates 4-diphosphocytidyl-2C-methyl-D-erythritol, resulting in 4-diphosphocytidyl-2C-methyl-D-erythritol 2-phosphate (*Proc. Natl. Acad. Sci. USA* 97:1062–1067 (2000)). Recently, the ychB gene was renamed as ispE as a part of the isp gene cluster.

Herz et al. reported that the ygbB gene product (2C-methyl-d-erythritol 2,4-cyclodiphosphate synthase) in *E. coli* converts 4-diphosphocytidyl-2C-methyl-D-erythritol 2-phosphate to 2C-methyl-D-erythritol 2,4-cyclodiphosphate in a CTP dependent reaction. 2C-methyl-D-erythritol 2,4-cyclodiphosphate can be further converted into carotenoids through the carotenoid biosynthesis pathway (*Proc. Natl. Acad. Sci. USA* 97:2486–2490 (2000)). Recently, the ygbB gene was renamed as ispF as a part of isp gene cluster.

Both reactions catalyzed by the YgbB and YgbP enzymes are carried out in CTP dependent manner. Thus CTP synthase plays an important role in the isoprenoid pathway. PyrG encoded by the pyrG gene in *E. coli* was determined to encode CTP synthase (Weng et al., *J. Biol. Chem.,* 261:5568–5574 (1986)).

Following several reactions not yet characterized, isopentenyl monophosphate is formed. Isopentenyl monophosphate is converted to an isopentenyl diphosphate (IPP) by isopentenyl monophosphate kinase enzyme encoded by the ipk gene (Lange and Croteau, *Proc. Natl. Acad. Sci. USA* 96:13714–13719 (1999)).

Prenyltransferases constitute a broad group of enzymes catalyzing the consecutive condensation of isopentenyl diphosphate (IPP), resulting in the formation of prenyl diphosphates of various chain lengths. Homologous genes of prenyl transferase have highly conserved regions in their amino acid sequences. Ohto et al. reported three prenyl transferase genes in cyanobacterium *Synechococcus elongatus* (*Plant Mol. Biol.* 40:307–321 (1999)). They are geranylgeranyl (C20) diphosphate synthase, farnesyl (C15) diphosphate synthase (ispA), and another prenyltransferase that can catalyze the synthesis of five prenyl diphosphates of various length.

Further down in the isoprenoid biosynthesis pathway, more genes are involved in the synthesis of specific isoprenoids. As an example, the crtN gene that was found in *Heliobacillus mobilis* (*Proc. Natl. Acad. Sci. USA* 95:14851–14856 (1998)) encodes a diapophytoene dehydrogenase that is a part of the carotenoid biosynthesis pathway.

Although some of the genes involved in isoprenoid pathways are well known, the presence of genes involved in the isoprenoid pathway of *Methylomonas* sp. is rare. It is surprising therefore to find all of the above mentioned genes in the present strain (SEQ ID NO:61–SEQ ID NO:78). Tgus suggests that the present strain will be useful for the production of a variety of terpenoids. Accordingly the invention provides a *Methylomonas* strain having the genes and gene products as set forth in SEQ ID NO:61–SEQ ID NO:78, encoding a D-1-deoxyxylulose-5-phosphate synthase, a D-1-deoxyxylulose-5-phosphate reductoisomerase, 2C-methyl-d-erythritol 2,4-cyclodiphosphate synthase, a 2C-methyl-d-erythritol cytidylyltransferase, a CTP synthase, a Geranyltranstransferase (also farnesyl-diphosphate synthase), a 4-diphosphocytidyl-2-C-methylerythritol kinase, and a diapophytoene dehydrogenase.

Production of Single Cell Protein: The present strain is useful for the production of single cell protein (SCP) which has value in the food and feed industries. Methods for the use of methanotrophs as production platforms for the production of SCP are well known in the art (see for example U.S. Pat. No. 4,795,708; Shojaosadati et al., *Amirkabir* (1996), 8(30), 33–41). The present strain is well suited for this application due to its advantages in carbon flux and reduced oxygen consumption in the presence of a nitrogen source. The strain is well suited for the production of single cell protein under either aerobic or anaerobic conditions.

The present strain compares favorably with other known strains, producing up to about 1.3 g protein/dry weight g methane and up to about 0.45 g protein/dry weight g methanol.

Production of exopolysaccharides: Polysaccharides are sugar polymers that have been used widely as a thickener in food and non-food industries (Sanford et al. *Pure & Appl. Chem.* 56: 879–892 (1984); Sutherland, *Trends Biotechnol,* 16(1): 41–6 (1998)). They can be found in food products such as salad dressing, jam, frozen food, bakery products, canned food and dry food. Many other applications include suspending agents for pesticides, paints and other coating agents. They can act as flocculent, binders, film-formers, lubricants and friction reducers. Furthermore, exopolysaccharides are commonly used in the oil field for oil recovery.

Traditionally, industrially useful polysaccharides have been derived from algal and plant sources. Over the past decade polysaccharides derived from microbes have been found increased usage (Sanford et al. *Pure & Appl. Chem.* 56: 879–892 (1984); Sutherland, *Trends Biotechnol,* 16(1): 41–6 (1998)).

Many other genes involved in exopolysaccharide biosynthesis have been characterized or sequenced from other organisms. The epsB gene encodes the EpsB protein that is probably involved in polymerization and/or export of EPS, and has been sequenced in *Ralstonia sola* (Huang et al, *Mol. Microbiol.* 16: 977–989 (1995)). The espM gene encoding the EspM protein has been found in the esp gene cluster from *Streptococcus thermophilus* (Stingele et al, *J. Bacteiol.* 178: 1680–1690 (1996)). Another putative polysaccharide export protein, WZA, is identified in *E. coli*. (Blattner et al., *Science* 277: 1453–1474 (1997)). Finally, the epsV gene encodes the EpsV protein, a transferase which transfers the sugar to polysaccharide intermediates, and it has also been sequenced in *Streptococcus thermophilus* (Bourgoin et al., *Plasmid* 40: 44–49 (1998); Bourgoin, F., et al., *Gene* 233:151–161 (1999)).

In spite of the abundance of information regarding genes encoding microbial exopolysaccharides, no genes involved in this pathway have been isolated or characterized from C1 utilizing organisms, such as *Methylomonas.* As noted above, microbial exopolysaccharides have a variety of uses and it would be an advantage to synthesize this material from an abundant and inexpensive carbon source such as methane.

Surprisingly, the present *Methylomonas* 16a has been shown to produce extrapolysaccharides at high levels. The genes encoding the relevant polysaccharide synthesis pathways have been isolated and characterized and are described along with their gene products in SEQ ID NO:21–SEQ ID NO:38.

Accordingly, the present invention provides a *Methylomonas* strain having the ability to synthesize exopolysaccharides and having genes encoding the ugp, gumD, wza, epsB, epsM, waaE, epsV, gumH and glycosyl transferase proteins associated with microbial polysaccharide biosynthesis.

Denitrification: The presence of denitrification enzymes in obligate methanotrophs is unknown. The present strain contains a pathway comprised of genes and gene products as set forth in SEQ ID NO:39–SEQ ID NO:60. A novel feature of the present *Methylomonas* 16a is the ability to utilize a nitrogen source at low oxygen tensions as an additional "electron sink" for reducing equivalents derived from methane or methanol. Nitrogen sources may include, but are not limited to, nitrite, nitrate, ammonium and dinitrogen. The strain is shown to reduce nitrate or nitrite to nitrous oxide which is a gaseous end-product. The utility in this process is that nitrate is very soluble as well as inexpensive and use of nitrate mitigates against the high energy requirement for maintaining dissolved oxygen in the process. In fact, nitrate is utilized as an accessory oxidant in some waste water treatment systems (Koch, Gerhard; Siegrist, Hansruedi Verbandsber.-Verb. Schweiz. Abwasser-Gewaesserschutzfachleute (1998), 522 (Optimierungsmassnahmen bei Stark Belasteten Belebungsanlagen), 33–48).

In non-methanotrophic denitrifiers, the microbial process known as denitrification is catalyzed by a series of enzymes which together reductively convert nitrate to gaseous dinitrogen. The steps and intermediates in the process as shown below, together with the enzyme names and gene designations define the scope of the process under consideration.

1. $NO_3 \rightarrow NO_2$ Respiratory nitrate reductase (Nar genes).
2. $NO_2 \rightarrow NO$ Respiratory nitrite reductase (Nir genes)
3. $NO \rightarrow N_2O$ Nitric oxide reductase (Nor genes)
4. $N_2O \rightarrow N_2$ Nitrous oxide reductase (Nos genes)

Ecologically, the result of these processes is removal of nitrogen from soils (denitrification). However, nitrate can also be viewed as a supplemental or alternative oxidant to oxygen. This is due to the very positive redox potential of the denitrification process.

A second major microbial process is referred to as nitrification and that is comprised of the following set of reactions, enzymes and genes.

1. $NH_4 \rightarrow NH_2OH$ Ammonia monooxygenase (amo genes)
2. $NH_2OH \rightarrow NO_2$ (Hydroxylamine oxidoreductase)
3. $NO_2 \rightarrow NO_3$ (Nitrite oxidase)

Nitrification is an oxidative process generating nitrate in soils whereas denitrification is a reductive process depleting nitrate in soils.

It is well known that obligatory methanotrophic bacteria belong to the group of nitrifying bacteria. This is due to the ability of methane monooxygenase which is found in all obligate methanotrophs to oxygenate ammonia to form hydroxylamine in a reaction identical to that of ammonia monooxygenase and analogous to methane oxygenation to form methanol. The hydroxylamine is then further metabolized enzymatically to nitrite. Nitrite oxidation to nitrate can occur enzymatically or spontaneously in air via chemical oxidation. However methanotrophic bacteria have been indirectly associated with denitrification by virtue of their association with denitrifying bacteria such as Hyphomicrobium species (Amaral, J. A. Archambault, C. S. R. Richards, R. Knowles 1995. *FEMS Microbiology Ecology* 18 289–298). The respiratory processes described above are distinct from the reduction of nitrate or nitrite for cellular assimilation. The former respiratory process is energy yielding whereas the latter assimilatory process provides nitrogen for incorporation into cellular mass. The assimilatory process relies upon pyridine nucleotide linked nitrate or nitrite reductases. These enzymes are widely found in nature including the methanotrophic bacteria. Growth of methanotrophs on nitrate as a sole nitrogen source for biosynthesis is well known in the existing literature (Hanson R. S. A. I. Netrusov, K. Tsuji. 1992. The obligate methanotrophic bacteria Methylococcus, *Methylomonas,* and *Methylosinus.* In: The Prokaryotes $2^{nd}$ ed. Ch 18. Pp 2350–2363, A. Balows, H. G. Truper, M. Dworkin, W. Harder, K-H Schleifer eds. Springer Verlag).

The functionality of the genes described herein (SEQ ID NO:39–SEQ ID NO:60) lie in the respiratory reduction of nitrate or nitrite to gaseous $N_2O$. All genes required to perform this function have been shown to be present in *Methylomonas* 16a both by sequence analysis and physiological reduction of nitrogen containing compounds. Additionally the genes encoding enzymes necessary for the biotransformation of ammonia (nitrification) are also present.

The advantages to the presence of this denitrification capability in an obligate methanotroph are at least two fold:

1. Nitrate may replace or supplement oxygen as an electron acceptor needed for growth. This can be advantageous for large scale cost-effective cultivation with highly reduced feedstocks that require excessive oxygen demand leading to excessive costs for mass-transfer of gaseous oxygen into solution.
2. Methanotrophic denitrification may be used to remove soluble nitrates from waters or processes where nitrates or other oxygenated nitrogen derivatives are problematic.

Due to the ability of *Methylomonas* 16a to convert ammonia to nitrite combined with the ability to convert nitrite to nitrous oxide demonstrated in the present invention, *Methylomonas* 16a and other methanotrophs which efficiently reduce nitrite can be used as agents to remove ammonia from process waters, waste waters, or natural waters or agricultural effluents for the purpose of clean up and detoxification Gene Transfer into *Methylomonas* 16a: *Methylomonas* 16a has been shown to accept and express genes form other organisms including *Escherichia coli* and yeast. Several plasmid vectors have been identified which facilitate both gene transfer from a donor organism and expression of the gene in *Methylomonas* 16a. Thus the strain can be genetically engineered.

Production of Food and Feed Substrates

It will be appreciated that the present *Methylomonas* 16a strain has the ability to produce, not only proteins, polysaccharides and pigments individually, but may also be engineered to produce a uniquely tailored food or feed product comprising specific quantities and desirable mixtures of these materials. This characteristic of the present strain has significant commercial value.

For example, different livestock animal types may have different nutritional requirements in terms of the relative proportions of protein to carbohydrate. Many carnivorous aquatic fish species, for example, have very high protein requirements. Ruminant livestock, on the other hand, thrive on higher fiber/carbohydrate diets. *Methylomonas* 16a has the capacity to form large amounts of carbohydrate, under certain conditions, in addition to the cellular protein which is always produced. Genes involved in gluconeogenesis (glycogen formation) or glycogen degradation might be altered or regulated such that glycogen content could either be decreased or increased. Thus the composition of the crude cell mass could be modulated to target high protein feed markets (lower carbohydrate) or alternatively, higher carbohydrate lower protein feed markets. The ability to engineer the composition of the microbe precludes the need to artificially formulate protein/carbohydrate ratios by exogenous additions.

Carotenoid pigments play a role in terms of providing coloration for many aquatic fish and crustacean species as well as providing antioxidant benefit. (Nelis H. J., De Leenheer 1991. *J. Appl. Bacterol.* 70:181–191). *Methylomonas* 16a, unlike many commercially utilized methanotrophs (i.e. *Methylococcus capsulatus*) has a natural carotenoid pigment production pathway which produces high levels of a pink pigment that is similar, but not structurally identical, with such high value carotenoids as astaxanthin. Modification of this pathway by addition of genes involved in the final steps of astaxanthin synthesis or other high value carotenoids will result in the ability of this strain to produce these carotenoids. In this way *Methylomonas* 16a will be uniquely useful as an animal feed production strain in which the ratios of protein/carbohydrate/pigments may be tailored to suit particular nutritional needs. In this way, *Methylomonas* may be utilized as a way to deliver higher value components to other sources of plant protein or carbohydrate and thus circumvent the problem of genetic engineering of these plants for the higher value traits.

Methods of manipulating genetic pathways are common and well known in the art. Selected genes in a particular pathway may be upregulated or down regulated by variety of methods. Additionally, competing pathways in the organism may be eliminated or sublimated by gene disruption and similar techniques.

Once a key genetic pathway has been identified and sequenced specific genes may be upregulated to increase the output of the pathway. For example, additionally copies of the targeted genes may be introduced into the host cell on multicopy plasmids such as pBR322. Alternatively, the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods of gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al. (1989) *J. Bacteriol.* 171:4617–4622; Balbas et al. (1993) *Gene* 136:211–213; Gueldener et al. (1996) *Nucleic Acids Res.* 24:2519–2524; and Smith et al. (1996) *Methods Mol. Cell. Biol.* 5:270–277.)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.,* 36, 227, (1992).

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Within the context of the present invention it may be useful to modulate the expression of the identified biosynthetic pathways. For example, it has been noted that the present *Methylomonas* 16a comprises genes encoding both the Entner-Douderoff and Embden-Meyerhof carbon flux pathways. Because the Embden-Meyerhof pathway is more energy efficient it may be desirable to over-express the genes in this pathway. Additionally, it is likely that the Entner-Douderoff pathway is a competitive pathway and inhibition of this pathway may lead to increased energy efficiency in the Embden-Meyerhof system. This might be accomplished by selectively using the above described methods of gene down regulation on the sequence encoding the keto-deoxy phosphogluconate aldolase (SEQ ID NO:9) or any of the other members of the Entner-Douderoff system and upregulating the gene encoding the fructose bisphosphatase aldolase of the Embden-Meyerhof system (SEQ ID NO:50R 7). In this fashion the carbon flux in the present *Methylomonas* 16a may be optimized. Additionally, where the present strain has been engineered to produce specific organic materials such as aromatics for monomer production, optimization of the carbon flux pathway will lead to increased yields of these materials.

In a similar fashion the genes encoding the key enzymes involved in isoprenoid or pigment synthesis may be modulated. For example, the present invention provides a number of genes encoding key enzymes in the terpenoid pathway leading to the production of pigments and smaller isoprenoid compounds. The isolated genes include the dxs and dsr genes, the ispA, D, E, F, and G genes, the pyrG gene, and crtN genes. In particular it may be useful to up-regulate the initial condensation of 3-carbon molecules (pyruvate and C1 aldehyde group, D-glyceraldehyde 3-Phosphate), to yield the 5-carbon compound (D-1-deoxyxylulose-5-phosphate) mediated by the dxs gene. Alternatively, if it is desired to produce a specific non-pigmented isoprenoid, it may be desirable to disrupt various genes at the downstream end of the pathway. For example, it may be desirable to use gene disruption or antisense inhibition of the crtN gene (known to encode diapophytoene dehydrogenase) if a smaller, upstream terpenoid is the desired product of the pathway.

As has been noted, the present strain has the ability to product polysaccharides in large amounts. This process is governed by a set of genes including the ugp gene, gumD and H genes, the epsB, M, and V genes and the waaD gene. In this pathway it may be of particular importance to up-regulate the espB gene involved in polymerization and/or export of the polysaccharide, or the epsV gene which controls the transfer of sugar to polysaccharide intermediates.

In this fashion the present strain, or a similar strain may be engineered to produce specific compositions of materials or specific combinations of protein, polysaccharides and pigments for use as a food and feed product.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Microbial Cultivation and Preparation of Cell Suspensions, and Associated Analyses.

*Methylomonas* 16a is typically grown in serum stoppered Wheaton bottles using a gas/liquid ratio of at least 8:1 (i.e. 20 mL of Nitrate liquid media) media in a Wheaton bottle (Wheaton Scientific, Wheaton Ill.) of 160 mL total volume. The standard gas phase for cultivation contained 25% methane in air. These conditions comprise growth conditions and the cells are referred to as growing cells. In all cases the cultures were grown at 30° C. with constant shaking in a Lab-Line rotary shaker unless otherwise specified.

Cells obtained for experimental purposes were allowed to grow to maximum optical density (O.D. 660~1.0). Harvested cells were obtained by centrifugation in a Sorval RC-5B centrifuge using a SS-34 rotor at 6000 rpm for 20 min. These cell pellets were resuspended in 50 mM HEPES buffer pH 7. These cell suspensions are referred to as washed, resting cells.

Microbial growth was assessed in all experiments by measuring the optical density of the culture at 660 nm in an Ultrospec 2000 UVN is spectrophotometer (Pharmacia Biotech, Cambridge England) using a 1 cm light path cuvet. Alternatively microbial growth was assessed by harvesting cells from the culture medium by centrifugation as described above and resuspending the cells in distilled water with a second centrifugation to remove medium salts. The washed cells were then dried at 105° C. overnight in a drying oven for dry weight determination.

Methane concentration was determined as described by Emptage et al. (1997 *Env. Sci. Technol.* 31:732–734), hereby incorporated by reference.

Nitrate Medium for *Methylomonas* 16A

Nitrate liquid medium, also referred to herein as "defined medium" was comprised of various salts mixed with solution 1 as indicated below or where specified the nitrate was replaced with 15 mM ammonium chloride.

Solution 1 Composition for 100 fold concentrated stock solution of trace minerals.

| | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |

-continued

| | MW | Conc. (mM) | g per L |
|---|---|---|---|
| $Na_2MoO_4 \times 2H_2O$ | 241.95 | 0.04 | 0.01 |
| $NiCl_2 \times 6H_2O$ | 237.7 | 0.77 | 0.184 |

Mix the gram amounts designated above in 900 mL of $H_2O$, adjust to pH=7, and add $H_2O$ to an end volume of 1 L. Keep refrigerated.

Nitrate Liquid Medium:

| | MW | Conc. (mM) | g per L |
|---|---|---|---|
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7) | 238.3 | | 50 mL |
| Solution 1 | | | 10 mL |

Dissolve in 900 mL $H_2O$. Adjust to pH = 7, and add $H_2O$ to give 1 L.
For agar plates: Add 15 g of agarose in 1 L of medium, autoclave, let cool down to 50° C., mix, and pour plates.

Nitrate and Nitrite Assays 1 mL samples of cell culture were taken and filtered through a 0.2 micron Acrodisc filter to remove cells. The filtrate from this step contains the nitrite or nitrate to be analyzed. The analysis was performed on a Dionex ion chromatograph 500 system (Dionex, Sunnyvale Calif.) with an AS3500 autosampler. The column used was a 4 mm Ion-Pac AS11-HC separation column with an AG-AC guard column and an ATC trap column. All columns are provided by Dionex.

The mobile phase was a potassium hydroxide gradient from 0 to 50 mM potassium hydroxide over a 12 min time interval. Cell temperature was 35° C. with a flow rate of 1 mL/min.

Gene Isolation and Characterization

A number of genes encoding specific identifying enzymes were isolated and sequenced from *Methylomonas* 16a. These include distinguishing genes found in the Entner-Douderoff carbon flux pathway the Embden-Meyerhof carbon flux pathway, genes encoding a denitrification pathway, genes encoding an isoprenoid synthesis pathway, and genes encoding a pathway for the synthesis of exopolysaccharides. These genes were sequenced and functionally characterized by comparison of their respective sequences to information in public nucleic acid and protein databases according to the following procedures.

Genomic DNA was isolated from *Methylomonas* 16a according to standard protocols. Genomic DNA and library construction were prepared according to published protocols (Fraser et al The Minimal Gene Complement of *Mycoplasma genitalium; Science* 270, 1995). A cell pellet was resuspended in a solution containing 100 mM Na-EDTA pH 8.0, 10 mM tris-HCl pH 8.0, 400 mM NaCl, and 50 mM MgCl2.

Genomic DNA preparation After resuspension, the cells were gently lysed in 10% SDS, and incubated for 30 min at 55° C. After incubation at room temperature, proteinase K was added to 100 μg/mL and incubated at 37° C. until the suspension was clear. DNA was extracted twice with tris-equilibrated phenol and twice with chloroform. DNA was precipitated in 70% ethanol and resuspended in a solution containing 10 mM tris-HCl and 1 mM Na-EDTA (TE) pH 7.5. The DNA solution was treated with a mix of RNAases, then extracted twice with tris-equilibrated phenol and twice with chloroform. This was followed by precipitation in ethanol and resuspension in TE.

Library construction 200 to 500 μg of chromosomal DNA was resuspended in a solution of 300 mM sodium acetate, 10 mM tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease. After size fractionation, a fraction (2.0 kb, or 5.0 kb) was excised, cleaned and a two-step ligation procedure was used to produce a high titer library with greater than 99% single inserts.

Sequencing A shotgun sequencing strategy approach was adopted for the sequencing of the whole microbial genome (Fleischmann, Robert et al Whole-Genome Random sequencing and assembly of *Haemophilus influenzae* Rd *Science,* 269: 1995).

Sequence was generated on an ABI Automatic sequencer using dye terminator technology (U.S. Pat. No. 5,366,860; EP 272007) using a combination of vector and insert-specific primers. Sequence editing was performed in either DNAStar (DNA Star Inc.,) or the Wisconsin GCG program (Wisconsin Package Version 9.0, Genetics Computer Group (GCG), Madison, Wis.) and the CONSED package (version 7.0). All sequences represent coverage at least two times in both directions.

Microarray of Gene Expression

Amplification of DNA regions for the construction of DNA microarray: Specific primer pairs were used to amplify each protein specifying ORF of *Methylomonas* sp. strain 16a. Genomic DNA (10–30 ng) was used as the template. The PCR reactions were performed in the presence of HotStart Taq™ DNA polymerase (Qiagen, Valencia, Calif.) and the dNTPs (Gibco BRL Life Science Technologies, Gaithersberg, Md.). Thirty-five cycles of denaturation at 95° C. for 30 sec, annealing at 55° C. for 30 sec and polymerization at 72° C. for 2 min were conducted. The quality of PCR reactions was checked with electrophresis in a 1% argarose gel. The DNA samples were purified by the high-throughput PCR purification kit from Qiagen.

Arraying amplified ORFs. Before arraying, an equal volume of DMSO (10 μL) and DNA (10 μL) sample was mixed in 384-well microtiter plates. A generation II DNA spotter (Molecular Dynamics, Sunnyvale, Calif.) was used to array the samples onto coated glass slides (Telechem, Sunnyvale, Calif.). Each PCR product was arrayed in duplicate on each slide. After cross-linking by UV light, the slides were stored under vacuum in a desiccator at room temperature.

RNA isolation: *Methylomonas* 16a was cultured in a defined medium with ammonium or nitrate (10 mM) as nitrogen source under 25% methane in air. Samples of the minimal medium culture were harvested when the O.D. reaches 0.3 at A600 (exponential phase). Cell cultures were harvested quickly and ruptured in RLT buffer [Qiagen RNeasy Mini Kit, Valencia, Calif.] with a beads-beater (Bio101, Vista, Calif.). Debris was pelleted by centrifugation for 3 min at 14,000×g at 4° C. RNA isolation was completed using the protocol supplied with this kit. After on-column DNAase treatment, the RNA product was eluted with 50–100 μL RNAase-free. RNA preparations were stored frozen at either −20 or −80° C.

Synthesis of fluorescent cDNA from total RNA. RNA samples (7 to 15 μg) and random hexamer primers (6 μg; Gibco BRL Life Science Technologies) were diluted with RNAase-free water to a volume of 25 μL. The sample was denatured at 70° C. for 10 min and then chilled on ice for 30 seconds. After adding 14 μL of labeling mixture, the annealing was accomplished by incubation at room temperature for 10 min. The labeling mixture contained 8 μL of 5× enzyme buffer, 4 μL DTT (0.1 M), and 2 μL of 20× dye mixture. The dye mixture consisted of 2 mM of each dATP, dGTP, and dTTP, 1 mM dCTP, and 1 mM of Cy3-dCTP or Cy5-dCTP. After adding 1 to 1.5 μL of SuperScript II reverse transcriptase (200 units/mL, Life Technologies Inc., Gaithersburg, Md.), cDNA synthesis was allowed to proceed at 42° C. for 2 hr. The RNA was removed by adding 2 μL NaOH (2.5 N) to the reaction. After 10 min of incubation at 37° C., the pH was adjusted with 10 μL of HEPES (2M). The labeled cDNA was then purified with a PCR purification kit (Qiagen, Valencia, Calif.). Labeling efficiency was monitored using either $A_{550}$ for Cy3 incorporation, or $A_{650}$ for Cy5.

Fluorescent labeling of genomic DNA. Genomic DNA was nebulized to approximately 2 kb pair fragments. Genomic DNA (0.5 to 1 μg) was mixed with 6 μg of random hexamers primers (Gibco BRL Life Science Technologies) in 15 μL of water. The mix was denatured by put at boiling water for 5 minutes. Then anneal on ice for 30 sec before put at room temperature. Then 2 μL 5× Buffer 2 (Gibco BRL) and 2 ul dye mixture were added. The component of dye mixture and the labeling procedure are the same as described above for RNA labeling, except that the Klenow fragment of DNA polymerase I (5 μg/μL, Gibco BRL Life Science Technologies) was used as the enzyme. After incubation 37° C. for 2 hr, the labeled DNA probe was purified using a PCR purification kit (Qiagen, Valencia, Calif.).

Hybridization and washing Slides were first incubated with prehybridization solution containing 3.5×SSC (BRL, Life Technologies Inc., Gaithersburg, Md.), 0.1% SDS (BRL, Life Technologies Inc., Gaithersburg, Md.), 1% bovine serum albumin (BSA, Fraction V, Sigma, St. Louis, Mo.). After prehybridization, hybridization solutions (Molecular Dynamics) containing labeled probes was added to slides and covered with cover slips. Slides were placed in a humidified chamber in a 42° C. incubator. After overnight hybridization, slides were initially washed for 5 min at room temperature with a washing solution containing 1×SSC, 0.1% SDS and 0.1×SSC, 0.1% SDS. Slides were then washed at 65° C. for 10 min with the same solution for three times. After washing, the slides were dried with a stream of nitrogen gas.

Data Collection and Analysis. The signal generated from each slide was quantified with a laser scanner (Molecular Dynamics, Sunnyvale, Calif.). The images were analyzed with ArrayVision 4.0 software (Imaging Research, Inc., Ontario, Canada). The raw fluorescent intensity for each spot was adjusted by subtracting the background. These readings were exported to a spreadsheet for further analysis.

Table 1 is a description of the genes discovered and annotated for *Methylomonas* 16a. The table shows sequence % similarities, % identities, and expectation values for key genes of central carbon metabolism, denitrification, exopolysacharride synthesis, and isoprenoid biosynthesis.

Table 1 illustrates the relationship of these sequences to known sequences in the art. All sequences were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. All comparisons were done using either the BLASTNnr or BLASTXnr algorithm. The results of the BLAST comparison is given below in Table 1 which summarize the sequences to which they have the most similarity. Table 1 displays data based on the BLASTXnr algorithm with values reported in expect values. The Expect value estimates the statistical significance of the match, specifying the number of matches, with a given score, that are expected in a search of a database of this size absolutely by chance.

TABLE 1

Genes Characterized From *Methylomonas* 16a

| Gene Name | Similarity Identified | SEQ ID | SEQ ID Peptide | % Identity[a] | % Similarity[b] | E-value[c] | Citation |
|---|---|---|---|---|---|---|---|
| Phosphogluco-mutase | Phosphogluco-mutase (Glucose Phosphomutase) (Pgm)>>gi\|3241933\|gb\|AAD03475.1\| | 1 | 2 | 65% | 85% | 1.7e−140 | Lepek et al., Direct Submission \|gb\|AAD03475.1\| |
| Glucose 6 phosphate isomerase | Glucose 6 phosphate isomerase gi\|396360\|gb\|AAC43119.1 | 3 | 4 | 64% | 81% | 1.6e−136 | Blattner et al., Nucleic Acids Res. 21 (23), 5408–5417 (1993) |
| Phosphofructo kinase pyrophosphate dependent | Phosphofructo kinase pyrophosphate dependent gi\|150931\|gb\| | 5 | 6 | 63% | 83% | 1.7e−97 | Ladror et al., J. Biol. Chem. 266,16550–16555 (1991) |

TABLE 1-continued

Genes Characterized From *Methylomonas* 16a

| Gene Name | Similarity Identified | SEQ ID | SEQ ID Peptide | % Identity[a] | % Similarity[b] | E-value[c] | Citation |
|---|---|---|---|---|---|---|---|
| | AAA25675.1\| (M67447) | | | | | | |
| 6-Phosphogluconate dehydratase | 6-Phosphogluconate dehydratase gi\|4210902\|gb\|AAD12045.1\| (AF045609) | 7 | 8 | 60% | 85% | 1.6e−141 | Willis et al., J. Bacteriol. 181 (14), 4176–4184 (1999) |
| Glucose 6 phosphate 1 dehydrogenase | Glucose 6 phosphate 1 dehydrogenase gi\|397854\|emb\|CAA52858.1\| (X74866) | 9 | 10 | 58% | 85% | 9.4e−123 | Hugouvieux-Cotte-Pattat, N, TITLE Direct Submission, gi\|3978541\|emb\|CAA52858.1\| (X74866) |
| TAL | Transaldolase | 11 | 12 | 78% | 90% | 2.7e−92 | Plant Mol. Biol. 30 (1), 213–218 (1996) |
| MIPB | Transaldolase | 13 | 14 | 50% | 79% | 1e−23 | Blattner F. R. et. al Science 277:1453–1474 (1997). |
| FBA or FDA | Fructose bisphosphate aldolase | 15 | 16 | 76% | 92% | 4.1e−111 | Alefounder P. R. et. al. Mol. Microbiol. 3:723–732 (1989). |
| FBA or FDA | Fructose bisphosphate aldolase | 17 | 18 | 40% | 70% | 2.3e−39 | van den Bergh E. R. et al.; J. Bacteriol. 178:888–893 (1996) |
| KHG/KDPG | (AL352972) KHG/KDPG aldolase *Streptomyces coelicolor* | 19 | 20 | 59% | 72% | 1e−64 | Redenbach et al., Mol. Microbiol. 21(1), 77–96 (1996) |
| ugp | ugp (*Xanthomonas campestris*) | 21 | 22 | 58% | 82% | 3.2e−60 | Wei et al., Biochem. Biophys. Res. Commun. 226 (3), 607–612 (1996) |
| gumD | gumD (*Xanthomonas campestris*) | 23 | 24 | 36% | 69% | 2.5e−52 | Chou, F. L., et el, Biochem. Biophys. Res. Commun. 233 (1), 265–269 (1997) |
| wza | wza (*Escherichia coli*) | 25 | 26 | 36% | 69% | 5.8e−39 | Blattner, F. R. et al., Science 277 (5331), 1453–1474 (1997) |
| epsB | epsB (*Pseudomonas solanacearum*) | 27 | 28 | 35% | 67% | 2e−74 | Huang, J. and Schell, M., Mol. Microbial. 16 (5), 977–989 (1995) |
| epsM | epsM (*Streptococcus thermophilus*) | 30 | 20 | 23% | 55% | 1.3e−05 | Stingele, F. et al., J. Bacterial. 178 (6), 1680–1690 (1996) |
| waaE | waaE (*Serratia marcescens*) | 31 | 32 | 28% | 55% | 8.6e−09 | Pique, N et al., Unpublished Genbank number: AAC44433 |
| epsV | epsV (*Streptacoccus thermophilus*) | 33 | 34 | 21% | 56% | 2.3e−05 | Bourgoin, F. et al., Plasmid 40 (1), 44–49 (1998) |
| gumH | gumH (*Rhizobium meliloti*) | 35 | 36 | 26% | 55% | 0.00088 | Becker, A. et al., Mol. Microbial. 16 (2), 191–203 (1995) |
| glycosyl transferase | Glycosyltrans-ferase (*Actinobacillus actinimycetemcomitans*) | 37 | 38 | 51% | 80% | 1.7e−62 | Nakano, Y, Biochem. Biophys. Acta 1442:409–414 (1998) |
| nirF | NirF protein (*Pseudomonas*) | 39 | 40 | 59% | 85% | 1.3e−92 | Palmedo et al., Eur. J. Biochem. 232 (3), 737–746 (1995) |
| nirD | NirD protein (*Pseudomonas*) | 41 | 42 | 49% | 76% | 1.7e−22 | Palmedo et al., Eur. J. Biochem. 232 (3), 737–746 (1995) |
| nirL | NirL protein (*Pseudomonas*) | 43 | 44 | 49% | 73% | 6.4e−28 | Palmedo et al., Eur. J. Biochem. 232 (3), 737–746 (1995) |

TABLE 1-continued

Genes Characterized From *Methylomonas* 16a

| Gene Name | Similarity Identified | SEQ ID | SEQ ID Peptide | % Identity[a] | % Similarity[b] | E-value[c] | Citation |
|---|---|---|---|---|---|---|---|
| nirG | NirG protein (*Pseudomonas*) | 45 | 46 | 49% | 80% | 1.6e−25 | Kawasaki et al., J. Bacteriol. 179 (1), 235–242 (1997) |
| nirH | NirH protein (*Pseudomonas*) | 47 | 48 | 59% | 78% | 9.9e−33 | Kawasaki et al., J. Bacteriol. 179 (1), 235–242 (1997) |
| nirJ | NirJ protein (*Pseudomonas*) | 49 | 50 | 56% | 81% | 5.1e−88 | Kawasaki et al., J. Bacteriol. 179 (1), 235–242 (1997) |
| nasA | Nitrate reductase *Kiebsiella* | 51 | 52 | 51% | 74% | 9.2e−123 | LIN J.T., GOLDMAN B.S., STEWART V.; J. Bacteriol. 175:2370–2378 (1993). |
| norC | Nitric-oxide reductase subunit C (*Pseudomonas*) | 53 | 54 | 32% | 70% | 1e−08 | Zumft et al., Eur. J. Biochem. 219:481–490 (1994). |
| norB | Nitric-oxide reductase subunit B (*Pseudomonas*) | 55 | 56 | 39% | 70% | 3.5e−64 | Zumft et al., Eur. J. Biochem. 219:481–490 (1994). |
| norZ | Cytochrome B subunit of nitric oxide reductase (*Alcaligenes*) | 57 | 58 | 39% | 69% | 1.7e−100 | Cramm, R., Siddiqui, R. A. and Friedrich, B. J. Bacteriol. 179 (21), 6769–6777 (1997). |
| norS | Nitrite reductase (cytochrome cd1) (*Pseudomonas*) | 59 | 60 | 28% | 59% | 2.1e−25 | Glockner, A. B. and Zumft, W. G. Biochim. Biophys. Acta 1277 (1–2), 6–12 (1996) |
| dxs | 1-deoxyxylulose-5-phosphate synthase | 61 | 62 | 60% | 86% | 5.7e−149 | Lois, L. M., et al., Proc. Natl. Acad. Sci. U.S.A. 95 (5), 2105–2110 (1998) |
| dxr | 1-deoxy-d-xylulose 5-phosphate reductoisomerase | 63 | 64 | 55% | 78% | 3.3e−74 | Takahashi S et al., Proc. Nati. Acad. Sci. U.S.A. 95:9879–9884 (1998). |
| ygbB/ispF | 2C-methyl-d-erythritol 2,4-cyclodiphosphate synthase | 65 | 66 | 69% | 84% | 1.6e−36 | Herz S, et al., Proc Natl Acad Sci U.S.A. Mar. 14, 2000; 97 (6):2486-90 |
| ygbP/ispD | 2C-methyl-d-erythritol cytidylyltrans-ferase | 67 | 68 | 52% | 74% | 7.7e−36 | Rohdich F, et al., Proc Natl Acad Sci USA Oct. 12, 1999; 96 (21 ): 11758-63 |
| pyrG | CTP synthase | 69 | 70 | 67% | 89% | 2.4e−141 | Weng M., J. et al., Biol. Chem. 261:5568–5574(1986). |
| IspA | Geranyltrans-transferase (also farnesyldiphosphate synthase) | 71 | 72 | 56% | 78% | 7.8e−56 | Ohto, C et al., Plant Mol. Biol. 40 (2), 307–321 (1999) |
| ychB/IspE | 4-diphosphocytidyl-2-C-methylerythritol kinase | 73 | 74 | 50% | 72% | 8.8e−49 | Luttgen H, Proc Natl Acad Sci U.S.A. Feb. 1, 2000; 97 (3): 1062-7. |
| crtN1 | diapophytoene dehydrogenase CrtN-copy 1 | 75 | 76 | 34% | 72% | 4e−66 | Xiong, J Proc. Natl. Acad. Sci. U.S.A. 95 (25), 14851–14856 (1998) |
| crtN2 | Diapophytoene dehydrogenase CrtNù copy 2 | 77 | 78 | 49% | 78% | 1.3e−76 | Wieland, K. P. and Goetz, F. Unpublished |
| Particulate methane monooxygenase | probable methane monooxygenase 45k chain- | 79 | 80 | 71% | 85% | 0.0 | Semrau et al., J. Bacteriol. 177 (11), 3071–3079 (1995) |

TABLE 1-continued

Genes Characterized From *Methylomonas* 16a

| Gene Name | Similarity Identified | SEQ ID | SEQ ID Peptide | % Identity[a] | % Similarity[b] | E-value[c] | Citation |
|---|---|---|---|---|---|---|---|
| | *Methylococcus capsulatus* B57266 GI:2120829 | | | | | | |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance Example 1

Isolation of *Methylomonas* 16a

The original environmental sample containing the isolate was obtained from pond sediment. The pond sediment was inoculated directly into defined medium with ammonium as nitrogen source under 25% methane in air. Methane was the sole source of carbon and energy. Growth was followed until the optical density at 660 nm was stable whereupon the culture was transferred to fresh medium such that a 1:100 dilution was achieved. After 3 successive transfers with methane as sole carbon and energy source the culture was plated onto growth agar with ammonium as nitrogen source and incubated under 25% methane in air. Many methanotrophic bacterial species were isolated in this manner. However, *Methylomonas* 16a was selected as the organism to study due to the rapid growth of colonies, large colony size, ability to grow on minimal media, and pink pigmentation indicative of an active biosynthetic pathway for carotenoids.

Example 2

Rapid Growth on Methane in Minimal Medium

*Methylomonas* 16a grows on the defined medium comprised of only minimal salts, a culture headspace comprised of methane in air. Methane concentrations for growth but typically are 5–50% by volume of the culture headspace. No organic additions such as yeast extract or vitamins are required to achieve growth shown in FIG. 1. FIG. 1 shows the growth of 16a compared to the growth of *Methylococcus capsulatus* under identical growth conditions. i.e. minimal medium with 25% methane in air as substrate. The data indicates *Methylomonas* 16a doubles every 2–2.5 h whereas *Methylococcus capsulatus* doubles every 3.5 h with methane as substrate. With methanol as substrate doubling times on methanol are 2.5–3 h for *Methylomonas* 16a and 4.5–5 h for *Methylococcus capsidatus.* Cell densities are also significantly higher for *Methylomonas* 16a growing on methane. *Methylococcus capsulatus* is a widely utilized methanotroph for experimental and commercial purposes.

Example 3

Methanol Tolerance

*Methylomonas* 16a was grown on defined medium with nitrate as sole nitrogen source and methanol as sole carbon source. Growth was monitored over a 36 hr period which was typically sufficient for attaining maximum optical density or turbidity of the culture. FIG. 2 clearly shows that maximum growth or turbidity is attained within 36 hours at methanol concentrations up to 600 mM. However no growth was observed at 800 mM. Therefore the strain is shown to grow on 2.4% (vol/vol) of methanol.

Example 4

Properties and Classification of *Methylomonas* 16a

Table 2 shows the various properties of *Methylomonas* 16a. The criteria listed in Table 2 are those typically used to determine whether the strain is arbitrarily considered Type I, Type II or Type X based on physical and enzymatic properties. This table was developed from both direct enzymatic assay for enzymes as well as genomic data showing the presence of genes and gene pathways. This categorization is functionally based and indicates that the strain utilizes the most energetically efficient pathway for carbon incorporation which is the ribulose monophosphate or "RuMP" pathway. Genomic data clearly shows the presence of key enzymes in the RuMP pathway. Internal membrane structure are also indicative of a Type I physiology. Unique to the present strain is the finding of nitrogen fixation genes in *Methylomonas* 16a. The strain is shown to grow in the absence of yeast extract or vitamins. Nitrate, ammonium ion or dinitrogen can satisfy the nitrogen requirement for biosynthesis. This functional data is in complete agreement with the 16srRNA homologies as compared with other *Methylomonas* strains. 16sRNA comparisons or the 16a strain (SEQ ID NO:81) with other *Methylomonas* sp. revealed that *Methylomonas* 16a has 96% identity with the 16sRNA of *Methylomonas* sp. (strain:KSPIII) [Hanada, S et al., *J. Ferment. Bioeng.* 86, 539–544 (1998)] and with *Methylomonas* sp. (strain LW13), [Costello, A. M. and Lidstrom, M. E. *Appl. Environ. Microbiol.* 65 (11), 5066–5074 (1999)]]. Thus *Methylomonas* 16a is correctly classified as a Type I, RuMP utilizing, *Methylomonas* species.

TABLE 2

| Characteristic | Type I | Methylomonas 16a | Type X | Type II |
|---|---|---|---|---|
| % GC | Incomplete | Incomplete | Incomplete | Complete |
| Ribmp Cycle | Incomplete | Incomplete | Incomplete | Complete |
| RuBP Carboxylase | – | – | + | + |
| Temp. Range | <45° C. | <42° C. | <45° C. | <40° C. |
| Nitrogenase | – | + | + | + |
| G6P dehydrogenase NADP | + | + | + | – |
| Isocitrate dehydrogenase | + | + | – | – |

TABLE 2-continued

| Characteristic | Type I | Methylomonas 16a | Type X | Type II |
|---|---|---|---|---|
| NAD/NADP | | | | |
| Yeast Extract | – | – | – | – |
| Vitamins | – | – | – | – |
| Pigmentation | Variable | + | Variable | Variable |
| Nitrate assimilation | + | + | + | + |

Method of Enzymatic Assay

Nitrogenase was not assayed but is considered positive if the gene is present on the basis of genome sequence analysis.

Glucose 6 phosphate dehydrogenase: One mL of reaction mixture contains 100 μL of 10 mM NADP, 100 μL of 10 mM glucose, 700 μL of 100 mM HEPES pH 7 buffer and up to 100 μL of enzyme extract. The enzyme activity was measured by monitoring NADP reduction to NADPH at 340 nm using spectrophotometer.

Isocitrate dehydrogenase: One mL of reaction mixture contains 100 μL of 10 mM sodium isocitrate, 100 μL of 10 mM NADP, 700 μL of 100 mM pH 7 HEPES buffer up to 100 μL of enzyme extract. The enzyme activity was measured by monitoring NADPH formation at 340 nm.

Nitrate assimilation is based on the ability of the strain to grow on nitrate as sole nitrogen source.

The results of the enzyme assay are sown in Table 2.

Example 5

Comparison of Gene Expression Levels in the Entner Douderoff Pathway as Compared with the Embeden Meyerhof Pathway Example 5 presents microarray evidence for the use of the Embden-Meyerhof pathway in the 16a strain.

FIG. 3 shows the relative levels of expression of genes for the Entner-Douderoff pathway and the Embden-Meyerhof pathway. The relative transcriptional activity of each gene was estimated with DNA microarray as described previously (Wei, et al., 2001. *Journal of Bacteriology.* 183:545–556).

Specifically, a single DNA microarray containing 4000 ORFs (open reading frames) of *Methylomonas* sp. strain 16a was hybridized with probes generated from genomic DNA and total RNA. The genomic DNA of 16a was labeled with Klenow fragment of DNA polymerase and fluorescent dye Cy-5, while the total RNA was labeled with reverse transcriptase and Cy-3. After hybridization, the signal intensities of both Cy-3 and Cy-5 for each spot in the array were quantified. The intensity ratio of Cy-3 and Cy-5 was then used to calculate the fraction of each transcript (in percentage) with the following formula: (gene ratio/sum of all ratio)×100. The value obtained reflects the relative abundance of mRNA of an individual gene. Accordingly, transcriptional activity of all the genes represented by the array can be ranked based on its relative mRNA abundance in a descending order. For example, mRNA abundance for the methane monooxygenase was ranked #1 because its genes had the highest transcriptional activity when the organism was grown with methane as the carbon source (FIG. 3).

The genes considered "diagnostic" for Entner-Douderoff are the 6 phosphogluconate dehydratase and the 2 keto-3-deoxy-6-phosphogluconate aldolase. Phosphofructokinase and fructose bisphosphate aldolase are "diagnostic" of the Embden-Meyerhof sequence. Numbers in FIG. 3 next to each step indicate the relative expression level of that enzyme. For example the most highly expressed enzyme in the cell is the methane monooxygenase (ranked #1). The next most highly expressed is the methanol dehydrogenase (ranked #2). Messenger RNA transcripts of Phosphofructokinase (ranked #232) and fructose bisphosphate aldolase (ranked #65) were in higher abundance than those for glucose 6 phosphate dehydrogenase (ranked #717), 6 phosphogluconate dehydratase (ranked #763) or the 2-keto-3-deoxy-6-gluconate aldolase. The data suggests that the Embden-Meyerhof pathway enzymes are more strongly expressed than the Entner-Douderoff pathway enzymes. This result is surprising and counter to existing beliefs on the central metabolism of methanotrophic bacteria (Reference book pages in. The physiology and biochemistry of aerobic methanol-utilizing gram-negative and gram-positive bacteria In: Methane and Methanol Utilizers, Biotechnology Handbooks 5. 1992. Eds: Colin Murrell, Howard Dalton. Pp 149–157.

Example 6

Direct Enzymatic Evidence for a Pyrophosphate-Linked Phosphofructokinase

Example 6 shows the evidence for the presence of a pyrophosphate-linked phosphofructokinase enzyme in the current strain which would confirm the functionality of the Embden-Meyerhof pathway in the present strain.

Phosphofructokinase activity was shown to be present in *Methylomonas* 16a by using the coupled enzyme assay described below. Assay conditions are given in Table 3 below. This assay was further used to assay the activity in a number of other Methanotrophic bacteria as shown below in Table 4. The data in Table 4 show known ATCC strains tested for phosphofructokinase activity with ATP or pyrophosphate as phosphoryl donor. These organisms were classified as either Type I or Type X ribulose monophosphate-utilizing strains or Type II serine utilizer.

Coupled Assay Reactions

Phosphofructokinase reaction is measured by a coupled enzyme assay. Phosphofructokinase reaction is coupled with fructose 1,6, biphosphate aldolase followed by triosephosphate isomerase. The enzyme activity is measured by the disappearance of NADH.

Specifically, the enzyme phosphofructokinase catalyzes the key reaction converting Fructose 6 phosphate and pyrophosphate to Fructose 1,6 bisphosphate and orthophosphate.

Fructose-1,6-bisphosphate is cleaved to 3-phosphoglyceraldehyde and dihydroxyacetonephosphate by fructose 1,6-bisphosphate aldolase.

Dihydroxyacetonephosphate is isomerized to 3-phosphoglyceraldehyde by triosephosphate isomerase.

Glycerol phosphate dehydrogenase plus NADH and 3-phosphoglyceraldehyde yields the alcohol glycerol-3-phosphate and NAD. Disappearance of NADH is monitored at 340 nm using spectrophotometer (UltraSpec 4000, Pharmacia Biotech).

TABLE 3

Assay Protocol

| Reagent | Stock solution (mM) | Volume (μl) per 1 mL total reaction volume | Final assay concentration (mM) |
|---|---|---|---|
| Tris-HCl pH 7.5 | 1000 | 100 | 100 |
| $MgCl_2.2\ H_2O$ | 100 | 35 | 3.5 |

TABLE 3-continued

Assay Protocol

| Reagent | Stock solution (mM) | Volume (μl) per 1 mL total reaction volume | Final assay concentration (mM) |
|---|---|---|---|
| $Na_4P_2O_7.10H_2O$ or ATP | 100 | 20 | 2 |
| Fructose-6-phophate | 100 | 20 | 2 |
| NADH | 50 | 6 | 0.3 |
| Fructose bisphosphate aldolase | 100 (units/mL) | 20 | 2 (units) |
| Triose phosphate isomerase/glycerol phosphate dehydrogenase | (7.2 units/μl) (0.5 units/μl) | 3.69 | 27 units 1.8 units |
| KCl | 1000 | 50 | 50 |
| H2O | | adjust to 1 mL | |
| Crude extract | | 0–50 | |

TABLE 4

Comparison Of Pyrophosphate Linked And ATP Linked Phosphofructokinase Activity In Different Methanotrophic Bacteria

| Strain | Type | Assimilation Pathway | ATP-PFK umol NADH/ min/mg | Ppi-PFK umol NADH/ min/mg |
|---|---|---|---|---|
| *Methylomonas* 16a ATCC PTA 2402 | I | Ribulose monophosphate | 0 | 2.8 |
| *Methylomonas agile* ATCC 35068 | I | Ribulose monophosphate | 0.01 | 3.5 |
| *Methylobacter Whittenbury* ATCC 51738 | I | Ribulose monophosphate | 0.01 | 0.025 |
| *Methylomonas clara* ATCC 31226 | I | Ribulose monophosphate | 0 | 0.3 |
| *Methylomicrobium albus* ATCC 33003 | I | Ribulose monophosphate | 0.02 | 3.6 |
| *Methylococcus capsulatus* ATCC 19069 | X | Ribulose monophosphate | 0.01 | 0.04 |
| *Methylosinus sporium* ATCC 35069 | II | Serine | 0.07 | 0.4 |

Several conclusions may be drawn from the data presented above. First, it is clear that ATP (which is the typical phosphoryl donor for phosphofructokinase) is essentially ineffective in the phosphofructokinase reaction in methanotrophic bacteria. Only inorganic pyrophosphate was found to support the reaction in all methanotrophs tested. Secondly not all methanotrophs contain this activity. The activity was essentially absent in *Methylobacter whittenbury* and in *Methylococcus capsulatus*. Intermediate levels of activity were found in *Methylomonas clara* and *Methylosinus sporium*. These data show that many methanotrophic bacteria may contain a hitherto unreported phosphofructokinase activity. It may be inferred from this that methanotrophs containing this activity have an active Embden-Meyerhof pathway.

Example 7

Growth Yield and Carbon Conversion by *Methylomonas* 16a

Growth yield and carbon conversion efficiency were compared for *Methylomonas* 16a and *Methylococcus capsulatus*. These strains were chosen because 16a contains high levels of phosphofructokinase and *M. capsulatus* is essentially devoid of the enzyme activity. It was contemplated that if *Methylomonas* 16a could utilize the more energetically favorable Embden-Meyerhof pathway and *Methylococcus capsulatus* could only use the Entner-Douderoff pathway the superior energetics of the present *Methylomonas* 16a strain would be reflected in cellular yields and carbon conversion efficiency. This difference in energetic efficiency would only be apparent under energy-limiting conditions. These conditions were achieved in this experiment by limiting the amount of oxygen in each culture to only 10% (vol/vol) instead of 20% (growth conditions employed in FIG. 1 and Table 9). Under these oxygen limiting conditions the strain that produces the most energy from aerobic respiration on methane will produce more cell mass.

Cells were grown as 200 mL cultures 500 mL serum-stoppered Wheaton bottles. The headspace in the bottles was adjusted to 25% methane and 10% oxygen. The defined medium formulation is the same in both cases.

TABLE 5

Yield Of Methylomonas 16a Cells Versus Methylococcus Capsulatus Cells Under Oxygen Limitation.

| Strain | $Y_{CH4\ g\ dry\ wt/mol}$ | G dry wt/g $CH_4$ | Carbon Conversion Efficiency (CCE) % |
|---|---|---|---|
| *Methylomonas* 16a | 16.7 +/− 0.5 | 1.04 | 64 |
| *Methylococcus capsulatus* | 10.3 +/− 0.3 | 0.64 | 40 |

Yield determination: Yield was measured by growing triplicate cultures in 500 mL bottles on defined medium with ammonium as nitrogen source under oxygen limitation. This was done by using 300 mL of culture with a 300 mL headspace of 25% methane and 10% oxygen the balance being nitrogen. At the end of growth (i.e. stationary phase) residual methane in the headspace was determined by gas chromatography. The cells were collected by centrifugation washed with distilled water and dried overnight in a drying oven before being weighed.

Carbon conversion efficiency is a measure of how much carbon is assimilated into cell mass. It is calculated assuming a biomass composition of $CH_2O_{0.5}N_{0.25}$:

*Methylomonas* 16a: 16 g/mol methane×(1 g dry wt/g methane)/25 g/mol biomass

*M. capsulatus* 16 g/mol methane×(0.64 g dry wt/g methane)/25 g/mol biomass

These data (in Table 5) show that *Methylomonas* 16a produced significantly more cell mass than did the *Methylococcus capsulatus* strain under growth conditions that were identical except for the temperature. *Methylococcus capsulatus* grows optimally at 45° C. whereas *Methylomonas* is grown at 33° C. It may be inferred from the data that the presence of the more energy-yielding Embden-Meyerhof pathway confers a growth advantage to *Methylomonas* 16a.

Table 6 presents the theoretical calculations showing ATP yield as a function of carbon assimilation pathway with the carbon output being normalized to pyruvate in all cases (The physiology and biochemistry of aerobic methanol-utilizing gram-negative and gram-positive bacteria In: Methane and Methanol Utilizers, Biotechnology Handbooks 5.1992. Eds: Colin Murrell, Howard Dalton. Pp. 149–157). Table 6 shows the amount of ATP that is produced or consumed for every three molecules of carbon (as formaldehyde or carbon dioxide) for serine cycle, xylulose monophosphate cycle and ribulose monophosphate cycle pathways. The latter pathway, as discussed is typically thought to exist as the 2-keto-3deoxy-6-phosphogluconate/transaldolase (KDPGA/TA) variant. These data shows that in fact the fructose bisphosphate aldolase/transaldolase (FBPA/TA) variant is likely to exist in the methanotrophs. The energetic repercussion of this is the net production of an additional 1 ATP for methanotrophs if they possess an ATP linked phosphofructokinase and an additional 2 ATPs for the pyrophosphate-linked enzyme. It is therefore expected that *Methylomonas* 16a derives and additional 2 ATP per 3 carbons assimilated and that this may explain the greater yield and carbon efficiency of the strain versus *Methylococcus capsulatus*.

TABLE 6

Energetics of Methanotrophic bacteria utilizing different carbon assimilation mechanisms

| Organism | Cycle | C1 unit fixed | Product | Variant | ATP | NADPH |
|---|---|---|---|---|---|---|
| Bacteria | RuMP | $3CH_2O$ | Pyruvate | FBPA/TA | +1 | +1 |
| *Methylomonas* | RuMP/Serine | $3CH_2O$ | Pyruvate | FBPA/TA | +1(+2*) | +1 |
| Bacteria | RuMP | $3CH_2O$ | Pyruvate | KDPGA/TA | 0 | +1 |
| *Methylococcus* | RuMP/RuBP | $3CH_2O$ | Pyruvate | KDPGA/TA | 0 | +1 |

*Based on PPi dependent phosphofructokinase

Example 8

Nitrate/Nitrite Spares Oxygen

Figure 4:
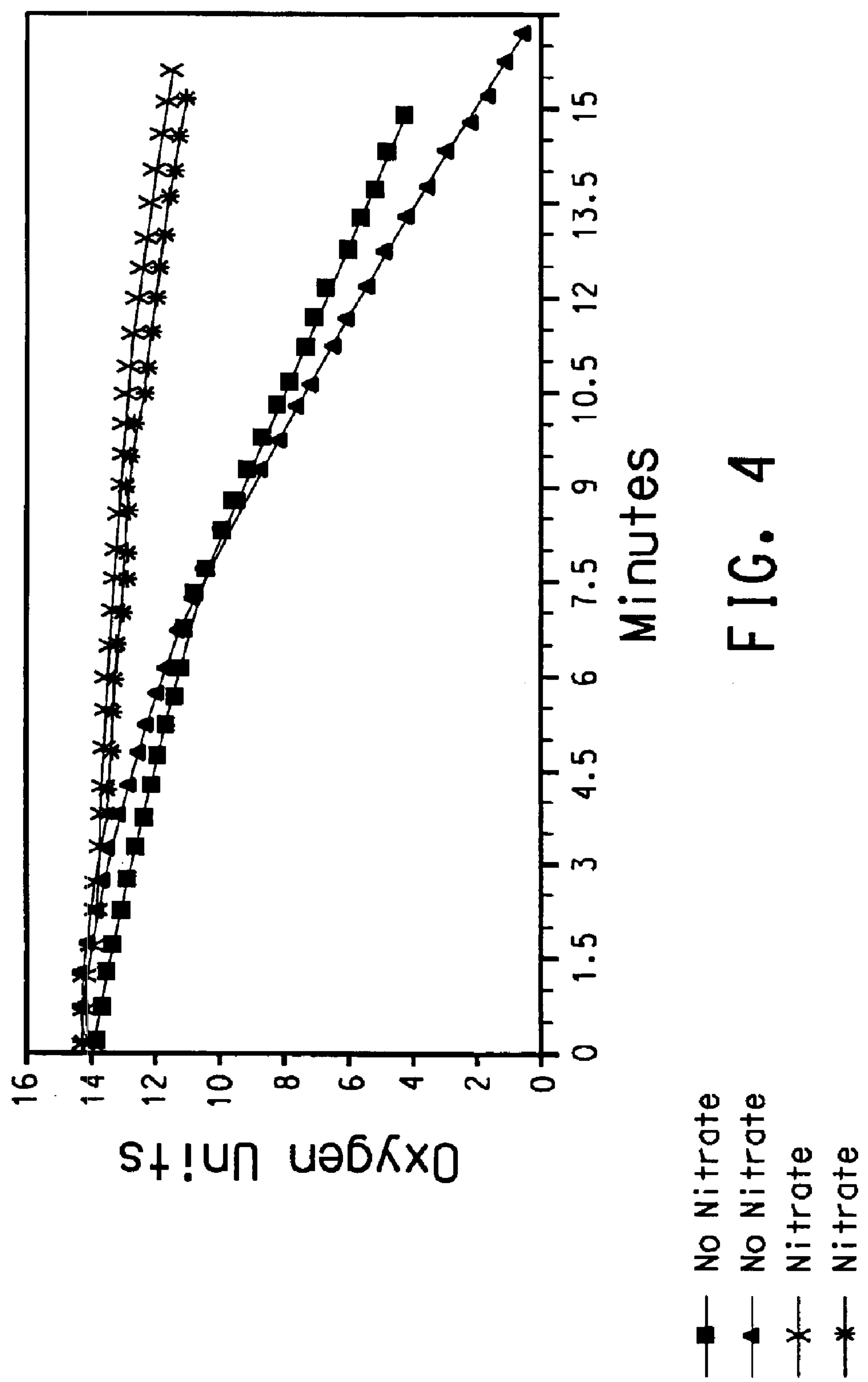
FIG. 4 shows oxygen uptake by a cell suspension of *Methylomonas* 16a, in arbitrary units to detect oxygen consumption.

FIG. 4 shows oxygen uptake by a cell suspension of *Methylomonas* 16a, in relative detector units, using an Orion oxygen probe (Orion, UK) to detect oxygen consumption. Oxygen was measured as a function of time in the presence or absence of nitrate and in the presence of methanol as electron donor and carbon source. The incubation consisted of *Methylomonas* 16a cells suspended in HEPES buffer pH 7. Methanol was injected at 3 min into both incubations to achieve a final concentration of about 100 mM. After the methanol injection it can be seen that oxygen uptake accelerated as would be expected (FIG. 4) in the cultures without nitrate. However the rate of oxygen uptake in the presence of nitrate never approaches that of cells without nitrate. The data thus supports the finding that nitrate can spare oxygen consumption with methanol as carbon source.

Figure 5:
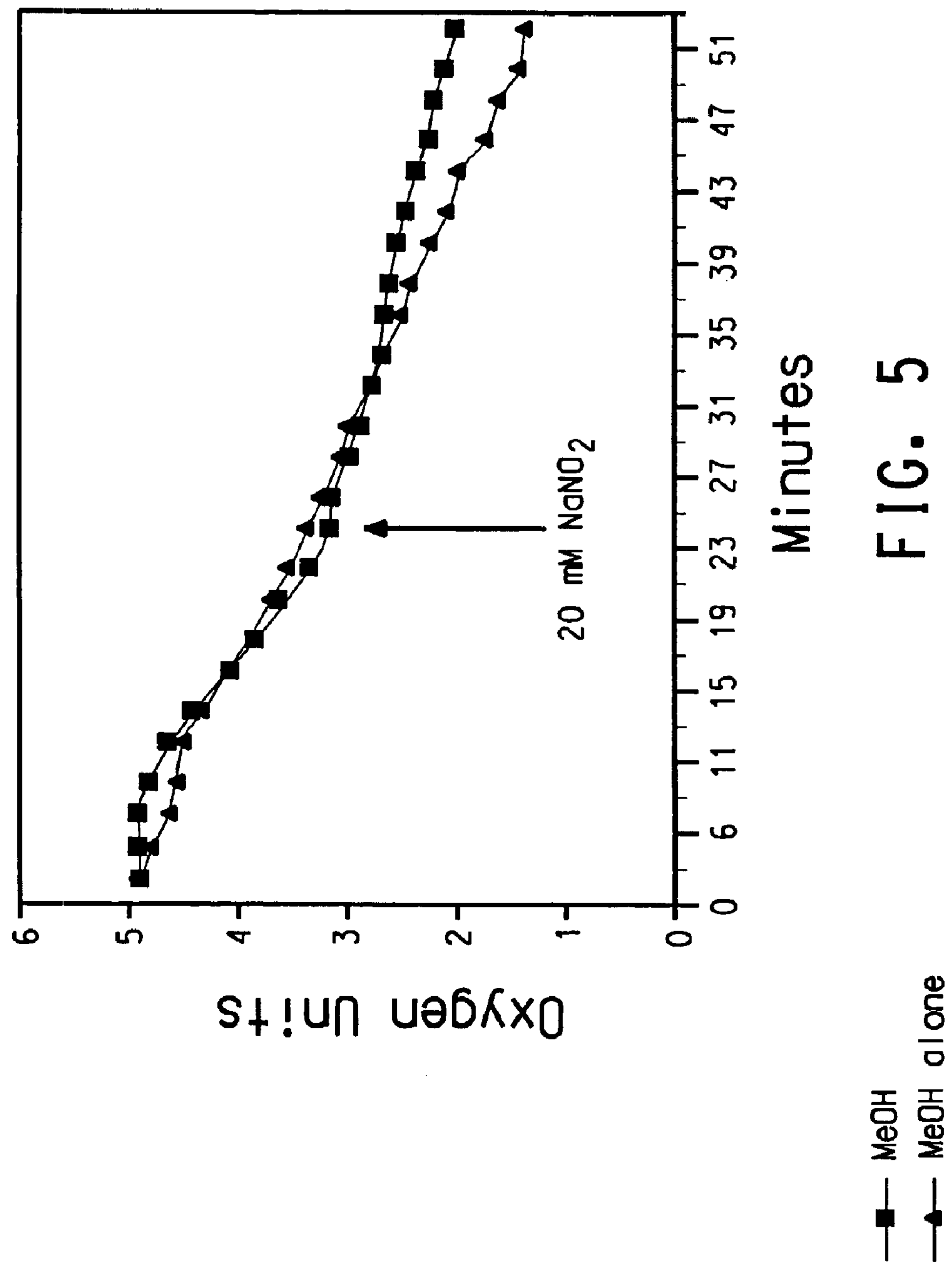
FIG. 5 shows oxygen uptake by a cell suspension of *Methylomonas* 16a, in arbitrary units to detect oxygen consumption before and after sodium nitrite was injected into the incubation.

*Methylomonas* 16a cells were again suspended in HEPES buffer pH 7 and incubated in a water jacketed chamber equipped with an Orion oxygen probe. The incubation was carried out at 30° C. Methanol was injected into the incubation at 1 min. However in one incubation sodium nitrite (25 mM) was injected into the incubation after 23 min. The results are shown in FIG. 5. As seen in FIG. 5, there is a decrease in the rate of oxygen uptake after the addition of nitrite. This data again clearly supports the assertion that nitrite and indirectly nitrate can be used as an alternative electron sink and resulting in less oxygen consumption by the culture.

Figure 6:
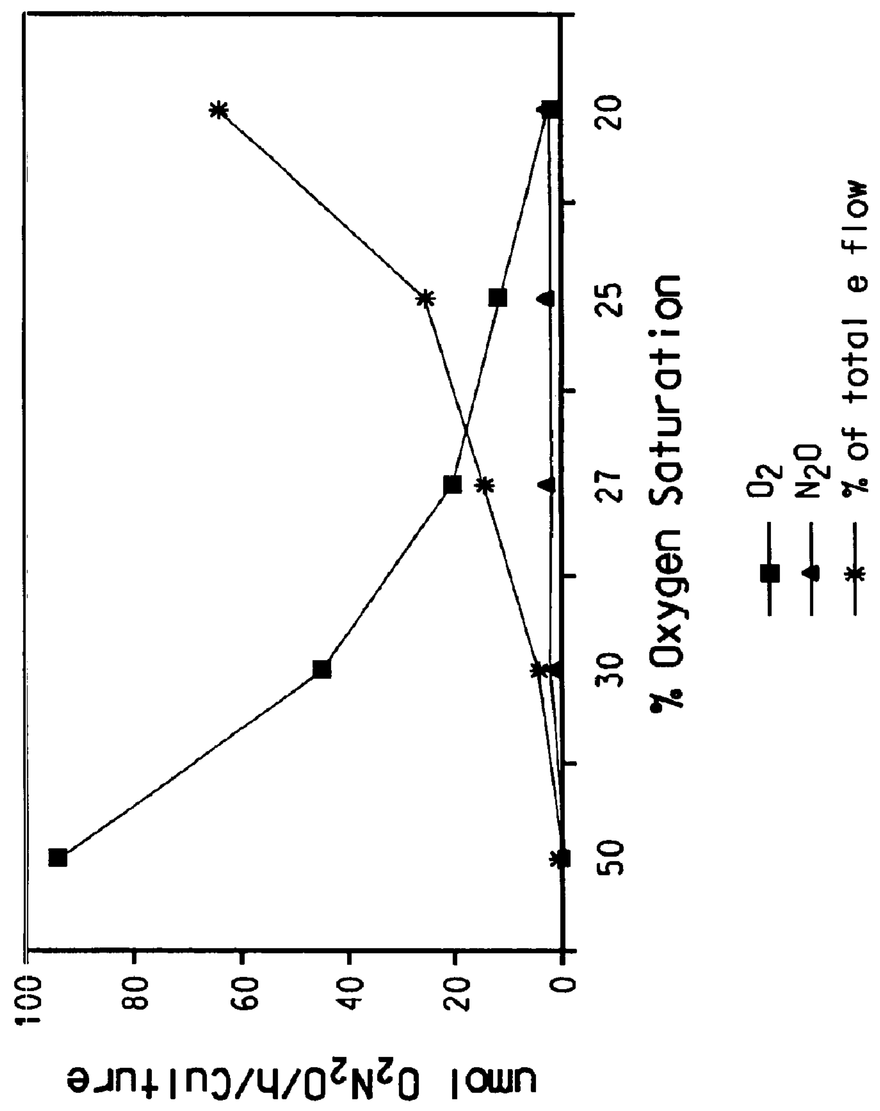
FIG. 6 is a plot of the concentration of $O_2$ and $N_2O$ evolved per hour vs. the concentration of $O_2$ in the medium of a cell suspension of *Methylomonas* 16a under aerobic conditions.

A cell suspension of *Methylomonas* 16a in defined medium under 25% methane in air was simultaneously monitored for oxygen and $N_2O$ in the dead-space. 100 mM Nitrite was the only added source of nitrogen. The results are shown in FIG. 6. FIG. 6 illustrates that the appearance of $N_2O$ in the dead-space coincides with oxygen depletion. The numbers plotted are the rates of appearance or disappearance of $N_2O$ and oxygen respectively. As oxygen disappearance rates decline to lower values (due to lower headspace $O_2$ concentrations) $N_2O$ production increases to become a significant fraction of the total electron flow through the organism (only under oxygen limitation).

Example 9

Nitrate or Nitrite Reduction by Other Strains of Methanotrophs and *Methylomonas* 16a All methanotrophic strains available from the American Type Culture collection were tested for their ability to produce $N_2O$ from nitrite or nitrate. All strains were grown on the defined medium and harvested after an optical density at 660 nm of 1.0 was achieved. The cell suspensions were collected by centrifugation and resuspended in 5 mL of defined medium with either nitrate or nitrite as sole nitrogen source. The data in Table 7 below shows the accumulation of $N_2O$ (in uM concentration) in the headspace of a 10 mL assay vial incubated 30° C. The results shows that *Methylomonas* 16a has a unique ability to convert nitrate to $N_2O$ among the strains tested. Furthermore the data show that two other *Methylomonas* strains have a similar ability to convert nitrite to $N_2O$.

TABLE 7

| STRAIN | $NO_3/NO_2$ uM | $NO_2/N_2O$ uM |
|---|---|---|
| *Methylomonas* 16a | 28.3 | 30 |
| *Methylomonas albus* | 1.2 | 22 |
| *Methylomonas clara* | 2.5 | 1.5 |
| *Methylomonas agile* | 0.6 | 17 |
| *Methylobacter whitterbury* | 0.3 | 0.04 |
| *Methylococcus capsulatis* | 0.3 | 1.9 |
| *Methylobacter lutes* | 0.1 | 6.5 |
| *Methylosinus sporium* | 0.2 | 0.07 |

Example 10

Production of Glycogen

*Methylomonas* 16a was shown to accumulate large amounts of glycogen when grown on either methane or methanol. *Methylomonas* cells were analyzed for glycogen using a starch assay kit (Sigma Chemical Co. St Louis Mo.). This assay is starch or glycogen specific and conclusively shows the presence of glycogen in *Methylomonas* 16a. Cells were grown according to the conditions outlined in the General Methods, Cells were harvested during growth on 100 mM methanol or 25% headspace methane at 30° C. on defined medium. Culture samples were taken at two points in the growth curve: mid-logarithmic growth (O.D. 660 0.3) and stationary phase (O.D. 660 1.0). These samples were immediately analyzed with the starch assay kit according to the manufacturers instructions. The results shown below in Table 8 indicate surprising amounts of the storage polymer during growth on methanol and lower but significant amounts of glycogen during growth on methane.

TABLE 8

| Growth Phase (OD660) | Methane (% glycogen wt/wt) | Methanol (% glycogen (wt/wt) |
|---|---|---|
| Mid-log (0.3) | 6% | 25% |
| Stationary phase (1.0) | 7% | 40% |

Additionally, the presence of granules within the cells grown on methanol were observed by scanning electron microscopy and the granules were determined to contain starch with polysaccharide specific stains.

Example 11

Production of Protein from Cell Mass

*Methylomonas* 16a and *Methylococcus capsulatus* (reference strain for protein production) were grown on defined medium until no further increases in OD 660 could be observed. Methane or methanol consumption was monitored by gas chromatography (HP-Plot Molecular sieve column; Hewlett Packard 5890 series II gas chromatograph) over the growth curve such that the total amount of methane or methanol consumed could be calculated. The running conditions for GC were; oven temperature: 40° C., initial temperature: 40° C., initial time: 3 min, rate: 0 deg/min, final temperature 40° C., final time 0, injection A temperature: 100° C., Det. A temperature: 125° C., and equilibration time: 0.

The cells were collected by centrifugation and dried overnight in a 105° C. drying oven. The data in Table 9 below shows the gram dry weight of cells produced per gram of methane or methanol consumed.

TABLE 9

| Organism | g dry wt./g $CH_4$ | g dry wt./g $CH_3OH$ |
|---|---|---|
| *Methylomonas* 16a | 0.90–1.3 (2–2.5 hr) | 0.30–0.45 (2.5–3.0 hr) |
| *Methylococcus capsulatus* | 0.67–1.2 (3–4 hr) | 0.25–0.45 (4–5 hr) |

As can be seen by the data in Table 9 the present strain has a higher rate of protein production than the commercial methanotroph of choice for this process, when grown on either methane or methanol.

Example 12

Production of Extracellular Polysacharride

*Methylomonas* 16a cells were grown on 25% methane in 200 mL batch culture on defined medium at 30° C. Initial oxygen concentration was varied by injecting pure oxygen into nitrogen flushed bottles. Cells were allowed to grow until stationary phase or to an optical density of approximately 1.0. At that time the cultures were centrifuged at 6000×g for 30 min to sediment both the cells and the extracellular polysaccharide. The sediments from these centrifugations comprised two layers. At the bottom were the cells, overlaid with a clear viscous material which was the extracellular polysaccharide (EPS). The EPS layer was washed off and pelleted again for further separation from the cells. The cell pellet was also dried and weighed. The EPS was resuspended in 50% ethanol and pelleted again in the centrifuge. Finally the material was dried and weighed. EPS was found to comprise as much as 50% of the total dry weight of the culture at near-ambient oxygen concentrations. This was determined by centrifugation of the culture at 10,000×g for 30 min. The resulting pellet is comprised of a lower red phase (packed cells) and an upper translucent phase which is the extracellular polysaccharide. The EPS was selectively removed with a spatula and dried at 105° C. overnight. The cell pellet was removed and dried at 105° C. overnight. The supernatant from the centrifugation was mixed with cold isopropanol (1:1 vol:vol). The precipitated EPS from this step was collected by centrifugation (10, 000×g for 30 min) and the pellet dried at 105° C. overnight and weighed. Chemical analysis of the EPS revealed that it was primarily polyglucose (~70%). EPS samples were methylated by the method of Ciucanu, I., F. Kerek. 1984. *Carbohydrate Research* 131:209–217. The methylated samples were hydrolyzed in 2 M TFA at 121° C. for 2 hours and the hydrolyzed carbohydrate was reduced with sodium borodeuteride at room temperature. The product was acetylated by GC-MS using Sp2330 Supelco column. Internal standard myo-inositol was added to each sample prior to the reduction step.

What is claimed is:

1. A method for the production of cellular biomass comprising protein, carbohydrates, and pigment comprising the steps of:

(a) providing a high growth methanotrophic bacterial strain which:

(1) grows on a C1 carbon substrate selected from the group consisting of methane and methanol; and (2) comprises a functional Embden-Meyerhof carbon patahway, said pathway comprising a gene encoding a pyrophosphate dependent phosphofructokinase enzyme as set forth in SEQ ID NO: 6;

(b) contacting the bacterial strain of (a) with a C1 carbon substrate in a suitable medium for a time sufficient to permit the expression and accumulation of the cellular biomass; and (c) optionally recovering the cellular biomass.

* * * * *

SEQUENCE LISTING

```
<160> NUMBER OF SEQ ID NOS: 81

<210> SEQ ID NO 1
<211> LENGTH: 1434
<212> TYPE: DNA
<213> ORGANISM: METHYLOMONAS SP.

<400> SEQUENCE: 1

aacatgcaaa taaaaaccta taagaccaca ccctatgatg atcaaaaacc cggcacatcc      60

gggctaagaa aaaaggttaa agtttttcag caatccggct atctggaaaa tttcgttcag     120
```

-continued

```
tccattttca atagtttaga agattttcag ggaaaaattc tagttttagg cggcgacggc    180

cgatatttta atcgacaagc gattcagatc atcatcaaaa tggcggccgc taacgggttt    240

ggtgagctga tcatcggcca gggcggtctg ttgtcgacac cggcggcctc caatgtcatc    300

cgcaaatatc gcgctttcgg cggcatcatt ctatccgcca gccacaatcc cggtggtccc    360

gacgaagact tcggcatcaa atataacgtc ggcaatggcg ggccggcacc ggaaaagttc    420

accgacgcct tgttcgaaaa cagcaaaacc atcaccagct atcagatggc cgaaatcgac    480

gacatcgatc tcgatagcgt cggcgacgtc caaatcgatg gcataacaat ccgcatcatc    540

gatcccgtgg ccgattacgc cgaattgatg gcccggattt tcgatttcga cctgatcaag    600

caaagcatcg ccgccggctt gattaccttg cgcttcgacg cgatgcatgc cattaccggc    660

ccctatgcca aacatatact cgaagacgtg ctgggcgccg cgcccggttc ggtattcaac    720

gccgtaccgc tggaagactt cggcggcggc catcccgatc ccaacatggc gcacgcgcac    780

gagctcaccg aaatcatgtt cgggccgaat ccgccggttt tcggcgcggc ctcggacggt    840

gacggcgacc gcaacatgat catgggcgcc aatattttcg tcacccccag cgacagtctg    900

gccatcatgg cggccaacgc gcaattgatt cccgcctatg ccaagggcat tagcggcgtc    960

gcccgctcga tgccgaccag ccaggcggtc gacagggtcg cggataaatt gagtctgccg   1020

tgctacgaaa cgccgaccgg ctggaaattc tttggcaatt tgctggatgc cgacaaaatc   1080

acgctgtgcg gcgaagaaag cttcggttcc ggttccaatc atgtccggga aaaagacggc   1140

ttgtgggccg ttttattttg gctgaatttg cttgcgcgca agcgtcaacc ggccgaggat   1200

atcgtgcgtg aacattggca aaaatacggc cgcgacatct attgccgcca tgattacgaa   1260

gccgtcgatg ccgacatcgc caacggcatc gtagagcagc tgcgaaacca attgccgagc   1320

ttgcccggca aaacctgggg cgattacagc gtcaaattcg ccgacgaatt cagctatacc   1380

gatccggtcg atggtagcgt cagcagcaac caaggcatcc gcgtcggttt cgcc         1434
```

<210> SEQ ID NO 2
<211> LENGTH: 545
<212> TYPE: PRT
<213> ORGANISM: METHYLOMONAS SP.

<400> SEQUENCE: 2

```
Asn Met Gln Ile Lys Thr Tyr Lys Thr Thr Pro Tyr Asp Asp Gln Lys
  1               5                  10                  15

Pro Gly Thr Ser Gly Leu Arg Lys Lys Val Lys Val Phe Gln Gln Ser
             20                  25                  30

Gly Tyr Leu Glu Asn Phe Val Gln Ser Ile Phe Asn Ser Leu Glu Asp
         35                  40                  45

Phe Gln Gly Lys Ile Leu Val Leu Gly Gly Asp Gly Arg Tyr Phe Asn
     50                  55                  60

Arg Gln Ala Ile Gln Ile Ile Ile Lys Met ala Ala Ala Asn Gly Phe
 65                  70                  75                  80

Gly Glu Leu Ile Ile Gly Gln Gly Gly Leu Leu Ser Thr Pro Ala Ala
                 85                  90                  95

Ser Asn Val Ile Arg Lys Tyr Arg Ala Phe Gly Gly Ile Ile Leu Ser
            100                 105                 110

Ala Ser His Asn Pro Gly Gly Pro Asp Glu Asp Phe Gly Ile Lys Tyr
        115                 120                 125

Asn Val Gly Asn Gly Gly Pro Ala Pro Glu Lys Phe Thr Asp Ala Leu
    130                 135                 140
```

```
Phe Glu Asn Ser Lys Thr Ile Thr Ser Tyr Gln Met ala Glu Ile Asp
145                 150                 155                 160

Asp Ile Asp Leu Asp Ser Val Gly Asp Val Gln Ile Asp Gly Ile Thr
                165                 170                 175

Ile Arg Ile Ile Asp Pro Val Ala Asp Tyr Ala Glu Leu Met ala Arg
            180                 185                 190

Ile Phe Asp Phe Asp Leu Ile Lys Gln Ser Ile Ala Ala Gly Leu Ile
        195                 200                 205

Thr Leu Arg Phe Asp Ala Met His Ala Ile Thr Gly Pro Tyr Ala Lys
    210                 215                 220

His Ile Leu Glu Asp Val Leu Gly Ala Ala Pro Gly Ser Val Phe Asn
225                 230                 235                 240

Ala Val Pro Leu Glu Asp Phe Gly Gly Gly His Pro Asp Pro Asn Met
                245                 250                 255

Ala His Ala His Glu Leu Thr Glu Ile Met Phe Gly Pro Asn Pro Pro
            260                 265                 270

Val Phe Gly Ala Ala Ser Asp Gly Asp Gly Asp Arg Asn Met Ile Met
        275                 280                 285

Gly Ala Asn Ile Phe Val Thr Pro Ser Asp Ser Leu Ala Ile Met ala
    290                 295                 300

Ala Asn Ala Gln Leu Ile Pro Ala Tyr Ala Lys Gly Ile Ser Gly Val
305                 310                 315                 320

Ala Arg Ser Met Pro Thr Ser Gln Ala Val Asp Arg Val Ala Asp Lys
                325                 330                 335

Leu Ser Leu Pro Cys Tyr Glu Thr Pro Thr Gly Trp Lys Phe Phe Gly
            340                 345                 350

Asn Leu Leu Asp Ala Asp Lys Ile Thr Leu Cys Gly Glu Glu Ser Phe
        355                 360                 365

Gly Ser Gly Ser Asn His Val Arg Glu Lys Asp Gly Leu Trp Ala Val
    370                 375                 380

Leu Phe Trp Leu Asn Leu Leu Ala Arg Lys Arg Gln Pro Ala Glu Asp
385                 390                 395                 400

Ile Val Arg Glu His Trp Gln Lys Tyr Gly Arg Asp Ile Tyr Cys Arg
                405                 410                 415

His Asp Tyr Glu Ala Val Asp Ala Asp Ile Ala Asn Gly Ile Val Glu
            420                 425                 430

Gln Leu Arg Asn Gln Leu Pro Ser Leu Pro Gly Lys Thr Trp Gly Asp
        435                 440                 445

Tyr Ser Val Lys Phe Ala Asp Glu Phe Ser Tyr Thr Asp Pro Val Asp
    450                 455                 460

Gly Ser Val Ser Ser Asn Gln Gly Ile Arg Val Gly Phe Ala Asn Gly
465                 470                 475                 480

Ser Arg Ile Val Phe Arg Leu Ser Gly Thr Gly Thr Val Gly Ala Thr
                485                 490                 495

Leu Arg Ile Tyr Leu Glu Arg Tyr Glu Arg Asp Val Arg Asn His Asp
            500                 505                 510

Gln Asp Pro Gln Val Ala Leu Ala Glu Leu Ile Glu Ile Ala Glu Gln
        515                 520                 525

Leu Cys Gln Val Lys Gln Arg Thr Gly Arg Thr Glu Pro Ser Val Ile
    530                 535                 540

Thr
545
```

```
<210> SEQ ID NO 3
<211> LENGTH: 1387
<212> TYPE: DNA
<213> ORGANISM: METHYLOMONAS SP.

<400> SEQUENCE: 3

ccgaaagcag gcaaaatcac ggttcatttt tttttgtcat ccgtcaaaga caatccttat     60

aatgaggtaa tcgttctcct cgctacatct ggcactaaag cttccgaaga ctctttatcc    120

ggttcacaca aaaataatat gtccaaatta atcaactctg ccgaatggaa cgccgtcaaa    180

caacatcatc aagaaattgc tggtaaattt tgcatgaaag aggcttttgc caaagatccc    240

cagcgtttcg ataaattctc cgtcaccttt aacgacatat tattagacta ttccaaaaac    300

ctgatcgacg agcgcaccat gcccttgctg atcgcattgg caaagcgggc agacttgcgc    360

gagaaaacgg aagcgatgtt ttccggctcc atcatcaaca ccaccgaaaa acgcgcggtt    420

ttgcataccg cgctgcgaaa ccgtagcaat acgcccgttt tcttccgcgg ccaggatgtc    480

atgccggaaa tcaacaaggt tctggcaaaa atgcgggttt tcgtggaaca ggtgcgttcg    540

ggccaatgga cgggctatag cggcaaggcc attaccgata tcgtcaacat cggcattggc    600

ggctcggatc tcggcccgaa aatggtcgac accgccttga cgccgtacgg caaaaacggc    660

ttaaaagcgc atttcgtatc caatgtcgat caaaccgaca tcgtcgaaac cctgaaaccg    720

ctcaatccgg aaaccacgct gttcctgatt tcatcgaaaa cgtttaccac gcaggaaacc    780

atgaccaatg cgcgctcggc acgtaactgg ttcatgaatg ccgcgcaaga tcccgcccat    840

atcaagaaac atttcatcgc catttccacc aacgaagaaa tggtcaagga attcggcatc    900

gacccggcga acatgttcga gttctgggac tgggtcggcg ggcgttattc gctctggtcg    960

gtcatcggca tgtcgatagc tttatatatc ggcatggaca atttcgaaga actgctgatg   1020

ggtgcgcact tggccgacga acatttccgc catgcgccct acgaggaaaa cattccggtc   1080

atcatgggct tgctcggcat ctggtacaac aacttcttcg aagcggaaac ctatgccatt   1140

ttgccgtatg cgcaatcctt gaaatatttt gccgattatt tccagcaagg cgacatggaa   1200

agcaacggca aaagcgcgac gatcaccggt gaaaaagtcg attacaacac gggccccatc   1260

atctggggac agcccggcac caatggtcag cacgccttct ttcaattgat tcaccaaggc   1320

accaaactgg ttcccggcga ttttctggcg gccgcgcaaa gtcagtatga tttaccggat   1380

caccacg                                                              1387


<210> SEQ ID NO 4
<211> LENGTH: 592
<212> TYPE: PRT
<213> ORGANISM: METHYLOMONAS SP.

<400> SEQUENCE: 4

Pro Lys Ala Gly Lys Ile Thr Val His Phe Phe Leu Ser Ser Val Lys
  1               5                  10                  15

Asp Asn Pro Tyr Asn Glu Val Ile Val Leu Leu Ala Thr Ser Gly Thr
             20                  25                  30

Lys Ala Ser Glu Asp Ser Leu Ser Gly Ser His Lys Asn Asn Met Ser
         35                  40                  45

Lys Leu Ile Asn Ser Ala Glu Trp Asn Ala Val Lys Gln His His Gln
     50                  55                  60

Glu Ile Ala Gly Lys Phe Cys Met Lys Glu Ala Phe Ala Lys Asp Pro
 65                  70                  75                  80
```

```
Gln Arg Phe Asp Lys Phe Ser Val Thr Phe Asn Asp Ile Leu Leu Asp
                85                  90                  95

Tyr Ser Lys Asn Leu Ile Asp Glu Arg Thr Met Pro Leu Leu Ile Ala
            100                 105                 110

Leu Ala Lys Arg Ala Asp Leu Arg Glu Lys Thr Glu Ala Met Phe Ser
        115                 120                 125

Gly Ser Ile Ile Asn Thr Thr Glu Lys Arg Ala Val Leu His Thr Ala
    130                 135                 140

Leu Arg Asn Arg Ser Asn Thr Pro Val Phe Phe Arg Gly Gln Asp Val
145                 150                 155                 160

Met Pro Glu Ile Asn Lys Val Leu Ala Lys Met Arg Val Phe Val Glu
                165                 170                 175

Gln Val Arg Ser Gly Gln Trp Thr Gly Tyr Ser Gly Lys Ala Ile Thr
            180                 185                 190

Asp Ile Val Asn Ile Gly Ile Gly Gly Ser Asp Leu Gly Pro Lys Met
        195                 200                 205

Val Asp Thr Ala Leu Thr Pro Tyr Gly Lys Asn Gly Leu Lys Ala His
    210                 215                 220

Phe Val Ser Asn Val Asp Gln Thr Asp Ile Val Glu Thr Leu Lys Pro
225                 230                 235                 240

Leu Asn Pro Glu Thr Thr Leu Phe Leu Ile Ser Ser Lys Thr Phe Thr
                245                 250                 255

Thr Gln Glu Thr Met Thr Asn Ala Arg Ser Ala Arg Asn Trp Phe Met
            260                 265                 270

Asn Ala Ala Gln Asp Pro Ala His Ile Lys Lys His Phe Ile Ala Ile
        275                 280                 285

Ser Thr Asn Glu Glu Met Val Lys Glu Phe Gly Ile Asp Pro Ala Asn
    290                 295                 300

Met Phe Glu Phe Trp Asp Trp Val Gly Gly Arg Tyr Ser Leu Trp Ser
305                 310                 315                 320

Val Ile Gly Met Ser Ile Ala Leu Tyr Ile Gly Met Asp Asn Phe Glu
                325                 330                 335

Glu Leu Leu Met Gly Ala His Leu Ala Asp Glu His Phe Arg His Ala
            340                 345                 350

Pro Tyr Glu Glu Asn Ile Pro Val Ile Met Gly Leu Leu Gly Ile Trp
        355                 360                 365

Tyr Asn Asn Phe Phe Glu Ala Glu Thr Tyr Ala Ile Leu Pro Tyr Ala
    370                 375                 380

Gln Ser Leu Lys Tyr Phe Ala Asp Tyr Phe Gln Gln Gly Asp Met Glu
385                 390                 395                 400

Ser Asn Gly Lys Ser Ala Thr Ile Thr Gly Glu Lys Val Asp Tyr Asn
                405                 410                 415

Thr Gly Pro Ile Ile Trp Gly Gln Pro Gly Thr Asn Gly Gln His Ala
            420                 425                 430

Phe Phe Gln Leu Ile His Gln Gly Thr Lys Leu Val Pro Gly Asp Phe
        435                 440                 445

Leu Ala Ala Ala Gln Ser Gln Tyr Asp Leu Pro Asp His His Asp Ile
    450                 455                 460

Leu Ile Ser Asn Phe Leu Ala Gln Ala Glu Ala Leu Met Arg Gly Lys
465                 470                 475                 480

Thr Glu Glu Glu Val Arg Gln Asp Leu Ser His Glu Pro Asn Leu Asp
                485                 490                 495
```

-continued

```
Asp Ala Leu Ile Ala Ser Lys Ile Phe Glu Gly Asn Lys Pro Ser Asn
            500                 505                 510

Ser Phe Leu Phe Lys Lys Leu Thr Pro Arg Thr Leu Gly Thr Leu Ile
        515                 520                 525

Ala Phe Tyr Glu His Lys Ile Phe Val Gln Gly Val Ile Trp Asn Ile
    530                 535                 540

Asn Ser Phe Asp Gln Met Gly Val Glu Leu Gly Lys Val Leu Ala Lys
545                 550                 555                 560

Ala Ile Leu Pro Glu Leu Lys Asn Asp Asp Ile Ile Ala Ser His Asp
                565                 570                 575

Ser Ser Thr Asn Gly Leu Ile Asn Thr Tyr Lys Arg Leu Arg Lys Ala
            580                 585                 590
```

<210> SEQ ID NO 5
<211> LENGTH: 1311
<212> TYPE: DNA
<213> ORGANISM: METHYLOMONAS SP.

<400> SEQUENCE: 5

```
gatgtggtca catggcccta tcacttaacg gctgatattc gattttgtca ttggtttttt     60

cttaacttta acttctacac gctcatgaac aaacctaaaa aagttgcaat actgacagca    120

ggcggcttgg cgccttgttt gaattccgca atcggtagtt tgatcgaacg ttataccgaa    180

atcgatccta gcatagaaat catttgctat cgcggcggtt ataaaggcct gttgctgggc    240

gattcttatc cagtaacggc cgaagtgcgt aaaaaggcgg gtgttctgca acgttttggc    300

ggttctgtga tcggcaacag ccgcgtcaaa ttgaccaatg tcaaagactg cgtgaaacgc    360

ggtttggtca aagagggtga agatccgcaa aaagtcgcgg ctgatcaatt ggttaaggat    420

ggtgtcgata ttctgcacac catcggcggc gatgatacca atacggcagc agcggatttg    480

gcagcattcc tggccagaaa taattacgga ctgaccgtca ttggtttacc taaaaccgtc    540

gataacgacg tatttccgat caagcaatca ctaggtgctt ggactgccgc cgagcaaggc    600

gcgcgttatt tcatgaacgt ggtggccgaa aacaacgcca acccacgcat gctgatcgta    660

cacgaagtga tgggccgtaa ctgcggctgg ctgaccgctg caaccgcgca ggaatatcgc    720

aaattactgg accgtgccga gtggttgccg gaattgggtt tgactcgtga atcttatgaa    780

gtgcacgcgg tattcgttcc ggaaatggcg atcgacctgg aagccgaagc caagcgcctg    840

cgcgaagtga tggacaaagt cgattgcgtc aacatcttcg tttccgaagg tgccggcgtc    900

gaagctatcg tcgcggaaat gcaggccaaa ggccaggaag tgccgcgcga tgcgttcggc    960

cacatcaaac tggatgcggt caaccctggt aaatggttcg gcgagcaatt cgcgcagatg   1020

ataggcgcgg aaaaaaccct ggtacaaaaa tcgggatact tcgcccgtgc ttctgcttcc   1080

aacgttgacg acatgcgttt gatcaaatcg tgcgccgact tggcggtcga gtgcgcgttc   1140

cgccgcgagt ctggcgtgat cggtcacgac gaagacaacg gcaacgtgtt gcgtgcgatc   1200

gagtttccgc gcatcaaggg cggcaaaccg ttcaatatcg acaccgactg gttcaatagc   1260

atgttgagcg aaatcggcca gcctaaaggc ggtaaagtcg aagtcagcca c            1311
```

<210> SEQ ID NO 6
<211> LENGTH: 437
<212> TYPE: PRT
<213> ORGANISM: METHYLOMONAS SP.

<400> SEQUENCE: 6

```
Asp Val Val Thr Trp Pro Tyr His Leu Thr Ala Asp Ile Arg Phe Cys
```

-continued

```
1               5                   10                  15

His Trp Phe Phe Leu Asn Phe Asn Phe Tyr Thr Leu Met Asn Lys Pro
            20                  25                  30

Lys Lys Val Ala Ile Leu Thr Ala Gly Gly Leu Ala Pro Cys Leu Asn
        35                  40                  45

Ser Ala Ile Gly Ser Leu Ile Glu Arg Tyr Thr Glu Ile Asp Pro Ser
    50                  55                  60

Ile Glu Ile Ile Cys Tyr Arg Gly Gly Tyr Lys Gly Leu Leu Leu Gly
65                  70                  75                  80

Asp Ser Tyr Pro Val Thr Ala Glu Val Arg Lys Lys Ala Gly Val Leu
                85                  90                  95

Gln Arg Phe Gly Gly Ser Val Ile Gly Asn Ser Arg Val Lys Leu Thr
            100                 105                 110

Asn Val Lys Asp Cys Val Lys Arg Gly Leu Val Lys Glu Gly Glu Asp
        115                 120                 125

Pro Gln Lys Val Ala Ala Asp Gln Leu Val Lys Asp Gly Val Asp Ile
    130                 135                 140

Leu His Thr Ile Gly Gly Asp Asp Thr Asn Thr Ala Ala Ala Asp Leu
145                 150                 155                 160

Ala Ala Phe Leu Ala Arg Asn Asn Tyr Gly Leu Thr Val Ile Gly Leu
                165                 170                 175

Pro Lys Thr Val Asp Asn Asp Val Phe Pro Ile Lys Gln Ser Leu Gly
            180                 185                 190

Ala Trp Thr Ala Ala Glu Gln Gly Ala Arg Tyr Phe Met Asn Val Val
        195                 200                 205

Ala Glu Asn Asn Ala Asn Pro Arg Met Leu Ile Val His Glu Val Met
    210                 215                 220

Gly Arg Asn Cys Gly Trp Leu Thr Ala Ala Thr Ala Gln Glu Tyr Arg
225                 230                 235                 240

Lys Leu Leu Asp Arg Ala Glu Trp Leu Pro Glu Leu Gly Leu Thr Arg
                245                 250                 255

Glu Ser Tyr Glu Val His Ala Val Phe Val Pro Glu Met ala Ile Asp
            260                 265                 270

Leu Glu Ala Glu Ala Lys Arg Leu Arg Glu Val Met Asp Lys Val Asp
        275                 280                 285

Cys Val Asn Ile Phe Val Ser Glu Gly Ala Gly Val Glu Ala Ile Val
    290                 295                 300

Ala Glu Met Gln Ala Lys Gly Gln Glu Val Pro Arg Asp Ala Phe Gly
305                 310                 315                 320

His Ile Lys Leu Asp Ala Val Asn Pro Gly Lys Trp Phe Gly Glu Gln
                325                 330                 335

Phe Ala Gln Met Ile Gly Ala Glu Lys Thr Leu Val Gln Lys Ser Gly
            340                 345                 350

Tyr Phe Ala Arg Ala Ser Ala Ser Asn Val Asp Asp Met Arg Leu Ile
        355                 360                 365

Lys Ser Cys Ala Asp Leu Ala Val Glu Cys Ala Phe Arg Arg Glu Ser
    370                 375                 380

Gly Val Ile Gly His Asp Glu Asp Asn Gly Asn Val Leu Arg Ala Ile
385                 390                 395                 400

Glu Phe Pro Arg Ile Lys Gly Gly Lys Pro Phe Asn Ile Asp Thr Asp
                405                 410                 415

Trp Phe Asn Ser Met Leu Ser Glu Ile Gly Gln Pro Lys Gly Gly Lys
            420                 425                 430
```

```
Val Glu Val Ser His
        435

<210> SEQ ID NO 7
<211> LENGTH: 1360
<212> TYPE: DNA
<213> ORGANISM: METHYLOMONAS SP.

<400> SEQUENCE: 7

agtgtcccgc actcgcatca cccggagaca tccttaatgc atcccgtact cgaaaaagtc     60

acagaacaag tcatcgcccg cagccgggaa acccgtgccg cttatctgaa gcgcatagag    120

gccgccatcg ccgaaggccc gcaacgcaat aaactgcctt gcgccaatct ggcccacggt    180

ttcgcggtct gttcggccat cgaaaaagaa gaattgtctc atggccccaa gcccaatgtc    240

ggcatcatct cggcctacaa cgacatgctg tccgcgcacg aaccctacaa ggattatcct    300

gccctgatca aacaggccgt gcgcgaagcc ggcggcgtgg ctcaattcgc cggcggcgtg    360

cccgcgatgt gcgacggcgt cacccagggc atgccgggca tggaattgtc gctattcagc    420

cgcgacgtca tcgcgatgtc caccgcgatc ggcctggctc ataacatgtt cgacgcggcg    480

ctgtatctgg gcgtctgcga caagatcgta cccggtttgt tgatcggtgc attgagcttc    540

ggccatttgc cggccgtttt cttgccagcc ggccccatga ccagcggcct gtccaacaag    600

gaaaaatccc gtgcccggca aaaatacgcc gaaggtaaga tcggtgaaaa agaattgctg    660

gaatcggaag ccaagtctta ccacagccca ggcacctgca ccttctatgg caccgccaac    720

agcaaccaga tgatggtcga gatcatgggc ctgcacctgc ccggtagttc cttcatcaat    780

ccttacaccc cactgcgcga cgaactgacc aaggccgccg ccaggcaggt gttgaaattc    840

accgcgctgg gcaacgactt caggccaatc gcgcatgtga tcgacgaaaa agccatcatc    900

aatgccatca tcggcttgct ggcgaccggc ggttcgacca accataccat ccatttgatc    960

gcgattgccc gcgccgccgg catcatcatc aactgggacg atttcgacgc cctatccaaa   1020

gtcattccgt tgctgaccaa gatctatccg aacggcccgg ccgacgtcaa ccaattccag   1080

gcggccggcg gcatgagctt attgatacac gaactgctgg atcacggctt gttgcacggc   1140

gacatcctga ccataggcga ccagcgcggc atggcccaat acagtcaagt accgacgctg   1200

caagacggcc aattacaatg gcagcccggt cctaccgcat cgcgcgatcc cgaaatcatc   1260

gccagcgtgg caaaaccttt cgccgccggt ggtggcctgc atgtgatgca tggcaatctg   1320

ggccgcggcg tatccaagat ttccgccgtc tccgaagatc                          1360

<210> SEQ ID NO 8
<211> LENGTH: 618
<212> TYPE: PRT
<213> ORGANISM: METHYLOMONAS SP.

<400> SEQUENCE: 8

Ser Val Pro His Ser His His Pro Glu Thr Ser Leu Met His Pro Val
  1               5                  10                  15

Leu Glu Lys Val Thr Glu Gln Val Ile Ala Arg Ser Arg Glu Thr Arg
             20                  25                  30

Ala Ala Tyr Leu Lys Arg Ile Glu Ala Ala Ile Ala Glu Gly Pro Gln
        35                  40                  45

Arg Asn Lys Leu Pro Cys Ala Asn Leu Ala His Gly Phe Ala Val Cys
     50                  55                  60

Ser Ala Ile Glu Lys Glu Glu Leu Ser His Gly Pro Lys Pro Asn Val
```

-continued

```
65                  70                  75                  80

Gly Ile Ile Ser Ala Tyr Asn Asp Met Leu Ser Ala His Glu Pro Tyr
                85                  90                  95

Lys Asp Tyr Pro Ala Leu Ile Lys Gln Ala Val Arg Glu Ala Gly Gly
            100                 105                 110

Val Ala Gln Phe Ala Gly Gly Val Pro Ala Met Cys Asp Gly Val Thr
        115                 120                 125

Gln Gly Met Pro Gly Met Glu Leu Ser Leu Phe Ser Arg Asp Val Ile
    130                 135                 140

Ala Met Ser Thr Ala Ile Gly Leu Ala His Asn Met Phe Asp Ala Ala
145                 150                 155                 160

Leu Tyr Leu Gly Val Cys Asp Lys Ile Val Pro Gly Leu Leu Ile Gly
                165                 170                 175

Ala Leu Ser Phe Gly His Leu Pro Ala Val Phe Leu Pro Ala Gly Pro
            180                 185                 190

Met Thr Ser Gly Leu Ser Asn Lys Glu Lys Ser Arg Ala Arg Gln Lys
        195                 200                 205

Tyr Ala Glu Gly Lys Ile Gly Glu Lys Glu Leu Leu Glu Ser Glu Ala
    210                 215                 220

Lys Ser Tyr His Ser Pro Gly Thr Cys Thr Phe Tyr Gly Thr Ala Asn
225                 230                 235                 240

Ser Asn Gln Met Met Val Glu Ile Met Gly Leu His Leu Pro Gly Ser
                245                 250                 255

Ser Phe Ile Asn Pro Tyr Thr Pro Leu Arg Asp Glu Leu Thr Lys Ala
            260                 265                 270

Ala Ala Arg Gln Val Leu Lys Phe Thr Ala Leu Gly Asn Asp Phe Arg
        275                 280                 285

Pro Ile Ala His Val Ile Asp Glu Lys Ala Ile Ile Asn Ala Ile Ile
    290                 295                 300

Gly Leu Leu Ala Thr Gly Gly Ser Thr Asn His Thr Ile His Leu Ile
305                 310                 315                 320

Ala Ile Ala Arg Ala Ala Gly Ile Ile Ile Asn Trp Asp Asp Phe Asp
                325                 330                 335

Ala Leu Ser Lys Val Ile Pro Leu Leu Thr Lys Ile Tyr Pro Asn Gly
            340                 345                 350

Pro Ala Asp Val Asn Gln Phe Gln Ala Ala Gly Gly Met Ser Leu Leu
        355                 360                 365

Ile His Glu Leu Leu Asp His Gly Leu Leu His Gly Asp Ile Leu Thr
    370                 375                 380

Ile Gly Asp Gln Arg Gly Met ala Gln Tyr Ser Gln Val Pro Thr Leu
385                 390                 395                 400

Gln Asp Gly Gln Leu Gln Trp Gln Pro Gly Pro Thr Ala Ser Arg Asp
                405                 410                 415

Pro Glu Ile Ile Ala Ser Val Ala Lys Pro Phe Ala Ala Gly Gly Gly
            420                 425                 430

Leu His Val Met His Gly Asn Leu Gly Arg Gly Val Ser Lys Ile Ser
        435                 440                 445

Ala Val Ser Glu Asp His Gln Val Val Thr Ala Pro Ala Met Val Phe
    450                 455                 460

Asp Asp Gln Leu Asp Val Val Ala Ala Phe Lys Arg Gly Glu Leu Glu
465                 470                 475                 480

Lys Asp Val Ile Val Val Leu Arg Phe Gln Gly Pro Lys Ala Asn Gly
                485                 490                 495
```

-continued

```
Met Pro Glu Leu His Lys Leu Thr Pro Val Leu Gly Val Leu Gln Asp
            500                 505                 510

Arg Gly Phe Lys Val Gly Leu Leu Thr Asp Gly Arg Met Ser Gly Ala
        515                 520                 525

Ser Gly Lys Val Pro Ser Ala Ile His Met Trp Pro Glu Cys Ile Asp
    530                 535                 540

Gly Gly Pro Leu Ala Lys Val Arg Asp Gly Asp Ile Ile Val Met Asn
545                 550                 555                 560

Thr Gln Thr Gly Glu Val Asn Val Gln Val Asp Pro Ala Glu Phe Lys
                565                 570                 575

Ala Arg Val Ala Glu Pro Asn His Ala Thr Gly His His Phe Gly Met
            580                 585                 590

Gly Arg Glu Leu Phe Gly Ala Met Arg Ala Gln Ala Ser Thr Ala Glu
        595                 600                 605

Thr Gly Ala Thr Asn Leu Phe Phe Val Asp
    610                 615
```

<210> SEQ ID NO 9
<211> LENGTH: 1477
<212> TYPE: DNA
<213> ORGANISM: METHYLOMONAS SP.

<400> SEQUENCE: 9

```
atggcattgg gctttttgct ccgtagcccc aaagacatga caaaaaacat tacttacaaa     60

ccctgcgacc tggtgattta cggcgcactg ggcgatttat ccaaacgtaa actactgatt    120

tcattatacc gtttggaaaa acacaatctg ctcgagcccg atacgcgcat catcggcgta    180

gatcgtttgg aagaaaccag cgacagtttc gtcgaaattg cgcacaaaag cttgcaggcg    240

tttttgaaca acgtcatcga cgcagaaatc tggcaacgtt tttccaaacg cttgtcctat    300

ttgaaaatcg atctgaccca acccgagcaa tacaaacaac tgcatacggt cgtcgatgcc    360

gaaaaacgag tcatggtgaa ttatttcgcg gtggcaccct tttgttcaa aaacatttgc     420

caaggcttgc atgactgcgg cgtattgacg gccgaatcgc gcatggtgat ggaaaaaccc    480

atcggccacg acctgaaatc gtcgaaagaa atcaacgacg tcgtcgccga cgtattccac    540

gaagaccagg tctaccgcat cgaccactac ctgggcaagg aaacggtctt gaacttgctg    600

gccttgcgtt tcgccaattc gatattcacg accaactgga atcacaacac gatagaccat    660

atccagatta cggtcggtga ggacatcggc atcgagggcc gttgggaata tttcgacaag    720

accggccaat tgcgcgacat gctgcaaaac catttgctgc aaatcctgac cttcgtcgcg    780

atggagccgc ccgcggatct gtcggccgaa agcatacaca tggaaaaaat caaggtcctg    840

aaagccttgc ggccaatcac cgtgcgcaat gtcgaggaaa aaaccgtgcg cggtcaatac    900

accgccggtt tcatcaaagg caagtcggta ccgggttatc tggaagaaga aggtgccaac    960

accgaaagca cgaccgaaac tttcgtcgcg atccgcgtgg atatcgataa ctggcgctgg   1020

gccggtgtcc cgttttacat gcgtaccggc aaacgcacgc ccaacaaacg caccgagatt   1080

gtggtcaatt tcaagcaatt gccgcacaac atcttcaagg acagttttca tgaactgccg   1140

gccaataaac tggtcattca tttgcaaccg aacgaagggg tggatgtcat gatgttgaac   1200

aaggtgccgg gcatagacgg caacatcaag ttgcaacaga ccaaactgga tttgagcttt   1260

tccgaaacct tcaagaaaaa ccgaattttc ggcggctacg aaaaactgat tctggaagcc   1320

ctgcgcggca acccgacgct gtttttgagc cgcgaggaaa tagaacaagc ctggacctgg   1380
```

-continued

```
gtcgattcga ttcaggatgc ctggcaacac aaccacacgc cacccaaacc ctatcccgcg   1440

ggtagctggg gtccagtggc atcggtcgca ttactgg                            1477


<210> SEQ ID NO 10
<211> LENGTH: 501
<212> TYPE: PRT
<213> ORGANISM: METHYLOMONAS SP.

<400> SEQUENCE: 10

Met ala Leu Gly Phe Leu Leu Arg Ser Pro Lys Asp Met Thr Lys Asn
  1               5                  10                  15

Ile Thr Tyr Lys Pro Cys Asp Leu Val Ile Tyr Gly Ala Leu Gly Asp
             20                  25                  30

Leu Ser Lys Arg Lys Leu Leu Ile Ser Leu Tyr Arg Leu Glu Lys His
         35                  40                  45

Asn Leu Leu Glu Pro Asp Thr Arg Ile Ile Gly Val Asp Arg Leu Glu
     50                  55                  60

Glu Thr Ser Asp Ser Phe Val Glu Ile Ala His Lys Ser Leu Gln Ala
 65                  70                  75                  80

Phe Leu Asn Asn Val Ile Asp Ala Glu Ile Trp Gln Arg Phe Ser Lys
                 85                  90                  95

Arg Leu Ser Tyr Leu Lys Ile Asp Leu Thr Gln Pro Glu Gln Tyr Lys
            100                 105                 110

Gln Leu His Thr Val Val Asp Ala Glu Lys Arg Val Met Val Asn Tyr
        115                 120                 125

Phe Ala Val Ala Pro Phe Leu Phe Lys Asn Ile Cys Gln Gly Leu His
    130                 135                 140

Asp Cys Gly Val Leu Thr Ala Glu Ser Arg Met Val Met Glu Lys Pro
145                 150                 155                 160

Ile Gly His Asp Leu Lys Ser Ser Lys Glu Ile Asn Asp Val Val Ala
                165                 170                 175

Asp Val Phe His Glu Asp Gln Val Tyr Arg Ile Asp His Tyr Leu Gly
            180                 185                 190

Lys Glu Thr Val Leu Asn Leu Leu Ala Leu Arg Phe Ala Asn Ser Ile
        195                 200                 205

Phe Thr Thr Asn Trp Asn His Asn Thr Ile Asp His Ile Gln Ile Thr
    210                 215                 220

Val Gly Glu Asp Ile Gly Ile Glu Gly Arg Trp Glu Tyr Phe Asp Lys
225                 230                 235                 240

Thr Gly Gln Leu Arg Asp Met Leu Gln Asn His Leu Leu Gln Ile Leu
                245                 250                 255

Thr Phe Val Ala Met Glu Pro Pro Ala Asp Leu Ser Ala Glu Ser Ile
            260                 265                 270

His Met Glu Lys Ile Lys Val Leu Lys Ala Leu Arg Pro Ile Thr Val
        275                 280                 285

Arg Asn Val Glu Glu Lys Thr Val Arg Gly Gln Tyr Thr Ala Gly Phe
    290                 295                 300

Ile Lys Gly Lys Ser Val Pro Gly Tyr Leu Glu Glu Glu Gly Ala Asn
305                 310                 315                 320

Thr Glu Ser Thr Thr Glu Thr Phe Val Ala Ile Arg Val Asp Ile Asp
                325                 330                 335

Asn Trp Arg Trp Ala Gly Val Pro Phe Tyr Met Arg Thr Gly Lys Arg
            340                 345                 350

Thr Pro Asn Lys Arg Thr Glu Ile Val Val Asn Phe Lys Gln Leu Pro
```

-continued

```
        355                 360                 365

His Asn Ile Phe Lys Asp Ser Phe His Glu Leu Pro Ala Asn Lys Leu
    370                 375                 380

Val Ile His Leu Gln Pro Asn Glu Gly Val Asp Val Met Met Leu Asn
385                 390                 395                 400

Lys Val Pro Gly Ile Asp Gly Asn Ile Lys Leu Gln Gln Thr Lys Leu
                405                 410                 415

Asp Leu Ser Phe Ser Glu Thr Phe Lys Lys Asn Arg Ile Phe Gly Gly
            420                 425                 430

Tyr Glu Lys Leu Ile Leu Glu Ala Leu Arg Gly Asn Pro Thr Leu Phe
        435                 440                 445

Leu Ser Arg Glu Glu Ile Glu Gln Ala Trp Thr Trp Val Asp Ser Ile
    450                 455                 460

Gln Asp Ala Trp Gln His Asn His Thr Pro Pro Lys Pro Tyr Pro Ala
465                 470                 475                 480

Gly Ser Trp Gly Pro Val Ala Ser Val Ala Leu Leu Ala Arg Asp Gly
                485                 490                 495

Arg Ala Trp Glu Glu
            500


<210> SEQ ID NO 11
<211> LENGTH: 984
<212> TYPE: DNA
<213> ORGANISM: METHYLOMONAS SP.

<400> SEQUENCE: 11

atggcaagaa acttacttga gcaactccgc gagatgaccg ttgttgttgc cgataccggt      60

gacatccagg cgatcgaaac cttcaagccg cgcgatgcaa cgaccaaccc gtctttgatc     120

accgccgcgg cgcaaatgcc gcaatatcaa ggcatcgttg acgacacctt gaaaggtgcg     180

cgtgcgacgt tgggtgccag cgcttcggct gccgaggtgg cttcattggc gttcgatcgt     240

ttggcggttt ctttcggttt gaaaatcctg gaaatcatcg aaggtcgcgt ttccaccgag     300

gttgatgcgc gtttgtctta tgacaccgaa ggcactattg ccaaaggccg ggatctgatc     360

aaacaatacg aagctgcagg tgtttccaaa gagcgcgtac tgatcaaaat tgccgcgacc     420

tgggaaggca tccaggcggc tgccgttttg gaaaaagaag gtattcacac caacttgacc     480

ctgttgttcg gtctgcacca ggcgattgct tgtgccgaaa acggcattac cctgatttct     540

ccgtttgtcg gccgtattct ggactggtac aaaaaagaca ctggccgcga ctcttatcct     600

tccaacgaag atcctggcgt attgtctgta actgaagttt ataactacta caaaaaattt     660

ggttataaaa ctgaagtcat gggcgcgagc ttccgtaaca tcggcgaaat caccgaattg     720

gcgggttgcg atctgttgac catcgcgcct tctctgctgg ccgaactgca atccgttgaa     780

ggtgatttgc cacgcaaact ggaccctgca aaagcagccg gttcttcgat cgaaaaaatc     840

agcgttgaca aagcgacttt cgagcgcatg cacgaagaaa accgcatggc caaagaaaaa     900

ctggccgaag gtatcgacgg ttttgcgaaa gcgttggaaa ccttggaaaa attgttggcg     960

gatcgtttgg ctgctctgga agca                                            984


<210> SEQ ID NO 12
<211> LENGTH: 328
<212> TYPE: PRT
<213> ORGANISM: METHYLOMONAS SP.

<400> SEQUENCE: 12
```

-continued

```
Met ala Arg Asn Leu Leu Glu Gln Leu Arg Glu Met Thr Val Val Val
  1               5                  10                  15

Ala Asp Thr Gly Asp Ile Gln Ala Ile Glu Thr Phe Lys Pro Arg Asp
             20                  25                  30

Ala Thr Thr Asn Pro Ser Leu Ile Thr Ala Ala Ala Gln Met Pro Gln
         35                  40                  45

Tyr Gln Gly Ile Val Asp Asp Thr Leu Lys Gly Ala Arg Ala Thr Leu
     50                  55                  60

Gly Ala Ser Ala Ser Ala Ala Glu Val Ala Ser Leu Ala Phe Asp Arg
 65                  70                  75                  80

Leu Ala Val Ser Phe Gly Leu Lys Ile Leu Glu Ile Ile Glu Gly Arg
                 85                  90                  95

Val Ser Thr Glu Val Asp Ala Arg Leu Ser Tyr Asp Thr Glu Gly Thr
            100                 105                 110

Ile Ala Lys Gly Arg Asp Leu Ile Lys Gln Tyr Glu Ala Ala Gly Val
        115                 120                 125

Ser Lys Glu Arg Val Leu Ile Lys Ile Ala Ala Thr Trp Glu Gly Ile
    130                 135                 140

Gln Ala Ala Ala Val Leu Glu Lys Glu Gly Ile His Thr Asn Leu Thr
145                 150                 155                 160

Leu Leu Phe Gly Leu His Gln Ala Ile Ala Cys Ala Glu Asn Gly Ile
                165                 170                 175

Thr Leu Ile Ser Pro Phe Val Gly Arg Ile Leu Asp Trp Tyr Lys Lys
            180                 185                 190

Asp Thr Gly Arg Asp Ser Tyr Pro Ser Asn Glu Asp Pro Gly Val Leu
        195                 200                 205

Ser Val Thr Glu Val Tyr Asn Tyr Tyr Lys Lys Phe Gly Tyr Lys Thr
    210                 215                 220

Glu Val Met Gly Ala Ser Phe Arg Asn Ile Gly Glu Ile Thr Glu Leu
225                 230                 235                 240

Ala Gly Cys Asp Leu Leu Thr Ile Ala Pro Ser Leu Leu Ala Glu Leu
                245                 250                 255

Gln Ser Val Glu Gly Asp Leu Pro Arg Lys Leu Asp Pro Ala Lys Ala
            260                 265                 270

Ala Gly Ser Ser Ile Glu Lys Ile Ser Val Asp Lys Ala Thr Phe Glu
        275                 280                 285

Arg Met His Glu Glu Asn Arg Met ala Lys Glu Lys Leu Ala Glu Gly
    290                 295                 300

Ile Asp Gly Phe Ala Lys Ala Leu Glu Thr Leu Glu Lys Leu Leu Ala
305                 310                 315                 320

Asp Arg Leu Ala Ala Leu Glu Ala
                325
```

<210> SEQ ID NO 13
<211> LENGTH: 480
<212> TYPE: DNA
<213> ORGANISM: METHYLOMONAS SP.

<400> SEQUENCE: 13

```
atggccgcgg gcggcgtggg cttgacgcaa ttgctgccag aactggccga agctattggt    60

ccgacgagcc gatttcatgt gcaggtcatt ggtgacacgg tggaggacat cgttgcggaa   120

gccaaacggc tacacgattt gcccgtcgac atagtggtga aaattccggc gcatggcgcc   180

ggactggcgg ccatcaagca gatcaagcgc cacgatattc cggtgctggc gacagcgatt   240
```

-continued

```
tacaacgtgc agcaaggttg gctggcggct ttgaacggcg ccgattatct ggcgccttat   300

ctgaatcgcg tcgataacca gggttttgac ggtattggcg tggtcgccga tctgcagagc   360

ttgatcgacc ggtatcaaat gcccaccaaa ctcctggtag cgagcttcaa aaacgtacaa   420

caggtgctgc aggtgttgaa actgggcgtg gcgtcggtga cgctgccttt ggacattgtg   480


<210> SEQ ID NO 14
<211> LENGTH: 160
<212> TYPE: PRT
<213> ORGANISM: METHYLOMONAS SP.

<400> SEQUENCE: 14

Met ala Ala Gly Gly Val Gly Leu Thr Gln Leu Leu Pro Glu Leu Ala
  1               5                  10                  15

Glu Ala Ile Gly Pro Thr Ser Arg Phe His Val Gln Val Ile Gly Asp
             20                  25                  30

Thr Val Glu Asp Ile Val Ala Glu Ala Lys Arg Leu His Asp Leu Pro
         35                  40                  45

Val Asp Ile Val Val Lys Ile Pro Ala His Gly Ala Gly Leu Ala Ala
     50                  55                  60

Ile Lys Gln Ile Lys Arg His Asp Ile Pro Val Leu Ala Thr Ala Ile
 65                  70                  75                  80

Tyr Asn Val Gln Gln Gly Trp Leu Ala Ala Leu Asn Gly Ala Asp Tyr
                 85                  90                  95

Leu Ala Pro Tyr Leu Asn Arg Val Asp Asn Gln Gly Phe Asp Gly Ile
            100                 105                 110

Gly Val Val Ala Asp Leu Gln Ser Leu Ile Asp Arg Tyr Gln Met Pro
        115                 120                 125

Thr Lys Leu Leu Val Ala Ser Phe Lys Asn Val Gln Gln Val Leu Gln
    130                 135                 140

Val Leu Lys Leu Gly Val Ala Ser Val Thr Leu Pro Leu Asp Ile Val
145                 150                 155                 160


<210> SEQ ID NO 15
<211> LENGTH: 1005
<212> TYPE: DNA
<213> ORGANISM: METHYLOMONAS SP.

<400> SEQUENCE: 15

atggctttag tgtcattgcg acaacttttg gattatgcgg ccgagcatgg ctttgccgtg    60

ccggcgttca acgtcagcaa catggagcag gtacaggcca tcatgcaggc ggccgctgcc   120

tgcgatagtc cagtgatcat gcaaggttcg gccggcgcca accgctatgc cggcgaagtg   180

tttctacggc atttgatatt ggcggccgtg gagcaatatc cgcatattcc ggtcgtcatg   240

caccgcgacc atgcacccac gcccgacatc tgcgcgcaag ccatacaatc gggcttcagc   300

tcggtgatga tggacggttc gttgctggca gacatgaaaa ccccggcttc ttttgcatac   360

aacgtcgacg tcacccgcac cgtggtcaag atggcgcatg cctgcggcgt atcggtggaa   420

ggcgaaatcg gctgcctggg agcgctggag gccaagtccg cgcaagatca cagccgtttg   480

ctgaccgatc ccgacgaagc ggtcgaattc gtcgaacaga cccaggtcga tgccgtggcc   540

gtggccatcg gcaccagcca cggcgcctat aaattcagca agccgcccac cggcgaagtg   600

ctggtgatca gtcgattgaa agaactgcag caacgactgc caaataccca ttttgtgatg   660

catggctcca gttcggtgcc gcaggattgg ttgaaaatca tcaacgatta tggcggcgat   720

attccggaaa cctatggcgt gccggtcgaa gaaatcgtcg aaggcataaa atatggtgtg   780
```

-continued

```
cgcaaggtca acatcgatac cgacctgcgc atggcgtcca ccggcgcgat gcgcaggttt    840

ctggcccaac cggaaaacgc ctcggagcta gacgcgcgca agacctatca agccgccagg    900

gacgcaatgc aggcattatg ccaggctcgc tacgaagcgt tcggttcggc gggacatgcc    960

ggcaaaatca aaccggtttc actggcggca atggccaaac gctat                   1005
```

```
<210> SEQ ID NO 16
<211> LENGTH: 335
<212> TYPE: PRT
<213> ORGANISM: METHYLOMONAS SP.

<400> SEQUENCE: 16

Met ala Leu Val Ser Leu Arg Gln Leu Leu Asp Tyr Ala Ala Glu His
  1               5                  10                  15

Gly Phe Ala Val Pro Ala Phe Asn Val Ser Asn Met Glu Gln Val Gln
             20                  25                  30

Ala Ile Met Gln Ala Ala Ala Ala Cys Asp Ser Pro Val Ile Met Gln
         35                  40                  45

Gly Ser Ala Gly Ala Asn Arg Tyr Ala Gly Glu Val Phe Leu Arg His
     50                  55                  60

Leu Ile Leu Ala Ala Val Glu Gln Tyr Pro His Ile Pro Val Val Met
 65                  70                  75                  80

His Arg Asp His Ala Pro Thr Pro Asp Ile Cys Ala Gln Ala Ile Gln
                 85                  90                  95

Ser Gly Phe Ser Ser Val Met Met Asp Gly Ser Leu Leu Ala Asp Met
            100                 105                 110

Lys Thr Pro Ala Ser Phe Ala Tyr Asn Val Asp Val Thr Arg Thr Val
        115                 120                 125

Val Lys Met ala His Ala Cys Gly Val Ser Val Glu Gly Glu Ile Gly
    130                 135                 140

Cys Leu Gly Ala Leu Glu Ala Lys Ser Ala Gln Asp His Ser Arg Leu
145                 150                 155                 160

Leu Thr Asp Pro Asp Glu Ala Val Glu Phe Val Glu Gln Thr Gln Val
                165                 170                 175

Asp Ala Val Ala Val Ala Ile Gly Thr Ser His Gly Ala Tyr Lys Phe
            180                 185                 190

Ser Lys Pro Pro Thr Gly Glu Val Leu Val Ile Ser Arg Leu Lys Glu
        195                 200                 205

Leu Gln Gln Arg Leu Pro Asn Thr His Phe Val Met His Gly Ser Ser
    210                 215                 220

Ser Val Pro Gln Asp Trp Leu Lys Ile Ile Asn Asp Tyr Gly Gly Asp
225                 230                 235                 240

Ile Pro Glu Thr Tyr Gly Val Pro Val Glu Glu Ile Val Glu Gly Ile
                245                 250                 255

Lys Tyr Gly Val Arg Lys Val Asn Ile Asp Thr Asp Leu Arg Met ala
            260                 265                 270

Ser Thr Gly Ala Met Arg Arg Phe Leu Ala Gln Pro Glu Asn Ala Ser
        275                 280                 285

Glu Leu Asp Ala Arg Lys Thr Tyr Gln Ala Ala Arg Asp Ala Met Gln
    290                 295                 300

Ala Leu Cys Gln Ala Arg Tyr Glu Ala Phe Gly Ser Ala Gly His Ala
305                 310                 315                 320

Gly Lys Ile Lys Pro Val Ser Leu Ala Ala Met ala Lys Arg Tyr
                325                 330                 335
```

-continued

<210> SEQ ID NO 17
<211> LENGTH: 1074
<212> TYPE: DNA
<213> ORGANISM: METHYLOMONAS SP.

<400> SEQUENCE: 17

```
atgacaaaaa tcttagatgt tgtaaaaccc ggcgttgtca ccggtgaaga tgtgcaaaaa     60

attttcgcaa tctgcaaaga aaacaacttt gccttgccag ccgtcaacgt gatcagtacc    120

gataccatta atgcggtatt ggaagcggcc gccaaagcca aatcacctgt tgttatccag    180

ttttcaaatg gcggcgcggc tttcgttgcc ggtaaaggtt tgaaattgga aggtcaaggc    240

tgttcgattc atggtgccat ttcaggtgct caccacgttc accgcttggc ggaactctat    300

ggtgtacctg tcgttctgca taccgaccac gcggcgaaaa aattgctgcc atgggtagat    360

ggtatgctgg atgaaggtga aaaattcttt gcggccaccg gcaagccttt gttcagctcg    420

cacatgctgg acttgtccga agagagcctg gaagaaaaca tcgaaatctg cggtaaatac    480

ttggcgcgca tggcgaaaat gggtatgacc ttggaaatcg aactgggctg caccggcggt    540

gaagaagacg gcgtggacaa cagcggcatg gatcattccg cgttgtacac ccagccggaa    600

gacgtggctt acgcgtatga gcacctgagc aaaatcagcc ctaacttcac gattgcggct    660

tctttcggca acgtgcacgg cgtttactcg ccaggaaacg tcaagctgac gccaaaaatt    720

ctggataact cgcaaaaata cgtatccgaa aaattcggct tgccagctaa atcattgacc    780

ttcgtattcc atggcggctc tggttcgtct ccggaagaaa tcaaggaatc catcagctat    840

ggcgtagtga aaatgaacat cgataccgat acccaatggg caacctggga aggcgtgatg    900

aacttctaca agaaaaacga aggctatctg caaggccaga tcggcaatcc ggaaggtgcc    960

gacaagccga acaaaaaata ctatgaccca cgcgtatggc aacgtgccgg ccaagaaggc   1020

atggttgcac gtctgcaaca agcattccag gaattgaatg cagtaaacac gctg         1074
```

<210> SEQ ID NO 18
<211> LENGTH: 358
<212> TYPE: PRT
<213> ORGANISM: METHYLOMONAS SP.

<400> SEQUENCE: 18

```
Met Thr Lys Ile Leu Asp Val Val Lys Pro Gly Val Val Thr Gly Glu
  1               5                  10                  15

Asp Val Gln Lys Ile Phe Ala Ile Cys Lys Glu Asn Asn Phe Ala Leu
             20                  25                  30

Pro Ala Val Asn Val Ile Ser Thr Asp Thr Ile Asn Ala Val Leu Glu
         35                  40                  45

Ala Ala Ala Lys Ala Lys Ser Pro Val Val Ile Gln Phe Ser Asn Gly
     50                  55                  60

Gly Ala Ala Phe Val Ala Gly Lys Gly Leu Lys Leu Glu Gly Gln Gly
 65                  70                  75                  80

Cys Ser Ile His Gly Ala Ile Ser Gly Ala His His Val His Arg Leu
                 85                  90                  95

Ala Glu Leu Tyr Gly Val Pro Val Val Leu His Thr Asp His Ala Ala
            100                 105                 110

Lys Lys Leu Leu Pro Trp Val Asp Gly Met Leu Asp Glu Gly Glu Lys
        115                 120                 125

Phe Phe Ala Ala Thr Gly Lys Pro Leu Phe Ser Ser His Met Leu Asp
    130                 135                 140
```

-continued

```
Leu Ser Glu Glu Ser Leu Glu Glu Asn Ile Glu Ile Cys Gly Lys Tyr
145                 150                 155                 160

Leu Ala Arg Met ala Lys Met Gly Met Thr Leu Glu Ile Glu Leu Gly
                165                 170                 175

Cys Thr Gly Gly Glu Glu Asp Gly Val Asp Asn Ser Gly Met Asp His
            180                 185                 190

Ser Ala Leu Tyr Thr Gln Pro Glu Asp Val Ala Tyr Ala Tyr Glu His
        195                 200                 205

Leu Ser Lys Ile Ser Pro Asn Phe Thr Ile Ala Ala Ser Phe Gly Asn
    210                 215                 220

Val His Gly Val Tyr Ser Pro Gly Asn Val Lys Leu Thr Pro Lys Ile
225                 230                 235                 240

Leu Asp Asn Ser Gln Lys Tyr Val Ser Glu Lys Phe Gly Leu Pro Ala
                245                 250                 255

Lys Ser Leu Thr Phe Val Phe His Gly Gly Ser Gly Ser Ser Pro Glu
            260                 265                 270

Glu Ile Lys Glu Ser Ile Ser Tyr Gly Val Val Lys Met Asn Ile Asp
        275                 280                 285

Thr Asp Thr Gln Trp Ala Thr Trp Glu Gly Val Met Asn Phe Tyr Lys
    290                 295                 300

Lys Asn Glu Gly Tyr Leu Gln Gly Gln Ile Gly Asn Pro Glu Gly Ala
305                 310                 315                 320

Asp Lys Pro Asn Lys Lys Tyr Tyr Asp Pro Arg Val Trp Gln Arg Ala
                325                 330                 335

Gly Gln Glu Gly Met Val Ala Arg Leu Gln Gln Ala Phe Gln Glu Leu
            340                 345                 350

Asn Ala Val Asn Thr Leu
        355
```

<210> SEQ ID NO 19
<211> LENGTH: 636
<212> TYPE: DNA
<213> ORGANISM: METHYLOMONAS SP.

<400> SEQUENCE: 19

```
gaaaatacta tgtccgtcac catcaaagaa gtcatgacca cctcgcccgt tatgccggtc      60

atggtcatca atcatctgga acatgccgtc cctctggctc gcgcgctagt cgacggtggc     120

ttgaaagttt tggagatcac attgcgcacg ccggtggcac tggaatgtat ccgacgtatc     180

aaagccgaag taccggacgc catcgtcggc gcgggcacca tcatcaaccc tcataccttg     240

tatcaagcga ttgacgccgg tgcggaattc atcgtcagcc ccggcatcac cgaaaatcta     300

ctcaacgaag cgctagcatc cggcgtgcct atcctgcccg gcgtcatcac acccagcgag     360

gtcatgcgtt tattggaaaa aggcatcaat gcgatgaaat tctttccggc tgaagccgcc     420

ggcggcatac cgatgctgaa atcccttggc ggccccttgc cgcaagtcac cttctgtccg     480

accggcggcg tcaatcccaa aaacgcgccc gaatatctgg cattgaaaaa tgtcgcctgc     540

gtcggcggct cctggatggc gccggccgat ctggtagatg ccgaagactg ggcggaaatc     600

acgcggcggg cgagcgaggc cgcggcattg aaaaaa                               636
```

<210> SEQ ID NO 20
<211> LENGTH: 212
<212> TYPE: PRT
<213> ORGANISM: METHYLOMONAS SP.

```
<400> SEQUENCE: 20

Glu Asn Thr Met Ser Val Thr Ile Lys Glu Val Met Thr Thr Ser Pro
  1               5                  10                  15

Val Met Pro Val Met Val Ile Asn His Leu Glu His Ala Val Pro Leu
             20                  25                  30

Ala Arg Ala Leu Val Asp Gly Gly Leu Lys Val Leu Glu Ile Thr Leu
         35                  40                  45

Arg Thr Pro Val Ala Leu Glu Cys Ile Arg Arg Ile Lys Ala Glu Val
     50                  55                  60

Pro Asp Ala Ile Val Gly Ala Gly Thr Ile Ile Asn Pro His Thr Leu
 65                  70                  75                  80

Tyr Gln Ala Ile Asp Ala Gly Ala Glu Phe Ile Val Ser Pro Gly Ile
                 85                  90                  95

Thr Glu Asn Leu Leu Asn Glu Ala Leu Ala Ser Gly Val Pro Ile Leu
            100                 105                 110

Pro Gly Val Ile Thr Pro Ser Glu Val Met Arg Leu Leu Glu Lys Gly
        115                 120                 125

Ile Asn Ala Met Lys Phe Phe Pro Ala Glu Ala Ala Gly Gly Ile Pro
    130                 135                 140

Met Leu Lys Ser Leu Gly Gly Pro Leu Pro Gln Val Thr Phe Cys Pro
145                 150                 155                 160

Thr Gly Gly Val Asn Pro Lys Asn Ala Pro Glu Tyr Leu Ala Leu Lys
                165                 170                 175

Asn Val Ala Cys Val Gly Gly Ser Trp Met ala Pro Ala Asp Leu Val
            180                 185                 190

Asp Ala Glu Asp Trp Ala Glu Ile Thr Arg Arg Ala Ser Glu Ala Ala
        195                 200                 205

Ala Leu Lys Lys
    210


<210> SEQ ID NO 21
<211> LENGTH: 873
<212> TYPE: DNA
<213> ORGANISM: Methylomonas 16a

<400> SEQUENCE: 21

atgaaagtta ccaaagccgt ttttcccgtt gccggactgg gcacccggtc attgcccgca     60

accaaggccg ttgccaagga aatgttgccg gtggtggaca agccgctgat tcagtatgcg    120

gtggaagagg ccgtggccgc cggcatcgac acgatgattt tcgtgatcgg tagaaacaag    180

gaatccattg ccaaccattt cgataaatcc tacgaactgg aaaaggaact ggaaaaaagc    240

ggcaagaccg atttgctgaa aatgctgcgg gagattttgc ccgcgcatgt gtcctgcgta    300

ttcgtgcgtc aagcggaggc tctgggtttg gggcatgcgg tgcattgcgc caagccggtg    360

gtcggcaacg agccgtttgc ggtgatcttg ccggatgact tgatcgagga cggcgagcgc    420

ggttgcatga agcagatggt ggatttgttc gacaaagagc aaagcagcgt attgggggta    480

gagcgggtcg atcccaagga aacccataag tacggcatcg tcgaacatgc cgaaacctcg    540

cccagagtcg gttggttgag ttccatcgtc gagaaaccca aacccgaagt ggcgccctcc    600

aatatcgcgg tggtcgggcg ctacatcttg acgccggcca tttttcaaaa aatcgagaac    660

acggggcgcg gcgccggcgg cgaaattcaa ttgaccgatg cgattgccgc gttgatgaaa    720

gacgaacgcg ttttgtccta tgaattcgaa ggcaatcgct acgactgcgg ttccaagttt    780

ggtttttgt tggccaatgt cgaatatggc ttgctgcaca aggaaatcaa agccgaattc    840
```

-continued

```
gccaactatc tgaaacaacg cgtcagcaaa atc                                  873


<210> SEQ ID NO 22
<211> LENGTH: 293
<212> TYPE: PRT
<213> ORGANISM: Methylomonas 16a

<400> SEQUENCE: 22

Met Thr Met Lys Val Thr Lys Ala Val Phe Pro Val Ala Gly Leu Gly
  1               5                  10                  15

Thr Arg Ser Leu Pro Ala Thr Lys Ala Val Ala Lys Glu Met Leu Pro
             20                  25                  30

Val Val Asp Lys Pro Leu Ile Gln Tyr Ala Val Glu Glu Ala Val Ala
         35                  40                  45

Ala Gly Ile Asp Thr Met Ile Phe Val Ile Gly Arg Asn Lys Glu Ser
     50                  55                  60

Ile Ala Asn His Phe Asp Lys Ser Tyr Glu Leu Glu Lys Glu Leu Glu
 65                  70                  75                  80

Lys Ser Gly Lys Thr Asp Leu Leu Lys Met Leu Arg Glu Ile Leu Pro
                 85                  90                  95

Ala His Val Ser Cys Val Phe Val Arg Gln Ala Glu Ala Leu Gly Leu
            100                 105                 110

Gly His Ala Val His Cys Ala Lys Pro Val Val Gly Asn Glu Pro Phe
        115                 120                 125

Ala Val Ile Leu Pro Asp Asp Leu Ile Glu Asp Gly Glu Arg Gly Cys
    130                 135                 140

Met Lys Gln Met Val Asp Leu Phe Asp Lys Glu Gln Ser Ser Val Leu
145                 150                 155                 160

Gly Val Glu Arg Val Asp Pro Lys Glu Thr His Lys Tyr Gly Ile Val
                165                 170                 175

Glu His Ala Glu Thr Ser Pro Arg Val Gly Trp Leu Ser Ser Ile Val
            180                 185                 190

Glu Lys Pro Lys Pro Glu Val Ala Pro Ser Asn Ile Ala Val Val Gly
        195                 200                 205

Arg Tyr Ile Leu Thr Pro Ala Ile Phe Gln Lys Ile Glu Asn Thr Gly
    210                 215                 220

Arg Gly Ala Gly Gly Glu Ile Gln Leu Thr Asp Ala Ile Ala Ala Leu
225                 230                 235                 240

Met Lys Asp Glu Arg Val Leu Ser Tyr Glu Phe Glu Gly Asn Arg Tyr
                245                 250                 255

Asp Cys Gly Ser Lys Phe Gly Phe Leu Leu Ala Asn Val Glu Tyr Gly
            260                 265                 270

Leu Leu His Lys Glu Ile Lys Ala Glu Phe Ala Asn Tyr Leu Lys Gln
        275                 280                 285

Arg Val Ser Lys Ile
    290


<210> SEQ ID NO 23
<211> LENGTH: 1419
<212> TYPE: DNA
<213> ORGANISM: Methylomonas 16a

<400> SEQUENCE: 23

atgccactcg gtttgggaaa tatcttcaac gggctgttca agcaatacgg gcacacggtg      60

atcctgttgt tgagggttat cgacgtggtc atgttattgg gcgcggcctg gctggcgcat     120
```

-continued

```
tatttttggt tgcatgacag cgtcatcgat cagcattacc gtttcgtgat tgccctgggt    180

atcttgggtg cgatcatatt tttcgagatc ggccaggtgt atcggccgtg gcgcaatgac    240

gcgatgcgcg gcgaaattcc ccgcatcatc agagcctggt tgctggcctt gctgacggtg    300

gtgtccatcg tggccctggt cagattgcat ttttggtttg gttccagtta tcgctggatc    360

gcctcctggg gcggtttggg gctgttcttc gtactggcgg cccgcggtgt gctggcacag    420

gtgttgaagt ggttgcgtgc acggggctgg agccaggggc gcatcattct ggtgggtttg    480

aatcagatgg ccgtcgccgt cagtcggcaa ttgaatcact cttcctgggc cggtttgcag    540

gtgattggtt atgtcgatga ccgggccgaa gaccggctgg cggtggcgga ttattcgctg    600

ccacgcctgg gcaagttgag cgatctgcct cgtctggttt ccagacaagc cgtggatgaa    660

gtctgggtgg cgtttcctgg cgcttcgctg gccgagcggg tacagcacga attgcgccat    720

ttgccggtca gcattcgcct ggtgatcgat tgctttgcct ttaaacaaag caaattcctc    780

agtctgaaca cggtggccgg tatcccgacg ctggacgtct cggtgtcgcc gctgcatggc    840

gtcaatcgct atatcaagga aatcgaggac cgcttgctgg ccttgctgtt gttgttgctg    900

atcagcccgt tgatgctggt cattgcgctt ggcgtgaaac tgagttctcc gggcccggtg    960

ttttacaagc aggtcagagt gggctggaac aatcgcaaat tcacgatgct gaagtttcgt   1020

tcgatgccgg tcgatgccga ggccaaaacc ggcgcggtct gggccaggcc cggcgaaaac   1080

cgtgcaaccc ggtttggggc cttcctgcgc aaaaccagtc tggacgagtt gccgcagttg   1140

atcaatgtgc tcaagggcga catgtcgctg gtcggcccgc gccctgaacg gcccgatttc   1200

gtcgaggtgt tcaaggatca agtacccaat tacatgaaaa aacacatggt caaggcgggc   1260

attaccggtt gggcacaagt caacggctgg cgcggtgata ccgacctgaa tcgccgcatc   1320

gaacacgatc tgtattacat ccagcattgg tcggtctggt tcgatctgga gattgccttt   1380

cgcaccgtgt tgaccggctt tatcaacaaa aatgcctat                          1419
```

```
<210> SEQ ID NO 24
<211> LENGTH: 473
<212> TYPE: PRT
<213> ORGANISM: Methylomonas 16a

<400> SEQUENCE: 24

Met Pro Leu Gly Leu Gly Asn Ile Phe Asn Gly Leu Phe Lys Gln Tyr
  1               5                  10                  15

Gly His Thr Val Ile Leu Leu Leu Arg Val Ile Asp Val Val Met Leu
             20                  25                  30

Leu Gly Ala Ala Trp Leu Ala His Tyr Phe Trp Leu His Asp Ser Val
         35                  40                  45

Ile Asp Gln His Tyr Arg Phe Val Ile Ala Leu Gly Ile Leu Gly Ala
     50                  55                  60

Ile Ile Phe Phe Glu Ile Gly Gln Val Tyr Arg Pro Trp Arg Asn Asp
 65                  70                  75                  80

Ala Met Arg Gly Glu Ile Pro Arg Ile Ile Arg Ala Trp Leu Leu Ala
                 85                  90                  95

Leu Leu Thr Val Val Ser Ile Val Ala Leu Val Arg Leu His Phe Trp
            100                 105                 110

Phe Gly Ser Ser Tyr Arg Trp Ile Ala Ser Trp Gly Gly Leu Gly Leu
        115                 120                 125

Phe Phe Val Leu Ala Ala Arg Gly Val Leu Ala Gln Val Leu Lys Trp
    130                 135                 140
```

-continued

```
Leu Arg Ala Arg Gly Trp Ser Gln Gly Arg Ile Ile Leu Val Gly Leu
145                 150                 155                 160

Asn Gln Met ala Val Ala Val Ser Arg Gln Leu Asn His Ser Ser Trp
                165                 170                 175

Ala Gly Leu Gln Val Ile Gly Tyr Val Asp Asp Arg Ala Glu Asp Arg
            180                 185                 190

Leu Ala Val Ala Asp Tyr Ser Leu Pro Arg Leu Gly Lys Leu Ser Asp
        195                 200                 205

Leu Pro Arg Leu Val Ser Arg Gln Ala Val Asp Glu Val Trp Val Ala
    210                 215                 220

Phe Pro Gly Ala Ser Leu Ala Glu Arg Val Gln His Glu Leu Arg His
225                 230                 235                 240

Leu Pro Val Ser Ile Arg Leu Val Ile Asp Cys Phe Ala Phe Lys Gln
                245                 250                 255

Ser Lys Phe Leu Ser Leu Asn Thr Val Ala Gly Ile Pro Thr Leu Asp
            260                 265                 270

Val Ser Val Ser Pro Leu His Gly Val Asn Arg Tyr Ile Lys Glu Ile
        275                 280                 285

Glu Asp Arg Leu Leu Ala Leu Leu Leu Leu Leu Leu Ile Ser Pro Leu
    290                 295                 300

Met Leu Val Ile Ala Leu Gly Val Lys Leu Ser Ser Pro Gly Pro Val
305                 310                 315                 320

Phe Tyr Lys Gln Val Arg Val Gly Trp Asn Asn Arg Lys Phe Thr Met
                325                 330                 335

Leu Lys Phe Arg Ser Met Pro Val Asp Ala Glu Ala Lys Thr Gly Ala
            340                 345                 350

Val Trp Ala Arg Pro Gly Glu Asn Arg Ala Thr Arg Phe Gly Ala Phe
        355                 360                 365

Leu Arg Lys Thr Ser Leu Asp Glu Leu Pro Gln Leu Ile Asn Val Leu
    370                 375                 380

Lys Gly Asp Met Ser Leu Val Gly Pro Arg Pro Glu Arg Pro Asp Phe
385                 390                 395                 400

Val Glu Val Phe Lys Asp Gln Val Pro Asn Tyr Met Lys Lys His Met
                405                 410                 415

Val Lys Ala Gly Ile Thr Gly Trp Ala Gln Val Asn Gly Trp Arg Gly
            420                 425                 430

Asp Thr Asp Leu Asn Arg Arg Ile Glu His Asp Leu Tyr Tyr Ile Gln
        435                 440                 445

His Trp Ser Val Trp Phe Asp Leu Glu Ile Ala Phe Arg Thr Val Leu
    450                 455                 460

Thr Gly Phe Ile Asn Lys Asn Ala Tyr
465                 470
```

<210> SEQ ID NO 25
<211> LENGTH: 1098
<212> TYPE: DNA
<213> ORGANISM: Methylomonas 16a

<400> SEQUENCE: 25

```
atgtttagac taattcccat catgctggtt ttactgttgc caggctgttt cctggcaccg      60

ggtatggata tgcagaccga tggcgacttg acagaaatcg agctgccaac catgaagggc     120

gggcagttgg tcaaggagaa aacccgcatt cagccgatca ccgccgattt gatcatcgag     180

cgtgaagtcg cacggcggca agccgtcaac aatctaccgc cgatggacga aacccggacc     240
```

-continued

```
agttatcgca tcggtccgca ggacaggttg caaatcacgg tatgggagca tcccgaactg    300

aacgatcccg gcggcgagaa aatcctgccg gaactggccg gcaaggtcgt ggacgataac    360

ggcgatttgt attaccccta tgtcggtacc cttcatgtcg gcggcaagac cgtcaccgaa    420

gtgcgcgagg aattgacccg cgaactgtcc aaatacttca aaaaggtcaa actcgacatt    480

cgtgtgctgt cgttccaggc tcaccgcgtc gcggtggtcg gtgaagtcag aaatcccggc    540

atcgtcgcga tgaccgaaac gccgttgacg gtggcagaag ccatcagcag ggccggcggc    600

gccacgcaag attccgattt gaacaacgtc gcgctggccc gcggcggccg gttgtacaaa    660

ctggatgtgc aagccttgta tgaaaaaggc ctgaccacgc aaaacctgct gttgcgggat    720

ggcgatgtgc tgaacgtcgg cgatcagaaa gacagcaagg tttatgtgat gggcgaggtc    780

ggccggcagc aggccatcca gatcaacaag ggccggatga gtctggctca ggcgctggcc    840

gaagcctatg gcgtcgattt caacacctcg cgtcccggcg atatttacgt gctgcgcgcc    900

ggcgacatgc agccggagat tttccagctg gacgccgaat cgcccgacgc gatgatcctg    960

gccgagcaat tcccgttgca gccgcacgac acgctattcg tcggtacggc cggggtcacg   1020

caatggtcca gggtgctgaa tcagattctg ccgggttcgt ttaccgccat catgtcgcaa   1080

gccgcgatga tggggatg                                                 1098
```

<210> SEQ ID NO 26
<211> LENGTH: 366
<212> TYPE: PRT
<213> ORGANISM: Methylomonas 16a

<400> SEQUENCE: 26

```
Met Phe Arg Leu Ile Pro Ile Met Leu Val Leu Leu Leu Pro Gly Cys
  1               5                  10                  15

Phe Leu Ala Pro Gly Met Asp Met Gln Thr Asp Gly Asp Leu Thr Glu
             20                  25                  30

Ile Glu Leu Pro Thr Met Lys Gly Gly Gln Leu Val Lys Glu Lys Thr
         35                  40                  45

Arg Ile Gln Pro Ile Thr Ala Asp Leu Ile Ile Glu Arg Glu Val Ala
     50                  55                  60

Arg Arg Gln Ala Val Asn Asn Leu Pro Pro Met Asp Glu Thr Arg Thr
 65                  70                  75                  80

Ser Tyr Arg Ile Gly Pro Gln Asp Arg Leu Gln Ile Thr Val Trp Glu
                 85                  90                  95

His Pro Glu Leu Asn Asp Pro Gly Gly Glu Lys Ile Leu Pro Glu Leu
            100                 105                 110

Ala Gly Lys Val Val Asp Asp Asn Gly Asp Leu Tyr Tyr Pro Tyr Val
        115                 120                 125

Gly Thr Leu His Val Gly Gly Lys Thr Val Thr Glu Val Arg Glu Glu
    130                 135                 140

Leu Thr Arg Glu Leu Ser Lys Tyr Phe Lys Lys Val Lys Leu Asp Ile
145                 150                 155                 160

Arg Val Leu Ser Phe Gln Ala His Arg Val Ala Val Val Gly Glu Val
                165                 170                 175

Arg Asn Pro Gly Ile Val Ala Met Thr Glu Thr Pro Leu Thr Val Ala
            180                 185                 190

Glu Ala Ile Ser Arg Ala Gly Gly Ala Thr Gln Asp Ser Asp Leu Asn
        195                 200                 205

Asn Val Ala Leu Ala Arg Gly Gly Arg Leu Tyr Lys Leu Asp Val Gln
```

-continued

```
    210                 215                 220

Ala Leu Tyr Glu Lys Gly Leu Thr Thr Gln Asn Leu Leu Leu Arg Asp
225                 230                 235                 240

Gly Asp Val Leu Asn Val Gly Asp Gln Lys Asp Ser Lys Val Tyr Val
                245                 250                 255

Met Gly Glu Val Gly Arg Gln Gln Ala Ile Gln Ile Asn Lys Gly Arg
            260                 265                 270

Met Ser Leu Ala Gln Ala Leu Ala Glu Ala Tyr Gly Val Asp Phe Asn
        275                 280                 285

Thr Ser Arg Pro Gly Asp Ile Tyr Val Leu Arg Ala Gly Asp Met Gln
    290                 295                 300

Pro Glu Ile Phe Gln Leu Asp Ala Glu Ser Pro Asp Ala Met Ile Leu
305                 310                 315                 320

Ala Glu Gln Phe Pro Leu Gln Pro His Asp Thr Leu Phe Val Gly Thr
                325                 330                 335

Ala Gly Val Thr Gln Trp Ser Arg Val Leu Asn Gln Ile Leu Pro Gly
            340                 345                 350

Ser Phe Thr Ala Ile Met Ser Gln Ala Ala Met Met Gly Met
        355                 360                 365


<210> SEQ ID NO 27
<211> LENGTH: 2337
<212> TYPE: DNA
<213> ORGANISM: Methylomonas 16a

<400> SEQUENCE: 27

atgccgccct tgaatcccgt gatgatgcag gagcctggcg tcagcatccg cgattatgtc      60

gatctgttga tcgagggcaa gaagacaata ctgttgacgt tggccatcgt gctgagcgtg     120

acgatgattt atttggtttt ggccccgcgc acttacaagg ccgatgcctt gctgcgtatc     180

gacaaaaata aagccttgtt ggcggccaat ttgcgtagcg agggcaatgg tacgccaacg     240

gaggcggaaa accccagggc gcaacgggaa gtggaaattt tgcgctcgcg ttcggtgctg     300

ggcaaggtgg tggaggattt gaatctagtc gtggaggcgt cgccacgata ctttcccatc     360

atcggcgaaa ccctggcccg caagcacgac aaacatgagg gcgtagccgg cgcctggtgg     420

ggattcagcc gttgggcctg gggcggggaa aaactgaaaa tcgagcgttt cgaggtgccc     480

gatcgttacc tggacaaggc ttttactttg gtggcgctgg aagcagggcg ttttcaatta     540

ttgagcccta agggcgaggt gctggccgaa ggtttgctcg gtgaaacgct gaccgccgac     600

atcggcgaag ccagtcccgt cgtcgtcaac gtcgctgatt tgcaggcgca ttacggcacc     660

gagttcgagt tgcggcgcaa aacctcgctg gcggccatag aaaccctgca aaaagccttt     720

tcggtcaagg aagtgtccaa ggataccaat attctgagtg tcgaactcaa ggggcgcgat     780

cccgagcaat tggccaaatc ggtcaacgac atcgccagta tttacgtcaa cgccacggtg     840

aattgggaat cggcggaagc ctcgcaaaag ctgaatttcc tggagagcca gttgccgctg     900

gtgaaggaga atctggaaaa ggctgagcaa gccttgagcg cttaccggca gcaacatggc     960

gcggtggata tttccgccga agccgaaatc ctgctgaaac aggcctcgga aatggaaacc    1020

ttgagcatac aactcaagca aaagtacgac gagcaaagcc agcgtctgga atcggagcat    1080

ccggacatga tcgccaccaa tgcgcaaatc cgccgggtga gcaataaatt ggcggccttg    1140

gaaaagcgca tcaaggactt gccgaagacg cagcaaaaca tggtcagcct gtcgcgcgat    1200

gtgcaggtca ataccgagct ttacacctcg ttgctgaaca gcgcgcagga gcaacgcatc    1260
```

-continued

```
gccgcggccg gttccctggg taattcgcgc atcgtcgatt tcgcggtggt tccggaaaaa   1320

ccttattggc ccaagcccgg tttgctgttg gcgattgccg gtttgctggg catcagtctg   1380

ggttcggcgc tgatattcct gagacattcg ttgcagcgcc atgacaatta tccggccttg   1440

ctggaatacc aggtcggctt gccgctgttc gccgccattc cgcacagcaa gaaacaaaga   1500

cgcttggcac gcctgctgga tcagggcaag gagcgggata ccgcgattct ggtcagccac   1560

gatccgctgg atatttcggt cgaatccttg cgcggcttgc gcactacgct ggaagcgacg   1620

ctggccagcg atgaaagcaa ggtcatcatg gtcagcagtc cggcgccggg catgggtaaa   1680

tccttcatca gcaccaattt ggcggctctg ttggccagca tacgcaagcg ggtgctgatc   1740

atcgacgccg acatgcgcaa cggccgcctg catgaaacct ttgccattgc caagcaaccg   1800

ggcttgtccg atctgctgtc cggcaaggtc agcctgggcg acgtgatcgt cagtttgccg   1860

gagataggcg tggatttgat tcccaggggc gagatggtgc tgaatccggc cgaattgttg   1920

gtgctgggcg atctggccga taccttggag caactgaaga gcttttacaa ccatatcgtc   1980

atcgattcgc cgccgatctt gggcgccacc gacgcggcga tcatgggcaa gcattgcgat   2040

gctaccttcc tggtggtcaa ggagggccgt tataccgcgc aagagctgga ggtcagtttc   2100

aggcgcttgc agcaagtcgg cgtgaaaccc aacggtttca tcatcaacga catgaaggaa   2160

ggttcgtcct attacccgta ctacggctat gcctatcagc gggatgacat gcgacaaaaa   2220

caaaccacgg cttggcaggc gcgctttcaa aacctgaatg actggatggg gcggcaggac   2280

gccgagtatt tacccgtcgc cgacgacgcg gaagaacttc acgacagcat cagggcc      2337
```

<210> SEQ ID NO 28
<211> LENGTH: 779
<212> TYPE: PRT
<213> ORGANISM: Methylomonas 16a

<400> SEQUENCE: 28

```
Met Pro Pro Leu Asn Pro Val Met Met Gln Glu Pro Gly Val Ser Ile
  1               5                  10                  15

Arg Asp Tyr Val Asp Leu Leu Ile Glu Gly Lys Lys Thr Ile Leu Leu
             20                  25                  30

Thr Leu Ala Ile Val Leu Ser Val Thr Met Ile Tyr Leu Val Leu Ala
         35                  40                  45

Pro Arg Thr Tyr Lys Ala Asp Ala Leu Leu Arg Ile Asp Lys Asn Lys
     50                  55                  60

Ala Leu Leu Ala Ala Asn Leu Arg Ser Glu Gly Asn Gly Thr Pro Thr
 65                  70                  75                  80

Glu Ala Glu Asn Pro Arg Ala Gln Arg Glu Val Glu Ile Leu Arg Ser
                 85                  90                  95

Arg Ser Val Leu Gly Lys Val Val Glu Asp Leu Asn Leu Val Val Glu
            100                 105                 110

Ala Ser Pro Arg Tyr Phe Pro Ile Ile Gly Glu Thr Leu Ala Arg Lys
        115                 120                 125

His Asp Lys His Glu Gly Val Ala Gly Ala Trp Trp Gly Phe Ser Arg
    130                 135                 140

Trp Ala Trp Gly Gly Glu Lys Leu Lys Ile Glu Arg Phe Glu Val Pro
145                 150                 155                 160

Asp Arg Tyr Leu Asp Lys Ala Phe Thr Leu Val Ala Leu Glu Ala Gly
                165                 170                 175

Arg Phe Gln Leu Leu Ser Pro Lys Gly Glu Val Leu Ala Glu Gly Leu
            180                 185                 190
```

-continued

```
Leu Gly Glu Thr Leu Thr Ala Asp Ile Gly Glu Ala Ser Pro Val Val
        195                 200                 205

Val Asn Val Ala Asp Leu Gln Ala His Tyr Gly Thr Glu Phe Glu Leu
    210                 215                 220

Arg Arg Lys Thr Ser Leu Ala Ala Ile Glu Thr Leu Gln Lys Ala Phe
225                 230                 235                 240

Ser Val Lys Glu Val Ser Lys Asp Thr Asn Ile Leu Ser Val Glu Leu
                245                 250                 255

Lys Gly Arg Asp Pro Glu Gln Leu Ala Lys Ser Val Asn Asp Ile Ala
            260                 265                 270

Ser Ile Tyr Val Asn Ala Thr Val Asn Trp Glu Ser Ala Glu Ala Ser
        275                 280                 285

Gln Lys Leu Asn Phe Leu Glu Ser Gln Leu Pro Leu Val Lys Glu Asn
    290                 295                 300

Leu Glu Lys Ala Glu Gln Ala Leu Ser Ala Tyr Arg Gln Gln His Gly
305                 310                 315                 320

Ala Val Asp Ile Ser Ala Glu Ala Glu Ile Leu Leu Lys Gln Ala Ser
                325                 330                 335

Glu Met Glu Thr Leu Ser Ile Gln Leu Lys Gln Lys Tyr Asp Glu Gln
            340                 345                 350

Ser Gln Arg Leu Glu Ser Glu His Pro Asp Met Ile Ala Thr Asn Ala
        355                 360                 365

Gln Ile Arg Arg Val Ser Asn Lys Leu Ala Ala Leu Glu Lys Arg Ile
    370                 375                 380

Lys Asp Leu Pro Lys Thr Gln Gln Asn Met Val Ser Leu Ser Arg Asp
385                 390                 395                 400

Val Gln Val Asn Thr Glu Leu Tyr Thr Ser Leu Leu Asn Ser Ala Gln
                405                 410                 415

Glu Gln Arg Ile Ala Ala Ala Gly Ser Leu Gly Asn Ser Arg Ile Val
            420                 425                 430

Asp Phe Ala Val Val Pro Glu Lys Pro Tyr Trp Pro Lys Pro Gly Leu
        435                 440                 445

Leu Leu Ala Ile Ala Gly Leu Leu Gly Ile Ser Leu Gly Ser Ala Leu
    450                 455                 460

Ile Phe Leu Arg His Ser Leu Gln Arg His Asp Asn Tyr Pro Ala Leu
465                 470                 475                 480

Leu Glu Tyr Gln Val Gly Leu Pro Leu Phe Ala Ala Ile Pro His Ser
                485                 490                 495

Lys Lys Gln Arg Arg Leu Ala Arg Leu Leu Asp Gln Gly Lys Glu Arg
            500                 505                 510

Asp Thr Ala Ile Leu Val Ser His Asp Pro Leu Asp Ile Ser Val Glu
        515                 520                 525

Ser Leu Arg Gly Leu Arg Thr Thr Leu Glu Ala Thr Leu Ala Ser Asp
    530                 535                 540

Glu Ser Lys Val Ile Met Val Ser Ser Pro Ala Pro Gly Met Gly Lys
545                 550                 555                 560

Ser Phe Ile Ser Thr Asn Leu Ala Ala Leu Leu Ala Ser Ile Arg Lys
                565                 570                 575

Arg Val Leu Ile Ile Asp Ala Asp Met Arg Asn Gly Arg Leu His Glu
            580                 585                 590

Thr Phe Ala Ile Ala Lys Gln Pro Gly Leu Ser Asp Leu Leu Ser Gly
        595                 600                 605
```

-continued

```
Lys Val Ser Leu Gly Asp Val Ile Val Ser Leu Pro Glu Ile Gly Val
    610                 615                 620

Asp Leu Ile Pro Arg Gly Glu Met Val Leu Asn Pro Ala Glu Leu Leu
625                 630                 635                 640

Val Leu Gly Asp Leu Ala Asp Thr Leu Glu Gln Leu Lys Ser Phe Tyr
                645                 650                 655

Asn His Ile Val Ile Asp Ser Pro Pro Ile Leu Gly Ala Thr Asp Ala
            660                 665                 670

Ala Ile Met Gly Lys His Cys Asp Ala Thr Phe Leu Val Val Lys Glu
        675                 680                 685

Gly Arg Tyr Thr Ala Gln Glu Leu Glu Val Ser Phe Arg Arg Leu Gln
    690                 695                 700

Gln Val Gly Val Lys Pro Asn Gly Phe Ile Ile Asn Asp Met Lys Glu
705                 710                 715                 720

Gly Ser Ser Tyr Tyr Pro Tyr Tyr Gly Tyr Ala Tyr Gln Arg Asp Asp
                725                 730                 735

Met Arg Gln Lys Gln Thr Thr Ala Trp Gln Ala Arg Phe Gln Asn Leu
            740                 745                 750

Asn Asp Trp Met Gly Arg Gln Asp Ala Glu Tyr Leu Pro Val Ala Asp
        755                 760                 765

Asp Ala Glu Glu Leu His Asp Ser Ile Arg Ala
    770                 775
```

```
<210> SEQ ID NO 29
<211> LENGTH: 1416
<212> TYPE: DNA
<213> ORGANISM: Methylomonas 16a

<400> SEQUENCE: 29

atgttgggca aagggcattc ggacaaggct aatttaaagg aaggtttcat gctggattgg      60

ttgaggcaaa agaacttgtt gggtgacgcc tgttgggcgc tggcgggaca gttattgtcg     120

gcactggctt tgcttgcggg cacgcgcatc ctgaccgaat tggtgacgcc ggcggttttc     180

gggcacgtgg cgttgctgaa tggcttcgtc gcgctggggg tggcggtgtt tgcctatccc     240

ttcatctgcg ccgggatgcg tttcaccaat gaatgccgaa atttccgcga gcgggcggca     300

ttgcatggat tggtgtttgc gctgacgacg cgatcgacgg cattggccat taccttgctg     360

ctgctgggcg gcgcgctgta ttgctatttt gtcggtagtg aaatcggctt gttcgtgttg     420

accggattgc tgttagccgt caccgttcgc cgcgagttgg gcattcagct gatgataggc     480

gaacgcaagc aacgcggcgc cgcgctttgg caaaccagcg acagcatcct gcggccggtg     540

atggcgattt ggctggtatg ggtttggggg caaagtccgg aagcggtgtt gttgggctat     600

gtctgtgcca gcgtgctggc caatacgctg tggacgatcg taagcgatgc atggcaaaaa     660

aagcctaccg gcgatcgcgg cttcctgggg cggcaattcg agcgcggcct ttgggcttat     720

gccttgccgt tgatcccgat ggaattgatg ttctggctca acggcctggg cgaccgttac     780

gtgatcggtt atttcctaac ggcggctgaa gtgggggtgt acgcggccgc ttatacgctg     840

gtcaacgaag ccttcaatcg tagcgcgatg gtgttgttgc gcacgtttca gccggcctat     900

tttcaagcgg tttcccaagg caaaagcaaa gatgcatgtt cgctgctatg gctgtggata     960

ggggcggtcg tcgtgatgag tgttctgggc gtgacgctgg tctggttgtg caaggactgg    1020

ctggtcgcag gcttgttggc agaaccctat catgcggccg gcgcgctgat gccggttatc    1080

gccgcgggca cggccttgca tgccctgggc accgtgatgt cccagccgct gctggcgaga    1140
```

-continued

```
aaacgcacgc cgatcttgct gcgcgggcgt atctgtgggg cgttggcggc gctcatcacg   1200

ctgcctttgc tggtggcgca ttttggcctg ttcggggcgg ccttggccaa tcccgtatat   1260

ttcggcatcg aagcgctggt gttggccttg ctggccaagc cctggcgcaa gctccgcacg   1320

ggacggcagg cgcggatcgt tcaatccgaa gcggcgatgc ccgaacccga ctttgacgcc   1380

atcggagtga gagcggcggc gttctccaac gaatcc                             1416
```

<210> SEQ ID NO 30
<211> LENGTH: 472
<212> TYPE: PRT
<213> ORGANISM: Methylomonas 16a

<400> SEQUENCE: 30

```
Met Leu Gly Lys Gly His Ser Asp Lys Ala Asn Leu Lys Glu Gly Phe
  1               5                  10                  15

Met Leu Asp Trp Leu Arg Gln Lys Asn Leu Leu Gly Asp Ala Cys Trp
             20                  25                  30

Ala Leu Ala Gly Gln Leu Leu Ser Ala Leu Ala Leu Leu Ala Gly Thr
         35                  40                  45

Arg Ile Leu Thr Glu Leu Val Thr Pro Ala Val Phe Gly His Val Ala
     50                  55                  60

Leu Leu Asn Gly Phe Val Ala Leu Gly Val Ala Val Phe Ala Tyr Pro
 65                  70                  75                  80

Phe Ile Cys Ala Gly Met Arg Phe Thr Asn Glu Cys Arg Asn Phe Arg
                 85                  90                  95

Glu Arg Ala Ala Leu His Gly Leu Val Phe Ala Leu Thr Thr Arg Ser
            100                 105                 110

Thr Ala Leu Ala Ile Thr Leu Leu Leu Leu Gly Gly Ala Leu Tyr Cys
        115                 120                 125

Tyr Phe Val Gly Ser Glu Ile Gly Leu Phe Val Leu Thr Gly Leu Leu
    130                 135                 140

Leu Ala Val Thr Val Arg Arg Glu Leu Gly Ile Gln Leu Met Ile Gly
145                 150                 155                 160

Glu Arg Lys Gln Arg Gly Ala Ala Leu Trp Gln Thr Ser Asp Ser Ile
                165                 170                 175

Leu Arg Pro Val Met ala Ile Trp Leu Val Trp Gly Leu Gly Gln Ser
            180                 185                 190

Pro Glu Ala Val Leu Leu Gly Tyr Val Cys Ala Ser Val Leu Ala Asn
        195                 200                 205

Thr Leu Trp Thr Ile Val Ser Asp Ala Trp Gln Lys Lys Pro Thr Gly
    210                 215                 220

Asp Arg Gly Phe Leu Gly Arg Gln Phe Glu Arg Gly Leu Trp Ala Tyr
225                 230                 235                 240

Ala Leu Pro Leu Ile Pro Met Glu Leu Met Phe Trp Leu Asn Gly Leu
                245                 250                 255

Gly Asp Arg Tyr Val Ile Gly Tyr Phe Leu Thr Ala Ala Glu Val Gly
            260                 265                 270

Val Tyr Ala Ala Ala Tyr Thr Leu Val Asn Glu Ala Phe Asn Arg Ser
        275                 280                 285

Ala Met Val Leu Leu Arg Thr Phe Gln Pro Ala Tyr Phe Gln Ala Val
    290                 295                 300

Ser Gln Gly Lys Ser Lys Asp Ala Cys Ser Leu Leu Trp Leu Trp Ile
305                 310                 315                 320

Gly Ala Val Val Val Met Ser Val Leu Gly Val Thr Leu Val Trp Leu
```

-continued

```
                325                 330                 335

Cys Lys Asp Trp Leu Val Ala Gly Leu Leu Ala Glu Pro Tyr His Ala
            340                 345                 350

Ala Gly Ala Leu Met Pro Val Ile Ala Ala Gly Thr Ala Leu His Ala
        355                 360                 365

Leu Gly Thr Val Met Ser Gln Pro Leu Leu Ala Arg Lys Arg Thr Pro
    370                 375                 380

Ile Leu Leu Arg Gly Arg Ile Cys Gly Ala Leu Ala Ala Leu Ile Thr
385                 390                 395                 400

Leu Pro Leu Leu Val Ala His Phe Gly Leu Phe Gly Ala Ala Leu Ala
                405                 410                 415

Asn Pro Val Tyr Phe Gly Ile Glu Ala Leu Val Leu Ala Leu Leu Ala
            420                 425                 430

Lys Pro Trp Arg Lys Leu Arg Thr Gly Arg Gln Ala Arg Ile Val Gln
        435                 440                 445

Ser Glu Ala Ala Met Pro Glu Pro Asp Phe Asp Ala Ile Gly Val Arg
    450                 455                 460

Ala Ala Ala Phe Ser Asn Glu Ser
465                 470


<210> SEQ ID NO 31
<211> LENGTH: 816
<212> TYPE: DNA
<213> ORGANISM: Methylomonas 16a

<400> SEQUENCE: 31

ccgataaaca ggtgtgaacc attgaacagc ttgaccatag tcattttgac gctgaacgag      60

gccgccaatc tgccccggtg cctggcggcg attccgcaac gttaccctgt cgtgatcttg     120

gattccggga gcagcgatga cacgctgtcg atcgcggaag gccacggctg caagatttat     180

caaaatcctt ggcccggctt tgccgagcag cgcaattttg cgttgaatca atgcgatatc     240

gagacgccgt gggtgttgtt cgtcgatgcc gacgaaatct acccgcaagt cttttatcag     300

catttcgaca gtggaatgct gcaaaccgga gagatcgatg tgctgatggt gccgtccatt     360

ttgtttttgc gcggcaaacg cctgcatcat gcgccgggtt atccgatcta tcacccgcgc     420

ctggttcggc gggaaacgac ccgcttcgtg cgtaatcata ccggtcacgg cgaggccgtc     480

atggatagtt gccgcatcgg ctacaccgat attccctatg atcattactt ttacgacggc     540

gagatcatcc agtggatgca taagcatgtc gacaaagccg ctcaggaagt tcggctcaaa     600

ccgacccagg gcgcgttgat gacgacccgc gggcgcttga gcgtaatgct ggggcgttca     660

tggagccgaa tcctggccag gtttgtttac cactatctgc tgcgcggcgg ctttttggac     720

ggcgcggcgg gattggaatt tacgctgatg tttacctggt atgaagccag catctatctg     780

caagccaaag ccgctgcaca agcaagggga acagca                               816


<210> SEQ ID NO 32
<211> LENGTH: 272
<212> TYPE: PRT
<213> ORGANISM: Methylomonas 16a

<400> SEQUENCE: 32

Pro Ile Asn Arg Cys Glu Pro Leu Asn Ser Leu Thr Ile Val Ile Leu
  1               5                  10                  15

Thr Leu Asn Glu Ala Ala Asn Leu Pro Arg Cys Leu Ala Ala Ile Pro
             20                  25                  30
```

-continued

```
Gln Arg Tyr Pro Val Val Ile Leu Asp Ser Gly Ser Ser Asp Asp Thr
         35                  40                  45

Leu Ser Ile Ala Glu Gly His Gly Cys Lys Ile Tyr Gln Asn Pro Trp
     50                  55                  60

Pro Gly Phe Ala Glu Gln Arg Asn Phe Ala Leu Asn Gln Cys Asp Ile
 65                  70                  75                  80

Glu Thr Pro Trp Val Leu Phe Val Asp Ala Asp Glu Ile Tyr Pro Gln
                 85                  90                  95

Val Phe Tyr Gln His Phe Asp Ser Gly Met Leu Gln Thr Gly Glu Ile
            100                 105                 110

Asp Val Leu Met Val Pro Ser Ile Leu Phe Leu Arg Gly Lys Arg Leu
        115                 120                 125

His His Ala Pro Gly Tyr Pro Ile Tyr His Pro Arg Leu Val Arg Arg
    130                 135                 140

Glu Thr Thr Arg Phe Val Arg Asn His Thr Gly His Gly Glu Ala Val
145                 150                 155                 160

Met Asp Ser Cys Arg Ile Gly Tyr Thr Asp Ile Pro Tyr Asp His Tyr
                165                 170                 175

Phe Tyr Asp Gly Glu Ile Ile Gln Trp Met His Lys His Val Asp Lys
            180                 185                 190

Ala Ala Gln Glu Val Arg Leu Lys Pro Thr Gln Gly Ala Leu Met Thr
        195                 200                 205

Thr Arg Gly Arg Leu Ser Val Met Leu Gly Arg Ser Trp Ser Arg Ile
    210                 215                 220

Leu Ala Arg Phe Val Tyr His Tyr Leu Leu Arg Gly Gly Phe Leu Asp
225                 230                 235                 240

Gly Ala Ala Gly Leu Glu Phe Thr Leu Met Phe Thr Trp Tyr Glu Ala
                245                 250                 255

Ser Ile Tyr Leu Gln Ala Lys Ala Ala Gln Ala Arg Gly Thr Ala
            260                 265                 270
```

<210> SEQ ID NO 33
<211> LENGTH: 852
<212> TYPE: DNA
<213> ORGANISM: Methylomonas 16a

<400> SEQUENCE: 33

```
atgaaagtgt cattgatatt ggctacgctc ggcagggacc tggaactgct ggattttttg      60

aaatccttgc tgtttcagac ctacaagaac ttcgagttga tcgtcatcga ccagaatcaa     120

gacggcaaaa tcgatcggat tgccgagcaa tatagccaat gcctcgatct gaaacacgtc     180

aaggtgaatt tcaccggtaa tgcccgagcc agggatcatg gcatcgcctt ggcccagggc     240

gacatcatcg cctttccgga cgatgattgc gtgtatgaaa aggatgtgct ggaaaaagtg     300

gtaggcgaat ttgcatgcca gccaacgttg tcgattctgg tagccgggtc ctacgatttt     360

tccgcgaaac acttcagcat aggcgtcaac agccgtaaag cgcgttattt ttcccggttg     420

aacatgatgg gggtggagtt cacgcagttt tttgcgctgg cgcgtatcga caggcggcag     480

ttttatttgg accacgattt cggcatcggc tccaaatatg ccggggcgga aggcttcgag     540

ttgctgtatc gcctgctgcg cgcgggcggg cgggcgttct acaagccgga tatcaaaatc     600

tatcacgcca acaaggacca ttacacgctg ggtaccgcgc gcatgctgaa atattccacc     660

ggtattggcg cctatatccg caaattcgcc aatcagcatg atccctatat cggctattac     720

atcctgcgca agatgctgat agccccgact ctgaaaatgc tgctggcctt gttgacgttc     780
```

-continued

```
aacccgggaa aactcgccta ttcgttttat aacctggtgg gcatatggcg cggatttttt    840

gcctatgggc gc                                                        852


<210> SEQ ID NO 34
<211> LENGTH: 284
<212> TYPE: PRT
<213> ORGANISM: Methylomonas 16a

<400> SEQUENCE: 34

Met Lys Val Ser Leu Ile Leu Ala Thr Leu Gly Arg Asp Leu Glu Leu
  1               5                  10                  15

Leu Asp Phe Leu Lys Ser Leu Leu Phe Gln Thr Tyr Lys Asn Phe Glu
             20                  25                  30

Leu Ile Val Ile Asp Gln Asn Gln Asp Gly Lys Ile Asp Arg Ile Ala
         35                  40                  45

Glu Gln Tyr Ser Gln Cys Leu Asp Leu Lys His Val Lys Val Asn Phe
     50                  55                  60

Thr Gly Asn Ala Arg Ala Arg Asp His Gly Ile Ala Leu Ala Gln Gly
 65                  70                  75                  80

Asp Ile Ile Ala Phe Pro Asp Asp Asp Cys Val Tyr Glu Lys Asp Val
                 85                  90                  95

Leu Glu Lys Val Val Gly Glu Phe Ala Cys Gln Pro Thr Leu Ser Ile
            100                 105                 110

Leu Val Ala Gly Ser Tyr Asp Phe Ser Ala Lys His Phe Ser Ile Gly
        115                 120                 125

Val Asn Ser Arg Lys Ala Arg Tyr Phe Ser Arg Leu Asn Met Met Gly
    130                 135                 140

Val Glu Phe Thr Gln Phe Phe Ala Leu Ala Arg Ile Asp Arg Arg Gln
145                 150                 155                 160

Phe Tyr Leu Asp His Asp Phe Gly Ile Gly Ser Lys Tyr Ala Gly Ala
                165                 170                 175

Glu Gly Phe Glu Leu Leu Tyr Arg Leu Leu Arg Ala Gly Gly Arg Ala
            180                 185                 190

Phe Tyr Lys Pro Asp Ile Lys Ile Tyr His Ala Asn Lys Asp His Tyr
        195                 200                 205

Thr Leu Gly Thr Ala Arg Met Leu Lys Tyr Ser Thr Gly Ile Gly Ala
    210                 215                 220

Tyr Ile Arg Lys Phe Ala Asn Gln His Asp Pro Tyr Ile Gly Tyr Tyr
225                 230                 235                 240

Ile Leu Arg Lys Met Leu Ile Ala Pro Thr Leu Lys Met Leu Leu Ala
                245                 250                 255

Leu Leu Thr Phe Asn Pro Gly Lys Leu Ala Tyr Ser Phe Tyr Asn Leu
            260                 265                 270

Val Gly Ile Trp Arg Gly Phe Phe Ala Tyr Gly Arg
        275                 280


<210> SEQ ID NO 35
<211> LENGTH: 1194
<212> TYPE: DNA
<213> ORGANISM: Methylomonas 16a

<400> SEQUENCE: 35

atggaactgg gtattgtgac gacacatgta ccgccggcca agggctacgg tggcgtctcg     60

gtgacttgcg gcgtcttgac cagggcgtgg gcggaaatgg ggctagagat ggcgctggtt    120

tcgtcggatg aatccatcga tgggtgcttg aaaccggcgg acgtcaagct gggcgcaagc    180
```

-continued

```
gtggatgtcg atttgtaccg ctgttatggc ttcaggcgct ggggggttcgg cttgggagcg    240

atacccagcc tgctgcgcct gtgctggcaa gccccgctcg tgtatatcca tggcgtcgcc    300

acctggccgt cgaccttggc ggcgcttttt tgctgcctgc tgcgcaagcc gttcatggtg    360

gcggtgcatg gcggcctgat gcctgagcat gtggcactga tcaagcggaa aaaacggcat    420

aaatggtggt attacaaact gctgactttt ccgaccttgc gccgcgcgat tgccgtgcat    480

tgcaccagtg ataccgaggt tgagggcgtg cgtgacgtac tgggcgaaaa cgcgcgggtg    540

ttgctggtgc ccaacggcat cgacagccgg ggtgtcgagg aggcccctta tccggcaggc    600

gaaggcatgc aactgtgttt tttgggtcac gtgcagcagg aaaagggcat caacgctttc    660

atccgggcct ggctcgaggt ccggcggccg ggcgatcgtc tggtcgtcgc cggccgtagc    720

gtggacgggg attattttgc cgagttttgt tccctggtcg aacgggcaaa cggcgcgatc    780

cgctattgcg gctatctgca gcgtgacgac gtgatggcct tgctggcgca aagtcatttt    840

ctggtattgc cgtccggttt ggagcaggtc ggcggcatgc gggagaattt cggtaacgtg    900

gtggcggaag ccctggcggc gggacggccg gtgctggttg tcaggggctt ggcctgggat    960

catttgccgg cattgaatgc gggcttggtt tttgacaggg acgaggccgc cgtccaagcc   1020

gtgctacgcc gggctcaggc gctcgatcaa gccgactggc tgcgcatgtc gcaagcgggc   1080

cggcgccatg ttcaacagca gctcgatccg gtcaaactgg cggagcgcgt ctggcaagca   1140

atgacggcgg cggtaccggt tgacgaggcc aaggtgttgg ccgaggagcc gaaa         1194
```

```
<210> SEQ ID NO 36
<211> LENGTH: 398
<212> TYPE: PRT
<213> ORGANISM: Methylomonas 16a

<400> SEQUENCE: 36

Met Glu Leu Gly Ile Val Thr Thr His Val Pro Pro Ala Lys Gly Tyr
  1               5                  10                  15

Gly Gly Val Ser Val Thr Cys Gly Val Leu Thr Arg Ala Trp Ala Glu
             20                  25                  30

Met Gly Leu Glu Met ala Leu Val Ser Ser Asp Glu Ser Ile Asp Gly
         35                  40                  45

Cys Leu Lys Pro Ala Asp Val Lys Leu Gly Ala Ser Val Asp Val Asp
     50                  55                  60

Leu Tyr Arg Cys Tyr Gly Phe Arg Arg Trp Gly Phe Gly Leu Gly Ala
 65                  70                  75                  80

Ile Pro Ser Leu Leu Arg Leu Cys Trp Gln Ala Pro Leu Val Tyr Ile
                 85                  90                  95

His Gly Val Ala Thr Trp Pro Ser Thr Leu Ala Ala Leu Phe Cys Cys
            100                 105                 110

Leu Leu Arg Lys Pro Phe Met Val Ala Val His Gly Gly Leu Met Pro
        115                 120                 125

Glu His Val Ala Leu Ile Lys Arg Lys Lys Arg His Lys Trp Trp Tyr
    130                 135                 140

Tyr Lys Leu Leu Thr Phe Pro Thr Leu Arg Arg Ala Ile Ala Val His
145                 150                 155                 160

Cys Thr Ser Asp Thr Glu Val Glu Gly Val Arg Asp Val Leu Gly Glu
                165                 170                 175

Asn Ala Arg Val Leu Leu Val Pro Asn Gly Ile Asp Ser Arg Gly Val
            180                 185                 190
```

-continued

```
Glu Glu Ala Pro Tyr Pro Ala Gly Glu Gly Met Gln Leu Cys Phe Leu
        195                 200                 205

Gly His Val Gln Gln Glu Lys Gly Ile Asn Ala Phe Ile Arg Ala Trp
    210                 215                 220

Leu Glu Val Arg Arg Pro Gly Asp Arg Leu Val Val Ala Gly Arg Ser
225                 230                 235                 240

Val Asp Gly Asp Tyr Phe Ala Glu Phe Cys Ser Leu Val Glu Arg Ala
                245                 250                 255

Asn Gly Ala Ile Arg Tyr Cys Gly Tyr Leu Gln Arg Asp Asp Val Met
            260                 265                 270

Ala Leu Leu Ala Gln Ser His Phe Leu Val Leu Pro Ser Gly Leu Glu
        275                 280                 285

Gln Val Gly Gly Met Arg Glu Asn Phe Gly Asn Val Val Ala Glu Ala
    290                 295                 300

Leu Ala Ala Gly Arg Pro Val Leu Val Val Arg Gly Leu Ala Trp Asp
305                 310                 315                 320

His Leu Pro Ala Leu Asn Ala Gly Leu Val Phe Asp Arg Asp Glu Ala
                325                 330                 335

Ala Val Gln Ala Val Leu Arg Arg Ala Gln Ala Leu Asp Gln Ala Asp
            340                 345                 350

Trp Leu Arg Met Ser Gln Ala Gly Arg Arg His Val Gln Gln Gln Leu
        355                 360                 365

Asp Pro Val Lys Leu Ala Glu Arg Val Trp Gln Ala Met Thr Ala Ala
    370                 375                 380

Val Pro Val Asp Glu Ala Lys Val Leu Ala Glu Glu Pro Lys
385                 390                 395
```

<210> SEQ ID NO 37
<211> LENGTH: 951
<212> TYPE: DNA
<213> ORGANISM: Methylomonas 16a

<400> SEQUENCE: 37

```
atgacgcata aggttggact cgtcgtaccc accttgaatg cgggcgcatc ctggcagggc      60

tggctggagg ccctggcggc gcaaagtcga aggccggatc gtttgttgct gatcgattcc     120

tcgtccagcg acgacacggt ggcgctggcc cgtgcgagag gatttgacgc gcatgtgatt     180

gccaaggcct cgttcaacca cggcggcact cgtcaatcgg gcgtcgatat gttggtcgac     240

atggatctga tcgtatttct gacccaggat gccttgttgg ccgaccccag cgcgatcgaa     300

aatctgttgc aggtatttgt caatccgcaa gtggccgcgg cctatggccg gcaattgccg     360

catcggaacg ctggccccat cggcgcgcat gcccggatat tcaattaccc ggcgcaaagc     420

cagttgcgca ccttgcagga ccgcgaccgc ttcggcatca agaccgtgtt catttccaat     480

tcgttcgccg cctacagacg ttgcgccctg atgcaaatcg gcggattccc ggctcacacc     540

attatgaacg aagatactta cgttgccggc aagatgctgt tgtccggctg gagcctcgcc     600

tattgcgccg acgcgcgggt gtttcattcc cacgattaca gcctgctgga agaattcagg     660

cgctatttcg atatcggggt tttccacgcg caaaacccct ggctgcaaca gacctttggc     720

ggcgcctcgg gcgaaggcgc gcgttttgtg ctctccgaaa tgcgttactt gtcgaacacg     780

gcgccctggc tgatgttttc cgcgttcctg agaacgggat tgaaatgggc ggggtataag     840

ctgggcggcc tgcatcgcgg ctggccatta gccctgagca ggcgcctcag cctgcataag     900

ggatattggg tggcaactga acgggaatac cctaatatgc ctggatgccg t              951
```

<210> SEQ ID NO 38
<211> LENGTH: 317
<212> TYPE: PRT
<213> ORGANISM: Methylomonas 16a

<400> SEQUENCE: 38

```
Met Thr His Lys Val Gly Leu Val Val Pro Thr Leu Asn Ala Gly Ala
  1               5                  10                  15

Ser Trp Gln Gly Trp Leu Glu Ala Leu Ala Ala Gln Ser Arg Arg Pro
             20                  25                  30

Asp Arg Leu Leu Leu Ile Asp Ser Ser Ser Ser Asp Asp Thr Val Ala
         35                  40                  45

Leu Ala Arg Ala Arg Gly Phe Asp Ala His Val Ile Ala Lys Ala Ser
     50                  55                  60

Phe Asn His Gly Gly Thr Arg Gln Ser Gly Val Asp Met Leu Val Asp
 65                  70                  75                  80

Met Asp Leu Ile Val Phe Leu Thr Gln Asp Ala Leu Leu Ala Asp Pro
                 85                  90                  95

Ser Ala Ile Glu Asn Leu Leu Gln Val Phe Val Asn Pro Gln Val Ala
            100                 105                 110

Ala Ala Tyr Gly Arg Gln Leu Pro His Arg Asn Ala Gly Pro Ile Gly
        115                 120                 125

Ala His Ala Arg Ile Phe Asn Tyr Pro Ala Gln Ser Gln Leu Arg Thr
    130                 135                 140

Leu Gln Asp Arg Asp Arg Phe Gly Ile Lys Thr Val Phe Ile Ser Asn
145                 150                 155                 160

Ser Phe Ala Ala Tyr Arg Arg Cys Ala Leu Met Gln Ile Gly Gly Phe
                165                 170                 175

Pro Ala His Thr Ile Met Asn Glu Asp Thr Tyr Val Ala Gly Lys Met
            180                 185                 190

Leu Leu Ser Gly Trp Ser Leu Ala Tyr Cys Ala Asp Ala Arg Val Phe
        195                 200                 205

His Ser His Asp Tyr Ser Leu Leu Glu Glu Phe Arg Arg Tyr Phe Asp
    210                 215                 220

Ile Gly Val Phe His Ala Gln Asn Pro Trp Leu Gln Gln Thr Phe Gly
225                 230                 235                 240

Gly Ala Ser Gly Glu Gly Ala Arg Phe Val Leu Ser Glu Met Arg Tyr
                245                 250                 255

Leu Ser Asn Thr Ala Pro Trp Leu Met Phe Ser Ala Phe Leu Arg Thr
            260                 265                 270

Gly Leu Lys Trp Ala Gly Tyr Lys Leu Gly Gly Leu His Arg Gly Trp
        275                 280                 285

Pro Leu Ala Leu Ser Arg Arg Leu Ser Leu His Lys Gly Tyr Trp Val
    290                 295                 300

Ala Thr Glu Arg Glu Tyr Pro Asn Met Pro Gly Cys Arg
305                 310                 315
```

<210> SEQ ID NO 39
<211> LENGTH: 1170
<212> TYPE: DNA
<213> ORGANISM: Methylomonas 16a
<220> FEATURE:
<223> OTHER INFORMATION: ORF1
<223> OTHER INFORMATION: nirF gene

<400> SEQUENCE: 39

-continued

```
atgaagcgat ttttaacgtt ggcaggtgcg gcttattttt ttgccgcatc ggctgttgca      60

gacctgcgcg ccaccggcga tttgggtgtc gtgatcgagc gcgagaccgg cagtgtgcaa     120

gtcatcaaca ccagcacgcc caagatgctg agccgcatcg aaggcctggg cgatttgtct     180

cacgcttcgg tggtgttctc gcgtgatcag cgctatgcct atgtattcgg tcgcgacggc     240

ggcttgagca aaatcgatct gttgcaggac aaaatcgaaa aacgcgtcgt gcaagccggt     300

aacagcatag gcggggcgat ttcccaggat ggcaaagtca tcgccgtatc caactatacg     360

ccgggcggcg tcaagctgtt cgatgccgag accttggagc agttggccga gattccggcc     420

gtttacggcg acgacaacca gttatccaaa gtggtcggct tggtcgatgc accgggcggt     480

cgtttcgttt gcagcctgtt cgaaggtaac gagatttggc tgatagacgc caagaatcca     540

cgccagccgg tcgtcaagaa attcaaggac atcggcaagc ggccttatga tgccttgctg     600

acgccggatg gccatttcta cgcggccgga ctgttcggcg aaaaaggcct ggctttgctg     660

gatttatggc agccggagct aggcgtcaaa cacatcctgg aagactacgg caaggacgac     720

gagcaattgc cggtttacaa aatgccgcat ctggaaggct ggacggtagc cggtgatctg     780

ctgttcgtgc cggccatcgg cctgcatgag gtgttggtga tcgataaaca cgattgggag     840

ctggtcaaac gcattccggt cgtcggacaa cccgtgttcg tgatgtcccg accggatggt     900

cgccaggtgt gggtgaattt cgcctttccg gacaatcaaa ccgtacaggt catagacgtc     960

aaggatttca atatcgtcaa gaccctgcaa ccgggtaagg ccgtgctgca catggagttc    1020

agcccgcgcg gcgaagccgt ctggatggcg gtgcgcgacg aggacagggt aatggtttac    1080

gacacggaca gtttcaacga aaccgcccgt ctaccggcgc aaaagcccag cggcatcttt    1140

ttcagtaatc gcgccaatca gttggggctg                                      1170
```

<210> SEQ ID NO 40
<211> LENGTH: 390
<212> TYPE: PRT
<213> ORGANISM: Methylomonas 16a
<220> FEATURE:
<223> OTHER INFORMATION: NirF

<400> SEQUENCE: 40

```
Met Lys Arg Phe Leu Thr Leu Ala Gly Ala Ala Tyr Phe Phe Ala Ala
  1               5                  10                  15

Ser Ala Val Ala Asp Leu Arg Ala Thr Gly Asp Leu Gly Val Val Ile
             20                  25                  30

Glu Arg Glu Thr Gly Ser Val Gln Val Ile Asn Thr Ser Thr Pro Lys
         35                  40                  45

Met Leu Ser Arg Ile Glu Gly Leu Gly Asp Leu Ser His Ala Ser Val
     50                  55                  60

Val Phe Ser Arg Asp Gln Arg Tyr Ala Tyr Val Phe Gly Arg Asp Gly
 65                  70                  75                  80

Gly Leu Ser Lys Ile Asp Leu Leu Gln Asp Lys Ile Glu Lys Arg Val
                 85                  90                  95

Val Gln Ala Gly Asn Ser Ile Gly Gly Ala Ile Ser Gln Asp Gly Lys
            100                 105                 110

Val Ile Ala Val Ser Asn Tyr Thr Pro Gly Gly Val Lys Leu Phe Asp
        115                 120                 125

Ala Glu Thr Leu Glu Gln Leu Ala Glu Ile Pro Ala Val Tyr Gly Asp
    130                 135                 140

Asp Asn Gln Leu Ser Lys Val Val Gly Leu Val Asp Ala Pro Gly Gly
145                 150                 155                 160
```

-continued

```
Arg Phe Val Cys Ser Leu Phe Glu Gly Asn Glu Ile Trp Leu Ile Asp
                165                 170                 175

Ala Lys Asn Pro Arg Gln Pro Val Val Lys Lys Phe Lys Asp Ile Gly
            180                 185                 190

Lys Arg Pro Tyr Asp Ala Leu Leu Thr Pro Asp Gly His Phe Tyr Ala
        195                 200                 205

Ala Gly Leu Phe Gly Glu Lys Gly Leu Ala Leu Leu Asp Leu Trp Gln
    210                 215                 220

Pro Glu Leu Gly Val Lys His Ile Leu Glu Asp Tyr Gly Lys Asp Asp
225                 230                 235                 240

Glu Gln Leu Pro Val Tyr Lys Met Pro His Leu Glu Gly Trp Thr Val
                245                 250                 255

Ala Gly Asp Leu Leu Phe Val Pro Ala Ile Gly Leu His Glu Val Leu
            260                 265                 270

Val Ile Asp Lys His Asp Trp Glu Leu Val Lys Arg Ile Pro Val Val
        275                 280                 285

Gly Gln Pro Val Phe Val Met Ser Arg Pro Asp Gly Arg Gln Val Trp
    290                 295                 300

Val Asn Phe Ala Phe Pro Asp Asn Gln Thr Val Gln Val Ile Asp Val
305                 310                 315                 320

Lys Asp Phe Asn Ile Val Lys Thr Leu Gln Pro Gly Lys Ala Val Leu
                325                 330                 335

His Met Glu Phe Ser Pro Arg Gly Glu Ala Val Trp Met ala Val Arg
            340                 345                 350

Asp Glu Asp Arg Val Met Val Tyr Asp Thr Asp Ser Phe Asn Glu Thr
        355                 360                 365

Ala Arg Leu Pro Ala Gln Lys Pro Ser Gly Ile Phe Phe Ser Asn Arg
    370                 375                 380

Ala Asn Gln Leu Gly Leu
385                 390
```

<210> SEQ ID NO 41
<211> LENGTH: 453
<212> TYPE: DNA
<213> ORGANISM: Methylomonas 16a
<220> FEATURE:
<223> OTHER INFORMATION: ORF2
<223> OTHER INFORMATION: nirD gene

<400> SEQUENCE: 41

```
atgctggcat ccttgcacaa gcatttgctg aacgattatc agcaggattt tccgctgagc     60

ccgacaccgt ttctggatat cgccgagcag cttggcgtca cggaaggcga agtgctggcg    120

gcgtttcagg tgttggccga gcagcaaatg atcagccgca tcggccccgt gatcgcgccg    180

aacgccatcg gcaatagcgc cttggtggcg atggcggtgc cggagcagga tttggcccgt    240

gtcgccgcct tggtgagcgc ctatccggaa gtcaatcata actatgagcg ggaaaaccgc    300

ttcaatttgt ggtttgtgct gatcgcctcc gatcatactc acttgcagcg ggtgattgcc    360

gatatcgaga ctcaaaccgg ttatcaagcc atgctgttgc cgatgctggc cgattatttc    420

atcaacctgg gttttgaact caatctgaac gac                                 453
```

<210> SEQ ID NO 42
<211> LENGTH: 151
<212> TYPE: PRT
<213> ORGANISM: Methylomonas 16a
<220> FEATURE:

-continued

<223> OTHER INFORMATION: NirD

<400> SEQUENCE: 42

```
Met Leu Ala Ser Leu His Lys His Leu Leu Asn Asp Tyr Gln Gln Asp
  1               5                  10                  15

Phe Pro Leu Ser Pro Thr Pro Phe Leu Asp Ile Ala Glu Gln Leu Gly
             20                  25                  30

Val Thr Glu Gly Glu Val Leu Ala Ala Phe Gln Val Leu Ala Glu Gln
         35                  40                  45

Gln Met Ile Ser Arg Ile Gly Pro Val Ile Ala Pro Asn Ala Ile Gly
     50                  55                  60

Asn Ser Ala Leu Val Ala Met ala Val Pro Glu Gln Asp Leu Ala Arg
 65                  70                  75                  80

Val Ala Ala Leu Val Ser Ala Tyr Pro Glu Val Asn His Asn Tyr Glu
                 85                  90                  95

Arg Glu Asn Arg Phe Asn Leu Trp Phe Val Leu Ile Ala Ser Asp His
            100                 105                 110

Thr His Leu Gln Arg Val Ile Ala Asp Ile Glu Thr Gln Thr Gly Tyr
        115                 120                 125

Gln Ala Met Leu Leu Pro Met Leu Ala Asp Tyr Phe Ile Asn Leu Gly
    130                 135                 140

Phe Glu Leu Asn Leu Asn Asp
145                 150
```

<210> SEQ ID NO 43
<211> LENGTH: 504
<212> TYPE: DNA
<213> ORGANISM: Methylomonas 16a
<220> FEATURE:
<223> OTHER INFORMATION: ORF3
<223> OTHER INFORMATION: nirL gene

<400> SEQUENCE: 43

```
atggatgcct tggattatcg cttgattgcc gccgtgcaag cgggcttacc gcttaccgcg     60

cggccctatg ccgccatcgc cgcgaaattg gacatggacg aacaggacgt catcgcccga    120

ctgggacgtc tgaaaacgga aggtttgatc aggcgctggg gcgtcgtggt caagcaccgg    180

caactaggtt atcgcgccaa tgcgatgatc gtgatggata ttcctgatga tcaagttgcg    240

gaaatgggcc ggcgtgtcag ccagcacagc ttcgtcaatc tgtgttatcg ccgaccacgt    300

caaggcgagg tttggccgta taacctttat tgcatgatac acggcaaaaa tcgcgagacg    360

gttttgcagc aatgggccga tctgcaacaa agttgcggcc tggaagcctg tcggcacgag    420

attttattca gtcgtcgttg tttcaagcag cgtggggcta tttataaagc gcccgtgatt    480

gagccattgg agtttagtca tgga                                           504
```

<210> SEQ ID NO 44
<211> LENGTH: 168
<212> TYPE: PRT
<213> ORGANISM: Methylomonas 16a
<220> FEATURE:
<223> OTHER INFORMATION: NirL

<400> SEQUENCE: 44

```
Met Asp Ala Leu Asp Tyr Arg Leu Ile Ala Ala Val Gln Ala Gly Leu
  1               5                  10                  15

Pro Leu Thr Ala Arg Pro Tyr Ala Ala Ile Ala Ala Lys Leu Asp Met
             20                  25                  30
```

-continued

```
Asp Glu Gln Asp Val Ile Ala Arg Leu Gly Arg Leu Lys Thr Glu Gly
        35                  40                  45

Leu Ile Arg Arg Trp Gly Val Val Val Lys His Arg Gln Leu Gly Tyr
    50                  55                  60

Arg Ala Asn Ala Met Ile Val Met Asp Ile Pro Asp Asp Gln Val Ala
65                  70                  75                  80

Glu Met Gly Arg Arg Val Ser Gln His Ser Phe Val Asn Leu Cys Tyr
                85                  90                  95

Arg Arg Pro Arg Gln Gly Glu Val Trp Pro Tyr Asn Leu Tyr Cys Met
            100                 105                 110

Ile His Gly Lys Asn Arg Glu Thr Val Leu Gln Gln Trp Ala Asp Leu
        115                 120                 125

Gln Gln Ser Cys Gly Leu Glu Ala Cys Arg His Glu Ile Leu Phe Ser
    130                 135                 140

Arg Arg Cys Phe Lys Gln Arg Gly Ala Ile Tyr Lys Ala Pro Val Ile
145                 150                 155                 160

Glu Pro Leu Glu Phe Ser His Gly
                165


<210> SEQ ID NO 45
<211> LENGTH: 441
<212> TYPE: DNA
<213> ORGANISM: Methylomonas 16a
<220> FEATURE:
<223> OTHER INFORMATION: ORF4
<223> OTHER INFORMATION: nirG gene

<400> SEQUENCE: 45

atggatgaca tcgacaaagc catcatcaac cgtttgcaac agggcttgcc gatttgcgag      60

tcgccttata gatatgtcgc cgagcagctt ggtgtggccg aggcggaatt gctggagagg     120

ctgcaaacct tgttgaacca gggcgtttta tcgcgctttg ggccgatgta tcacgccgag     180

caaatgggcg gcgccttgac cttggcggcg atgaaggtgc caggggagcg tttcgacgaa     240

attgcaggca tcgtcaacgg ctttccggag gtggcgcata actatgcgcg taaccacgcc     300

ttgaacatgt ggtttgtgtt ggcgaccgaa aagccggaac aagtgcaggc ggtcatcgat     360

gccatcgaac ggcaaactgg cttgacggtc tataacatgc cgaaaatcaa ggaatattac     420

gtgggcttgc aactggaggc c                                               441


<210> SEQ ID NO 46
<211> LENGTH: 147
<212> TYPE: PRT
<213> ORGANISM: Methylomonas 16a
<220> FEATURE:
<223> OTHER INFORMATION: NirG

<400> SEQUENCE: 46

Met Asp Asp Ile Asp Lys Ala Ile Ile Asn Arg Leu Gln Gln Gly Leu
  1               5                  10                  15

Pro Ile Cys Glu Ser Pro Tyr Arg Tyr Val Ala Glu Gln Leu Gly Val
            20                  25                  30

Ala Glu Ala Glu Leu Leu Glu Arg Leu Gln Thr Leu Leu Asn Gln Gly
        35                  40                  45

Val Leu Ser Arg Phe Gly Pro Met Tyr His Ala Glu Gln Met Gly Gly
    50                  55                  60

Ala Leu Thr Leu Ala Ala Met Lys Val Pro Gly Glu Arg Phe Asp Glu
 65                  70                  75                  80
```

-continued

```
Ile Ala Gly Ile Val Asn Gly Phe Pro Glu Val Ala His Asn Tyr Ala
                 85                  90                  95

Arg Asn His Ala Leu Asn Met Trp Phe Val Leu Ala Thr Glu Lys Pro
            100                 105                 110

Glu Gln Val Gln Ala Val Ile Asp Ala Ile Glu Arg Gln Thr Gly Leu
        115                 120                 125

Thr Val Tyr Asn Met Pro Lys Ile Lys Glu Tyr Tyr Val Gly Leu Gln
    130                 135                 140

Leu Glu Ala
145


<210> SEQ ID NO 47
<211> LENGTH: 498
<212> TYPE: DNA
<213> ORGANISM: Methylomonas 16a
<220> FEATURE:
<223> OTHER INFORMATION: ORF5
<223> OTHER INFORMATION: nirH gene

<400> SEQUENCE: 47

atggactccg agccagtcaa aataatgatc gacactatcg accgtcaaat catccaggcc      60

acccaggccg gcttgccgct ggtcgcggaa ccttatcagg ccgtcgccga gcaattgggc     120

atcacggctc aagaattgat gctgcgcatg gccgatatgc tggaagctgg catcattcgg     180

cggattgcgg cggtgccgaa tcattacaaa ctgggttatc gtcataacgg catgacggtc     240

tgggatgtcg atgaccggca tgtcgacagc ctggggcagc gcgtcgccga attgccgttc     300

gtcagtcatt gctaccaacg gcctcgccat ttgccggatt ggccgtataa cctgttcgcg     360

atggtgcatg gcaagacgga acaagacgcc gaaaaacaaa ttgccgtgat cgccgaattg     420

ttgggcgagg attgctaccg gcacgcggtg ctgtacagca ccaagatttt gaagaaaacc     480

ggcttgagga ttgcgggg                                                    498


<210> SEQ ID NO 48
<211> LENGTH: 166
<212> TYPE: PRT
<213> ORGANISM: Methylomonas 16a
<220> FEATURE:
<223> OTHER INFORMATION: NirH

<400> SEQUENCE: 48

Met Asp Ser Glu Pro Val Lys Ile Met Ile Asp Thr Ile Asp Arg Gln
  1               5                  10                  15

Ile Ile Gln Ala Thr Gln Ala Gly Leu Pro Leu Val Ala Glu Pro Tyr
             20                  25                  30

Gln Ala Val Ala Glu Gln Leu Gly Ile Thr Ala Gln Glu Leu Met Leu
         35                  40                  45

Arg Met ala Asp Met Leu Glu Ala Gly Ile Ile Arg Arg Ile Ala Ala
     50                  55                  60

Val Pro Asn His Tyr Lys Leu Gly Tyr Arg His Asn Gly Met Thr Val
 65                  70                  75                  80

Trp Asp Val Asp Asp Arg His Val Asp Ser Leu Gly Gln Arg Val Ala
                 85                  90                  95

Glu Leu Pro Phe Val Ser His Cys Tyr Gln Arg Pro Arg His Leu Pro
            100                 105                 110

Asp Trp Pro Tyr Asn Leu Phe Ala Met Val His Gly Lys Thr Glu Gln
        115                 120                 125

Asp Ala Glu Lys Gln Ile Ala Val Ile Ala Glu Leu Leu Gly Glu Asp
```

```
    130                 135                 140

Cys Tyr Arg His Ala Val Leu Tyr Ser Thr Lys Ile Leu Lys Lys Thr
145                 150                 155                 160

Gly Leu Arg Ile Ala Gly
                165
```

<210> SEQ ID NO 49
<211> LENGTH: 1137
<212> TYPE: DNA
<213> ORGANISM: Methylomonas 16a
<220> FEATURE:
<223> OTHER INFORMATION: ORF6
<223> OTHER INFORMATION: nirJ gene

<400> SEQUENCE: 49

```
atgtttcgtc tgagtcaata catgcgcgag ctcgtgcatt caacgccgtt gggcaagccg      60

cgcaaaccgt ccggcccggt ggtaatctgg aatctgatcc gtcgctgcaa cctgacttgc     120

aagcattgct ataccacgtc cgccgacatc gattttccgg gtgaactgac gacgccggaa     180

atttatgcgg tgatggacga tttgaaagcc ttcaaggtgc cggtattgat tctgtccggc     240

ggagagccgt tgctgcatcc ggatattttt ccgatttcgc aacgcgccag cgacatgggc     300

ttttacgtgg ccttgtccag caacggcacg ctgatcgaca aaaacaatat cgagcaaatc     360

gccgcgatcg attatcaata tattggcgtc agtctggacg gcatgcgcga ggcgcacgac     420

aagttccgcc agaagcaagg ctctttcgac gcctcgctgg ccggcatccg tttatgccgc     480

gagcatggca tcaaggccgg cgtgcgcttc acgttgacgc gggacaacgc tcacgatttc     540

gatgccttgc tgcagttgat ggacgaggag gacatcgaca aattctatct gtcgcatctg     600

aattacggcg gccgcggcaa taaaaaccgg aaagacgatg ccgagtttca gttgacccgc     660

aaggtcatgg acgccttgtt cgaaaaggcg ctgagctggg aacagcaagg cctacaccgc     720

gaagtggtca ccggcaacaa cgatgccgat gccgtatatt tcctgcattg ggtcaaacgc     780

cgctttcccg agcgcgccga gcatatccag gccaagttgc agcaatgggg cggcaatgct     840

tccggcgtca acgtagccaa tatcgataat ctgggtaacg tgcatcccga taccttttgg     900

tggcattaca acttgggcag tgtccgccag cggccgtttt ccgagatatg gcaggatgtg     960

tccgacccat tgatggccgg gctgaaggcc tcgccgcgcc cgctgaaagg ccgctgcggc    1020

acctgtcatt atcaaagcat ttgcaacggc aatacccgcg tccgcgccca acaactgacc    1080

ggcgattttt gggctgaaga tccaggctgc tacctggatg acgaggaagt tttcagc       1137
```

<210> SEQ ID NO 50
<211> LENGTH: 379
<212> TYPE: PRT
<213> ORGANISM: Methylomonas 16a
<220> FEATURE:
<223> OTHER INFORMATION: Nir J

<400> SEQUENCE: 50

```
Met Phe Arg Leu Ser Gln Tyr Met Arg Glu Leu Val His Ser Thr Pro
  1               5                  10                  15

Leu Gly Lys Pro Arg Lys Pro Ser Gly Pro Val Val Ile Trp Asn Leu
             20                  25                  30

Ile Arg Arg Cys Asn Leu Thr Cys Lys His Cys Tyr Thr Thr Ser Ala
         35                  40                  45

Asp Ile Asp Phe Pro Gly Glu Leu Thr Thr Pro Glu Ile Tyr Ala Val
     50                  55                  60
```

-continued

```
Met Asp Asp Leu Lys Ala Phe Lys Val Pro Val Leu Ile Leu Ser Gly
 65                  70                  75                  80

Gly Glu Pro Leu Leu His Pro Asp Ile Phe Pro Ile Ser Gln Arg Ala
                 85                  90                  95

Ser Asp Met Gly Phe Tyr Val Ala Leu Ser Ser Asn Gly Thr Leu Ile
            100                 105                 110

Asp Lys Asn Asn Ile Glu Gln Ile Ala Ala Ile Asp Tyr Gln Tyr Ile
        115                 120                 125

Gly Val Ser Leu Asp Gly Met Arg Glu Ala His Asp Lys Phe Arg Gln
    130                 135                 140

Lys Gln Gly Ser Phe Asp Ala Ser Leu Ala Gly Ile Arg Leu Cys Arg
145                 150                 155                 160

Glu His Gly Ile Lys Ala Gly Val Arg Phe Thr Leu Thr Arg Asp Asn
                165                 170                 175

Ala His Asp Phe Asp Ala Leu Leu Gln Leu Met Asp Glu Glu Asp Ile
            180                 185                 190

Asp Lys Phe Tyr Leu Ser His Leu Asn Tyr Gly Gly Arg Gly Asn Lys
        195                 200                 205

Asn Arg Lys Asp Asp Ala Glu Phe Gln Leu Thr Arg Lys Val Met Asp
    210                 215                 220

Ala Leu Phe Glu Lys Ala Leu Ser Trp Glu Gln Gln Gly Leu His Arg
225                 230                 235                 240

Glu Val Val Thr Gly Asn Asn Asp Ala Asp Ala Val Tyr Phe Leu His
                245                 250                 255

Trp Val Lys Arg Arg Phe Pro Glu Arg Ala Glu His Ile Gln Ala Lys
            260                 265                 270

Leu Gln Gln Trp Gly Gly Asn Ala Ser Gly Val Asn Val Ala Asn Ile
        275                 280                 285

Asp Asn Leu Gly Asn Val His Pro Asp Thr Phe Trp Trp His Tyr Asn
    290                 295                 300

Leu Gly Ser Val Arg Gln Arg Pro Phe Ser Glu Ile Trp Gln Asp Val
305                 310                 315                 320

Ser Asp Pro Leu Met ala Gly Leu Lys Ala Ser Pro Arg Pro Leu Lys
                325                 330                 335

Gly Arg Cys Gly Thr Cys His Tyr Gln Ser Ile Cys Asn Gly Asn Thr
            340                 345                 350

Arg Val Arg Ala Gln Gln Leu Thr Gly Asp Phe Trp Ala Glu Asp Pro
        355                 360                 365

Gly Cys Tyr Leu Asp Asp Glu Glu Val Phe Ser
    370                 375
```

<210> SEQ ID NO 51
<211> LENGTH: 2760
<212> TYPE: DNA
<213> ORGANISM: Methylomonas 16a
<220> FEATURE:
<223> OTHER INFORMATION: ORF7
<223> OTHER INFORMATION: nasA gene

<400> SEQUENCE: 51

```
atgtctaaaa ctgccatcaa gacgacttgc ccttattgcg gcgtcggctg cggtatcgaa     60

gccagggtgc tcgatgccga aaaccatgtc gtcaatattg ccggcgatcc acagcatcag    120

tccaatttcg gccgactgtg ctccaagggc gcggcgctgg gtgataccgt cggtctggaa    180

ggccgccttt tatacccgga aatcgatggc cggcgcgtgg attggcccac ggtgctggac    240
```

-continued

```
cggatcgcgg ctaaattcaa tgcgatcatt gccgagcacg gcccggacgc ggtggcgttt    300
tatgtgtccg gacagttgtt gaccgaggat tattatgtcg ccaacaaatt gatgaagggc    360
ttcatcgggt cggcgaatat cgataccaat tccaggctgt gcatgtcctc ggcggtagtc    420
ggttacaagc gtgcgttcgg cgccgatgcg gtgccctgta atttcgagga tctggaacgg    480
gcagacttga tcgtgctggt cggttccaac gcggcctggt gccatccgat tgcgtttcag    540
cgcatgcgtc aggccaagat agacaatccg gcgctgaaaa tcgtactaat agacccgcgt    600
caaaccagca gctgcgatat cgccgatcgg catctggcca tcaagcccgg catggacggc    660
ttgttgttca atggcttgct ggtttatctg gccgaaaccg gcgcgttgga tcaggattac    720
atcgaacgac actgtgaagg ttttgccgag gccttggcga cggctcgagc gagcgccgcc    780
gattttaccg ttctggccaa ccgttgcggc gtggcggcgc acgatctggc gcaactgttt    840
gcctggtttg ccggtttgga caaggtcgtg accgtttatt cgcaaggcat caaccagtcc    900
agttcaggct ctgataaatg caacgccatc atcaattgcc atctggccag cggcaaaatc    960
ggcaaaccgg gctgcggacc gttctcgttt accggccagc ccaacgcgat gggcgggcgc   1020
gaggtcggtg ggctggcgaa catgctggcc gcgcacatgg atttggaaaa tccagcgcat   1080
gtcgatagag tcgcgcggtt ttggcaaacc gacagcgtcg cccgcaaacc aggcctgaaa   1140
gcggtagaaa ttttcgacgc catcgccgac ggtcgcatca aggccttatg gatcatggcg   1200
accaaccccg tggtatcgat gccggatgcc gacaaggtaa tcgaagcact taagcaatgc   1260
gaatttttgc tggtatcgga ttgcatcgcc aacaccgaca ccgtggagct ggcgcatgtc   1320
aaactgccgg ccaccggctg gagcgagaag gacggcaccg tcaccaatct ggaacgtcgc   1380
atctcgcggc agcggccatt attccagcct tcgggcgagg cgaaaccgga ttggtggatc   1440
gtcagccagg ttgctaagcg catggggttt gccggcttcg attatcgaaa cagcgccgaa   1500
atcttcaagg aacacgcggc cttgtccggt tttgaaaatg atgcagcgca ggggggcagg   1560
gattttgata tttcaggcct ggcaacgctg gatcaggccc agtttgacgc cttagtgccg   1620
atacaatggc ctgtcacagg caagactcaa ggcggaacgg cgcgcctgtt cgaagacggt   1680
cgttttttta ccgacaccgg caaggccaga ttcattgcac tcgagccgcg ctcgccaatg   1740
cacgccccca caccggatta tccgctggtc ttgaataccg gccgcatccg cgatcaatgg   1800
cacacgatga cccgcaccgc gctgtccgcg aagctcaatc aacacaagcc ggaaccgttc   1860
gtggagattc atccgcagga tgcgttgcgt tgggggctca aagcaaacgc cctggcccgg   1920
atcgaaagcc gttggggcgg catgttggcg cgggtcgacg tcagcgaggc tcagcaaccc   1980
ggcagcgtgt tcgtgcccat gcactggacc gcccagctca gcagtcatgg ccgagtcggc   2040
gccgtggtca accctgtcgt ggaccctttg tccgggcaac cggaaagcaa gcaaaccccg   2100
gtgcgcatcg cggcttgggc accttgctgg caagcgatgg tattgacgaa aatgccattg   2160
gacatcgacg attgcgaata ccacgtcaaa ataaggggcc atggcttttg gcgctatcat   2220
ttggcggatc aatcccagcg gccagacttg ccggcgtggg gccgcggcat tgtcggcagg   2280
ggggcggcca aacccaatga ttgcgtggaa tatctcgacc tggccgctgg cgattaccgc   2340
tttgccgaga tgcgggatca aaccccttcat gcctgcatgt tcattactca taatggggag   2400
ttgccggacc ctggctggct ggccagccta ttcggcaaac cgagattgac ccgcaaggaa   2460
cgcttcaacc tgctcagcgg cgtgccgccg caaggggaaa tcgatagcgg caaaacgatc   2520
tgctcctgct tcaacgtcgg cgaaaaaacc atcgtgcaag ccattcaaac ccgacatttg   2580
agctgtgtaa cagatatagg caactgcctg catgcgggaa cgggttgtgg ttcgtgttta   2640
```

-continued

```
ccggaattaa aaagcatttt ggcccacgcc aaaacgatcg atcctgcctc gctgcccatt   2700

cagccaactc aaatcccgcc ggcatcggag gggaaggagg aagccttttt ttcaggtcaa   2760


<210> SEQ ID NO 52
<211> LENGTH: 920
<212> TYPE: PRT
<213> ORGANISM: Methylomonas 16a
<220> FEATURE:
<223> OTHER INFORMATION: NasA

<400> SEQUENCE: 52

Met Ser Lys Thr Ala Ile Lys Thr Thr Cys Pro Tyr Cys Gly Val Gly
  1               5                  10                  15

Cys Gly Ile Glu Ala Arg Val Leu Asp Ala Glu Asn His Val Val Asn
             20                  25                  30

Ile Ala Gly Asp Pro Gln His Gln Ser Asn Phe Gly Arg Leu Cys Ser
         35                  40                  45

Lys Gly Ala Ala Leu Gly Asp Thr Val Gly Leu Glu Gly Arg Leu Leu
     50                  55                  60

Tyr Pro Glu Ile Asp Gly Arg Arg Val Asp Trp Pro Thr Val Leu Asp
 65                  70                  75                  80

Arg Ile Ala Ala Lys Phe Asn Ala Ile Ile Ala Glu His Gly Pro Asp
                 85                  90                  95

Ala Val Ala Phe Tyr Val Ser Gly Gln Leu Leu Thr Glu Asp Tyr Tyr
            100                 105                 110

Val Ala Asn Lys Leu Met Lys Gly Phe Ile Gly Ser Ala Asn Ile Asp
        115                 120                 125

Thr Asn Ser Arg Leu Cys Met Ser Ser Ala Val Val Gly Tyr Lys Arg
    130                 135                 140

Ala Phe Gly Ala Asp Ala Val Pro Cys Asn Phe Glu Asp Leu Glu Arg
145                 150                 155                 160

Ala Asp Leu Ile Val Leu Val Gly Ser Asn Ala Ala Trp Cys His Pro
                165                 170                 175

Ile Ala Phe Gln Arg Met Arg Gln Ala Lys Ile Asp Asn Pro Ala Leu
            180                 185                 190

Lys Ile Val Leu Ile Asp Pro Arg Gln Thr Ser Ser Cys Asp Ile Ala
        195                 200                 205

Asp Arg His Leu Ala Ile Lys Pro Gly Met Asp Gly Leu Leu Phe Asn
    210                 215                 220

Gly Leu Leu Val Tyr Leu Ala Glu Thr Gly Ala Leu Asp Gln Asp Tyr
225                 230                 235                 240

Ile Glu Arg His Cys Glu Gly Phe Ala Glu Ala Leu Ala Thr Ala Arg
                245                 250                 255

Ala Ser Ala Ala Asp Phe Thr Val Leu Ala Asn Arg Cys Gly Val Ala
            260                 265                 270

Ala His Asp Leu Ala Gln Leu Phe Ala Trp Phe Ala Gly Leu Asp Lys
        275                 280                 285

Val Val Thr Val Tyr Ser Gln Gly Ile Asn Gln Ser Ser Ser Gly Ser
    290                 295                 300

Asp Lys Cys Asn Ala Ile Ile Asn Cys His Leu Ala Ser Gly Lys Ile
305                 310                 315                 320

Gly Lys Pro Gly Cys Gly Pro Phe Ser Phe Thr Gly Gln Pro Asn Ala
                325                 330                 335

Met Gly Gly Arg Glu Val Gly Gly Leu Ala Asn Met Leu Ala Ala His
```

-continued

```
            340                 345                 350

Met Asp Leu Glu Asn Pro Ala His Val Asp Arg Val Ala Arg Phe Trp
        355                 360                 365

Gln Thr Asp Ser Val Ala Arg Lys Pro Gly Leu Lys Ala Val Glu Ile
    370                 375                 380

Phe Asp Ala Ile Ala Asp Gly Arg Ile Lys Ala Leu Trp Ile Met ala
385                 390                 395                 400

Thr Asn Pro Val Val Ser Met Pro Asp Ala Asp Lys Val Ile Glu Ala
                405                 410                 415

Leu Lys Gln Cys Glu Phe Leu Leu Val Ser Asp Cys Ile Ala Asn Thr
            420                 425                 430

Asp Thr Val Glu Leu Ala His Val Lys Leu Pro Ala Thr Gly Trp Ser
        435                 440                 445

Glu Lys Asp Gly Thr Val Thr Asn Leu Glu Arg Arg Ile Ser Arg Gln
    450                 455                 460

Arg Pro Leu Phe Gln Pro Ser Gly Glu Ala Lys Pro Asp Trp Trp Ile
465                 470                 475                 480

Val Ser Gln Val Ala Lys Arg Met Gly Phe Ala Gly Phe Asp Tyr Arg
                485                 490                 495

Asn Ser Ala Glu Ile Phe Lys Glu His Ala Ala Leu Ser Gly Phe Glu
            500                 505                 510

Asn Asp Ala Ala Gln Gly Gly Arg Asp Phe Asp Ile Ser Gly Leu Ala
        515                 520                 525

Thr Leu Asp Gln Ala Gln Phe Asp Ala Leu Val Pro Ile Gln Trp Pro
    530                 535                 540

Val Thr Gly Lys Thr Gln Gly Gly Thr Ala Arg Leu Phe Glu Asp Gly
545                 550                 555                 560

Arg Phe Phe Thr Asp Thr Gly Lys Ala Arg Phe Ile Ala Leu Glu Pro
                565                 570                 575

Arg Ser Pro Met His Ala Pro Thr Pro Asp Tyr Pro Leu Val Leu Asn
            580                 585                 590

Thr Gly Arg Ile Arg Asp Gln Trp His Thr Met Thr Arg Thr Ala Leu
        595                 600                 605

Ser Ala Lys Leu Asn Gln His Lys Pro Glu Pro Phe Val Glu Ile His
    610                 615                 620

Pro Gln Asp Ala Leu Arg Trp Gly Leu Lys Ala Asn Ala Leu Ala Arg
625                 630                 635                 640

Ile Glu Ser Arg Trp Gly Gly Met Leu Ala Arg Val Asp Val Ser Glu
                645                 650                 655

Ala Gln Gln Pro Gly Ser Val Phe Val Pro Met His Trp Thr Ala Gln
            660                 665                 670

Leu Ser Ser His Gly Arg Val Gly Ala Val Val Asn Pro Val Val Asp
        675                 680                 685

Pro Leu Ser Gly Gln Pro Glu Ser Lys Gln Thr Pro Val Arg Ile Ala
    690                 695                 700

Ala Trp Ala Pro Cys Trp Gln Ala Met Val Leu Thr Lys Met Pro Leu
705                 710                 715                 720

Asp Ile Asp Asp Cys Glu Tyr His Val Lys Ile Arg Gly His Gly Phe
                725                 730                 735

Trp Arg Tyr His Leu Ala Asp Gln Ser Gln Arg Pro Asp Leu Pro Ala
            740                 745                 750

Trp Gly Arg Gly Ile Val Gly Arg Gly Ala Ala Lys Pro Asn Asp Cys
        755                 760                 765
```

-continued

```
Val Glu Tyr Leu Asp Leu Ala Ala Gly Asp Tyr Arg Phe Ala Glu Met
    770                 775                 780

Arg Asp Gln Thr Leu His Ala Cys Met Phe Ile Thr His Asn Gly Glu
785                 790                 795                 800

Leu Pro Asp Pro Gly Trp Leu Ala Ser Leu Phe Gly Lys Pro Arg Leu
                805                 810                 815

Thr Arg Lys Glu Arg Phe Asn Leu Leu Ser Gly Val Pro Pro Gln Gly
            820                 825                 830

Glu Ile Asp Ser Gly Lys Thr Ile Cys Ser Cys Phe Asn Val Gly Glu
        835                 840                 845

Lys Thr Ile Val Gln Ala Ile Gln Thr Arg His Leu Ser Cys Val Thr
    850                 855                 860

Asp Ile Gly Asn Cys Leu His Ala Gly Thr Gly Cys Gly Ser Cys Leu
865                 870                 875                 880

Pro Glu Leu Lys Ser Ile Leu Ala His Ala Lys Thr Ile Asp Pro Ala
                885                 890                 895

Ser Leu Pro Ile Gln Pro Thr Gln Ile Pro Pro Ala Ser Glu Gly Lys
            900                 905                 910

Glu Glu Ala Phe Phe Ser Gly Gln
        915                 920
```

```
<210> SEQ ID NO 53
<211> LENGTH: 642
<212> TYPE: DNA
<213> ORGANISM: Methylomonas 16a
<220> FEATURE:
<223> OTHER INFORMATION: ORF8
<223> OTHER INFORMATION: norC gene

<400> SEQUENCE: 53

atggcaacga aaccgaacat tcacatcaac ctggaggtcg tcatgactga gcaagtcccg     60

cgctgggcgt cggaaacatt ctggaaaaaa accgcgatct gggtcaccgg cggatcgttc    120

gtgttgctgg tgatcttgac cttcgactcg ctggcgaaga tttccgctgg cggccccagg    180

gtgccggcct tcgacgtcat caacaaagac gtcagttacc gtttcgacaa ggaaaaacaa    240

cgctaccaac cagtgatcgg cgacgacgcc cctctgtttg gcaaaaccct gagcgaggaa    300

gaagccgaaa aactggtcga cctgggcaag aaaaccgtgc aggccaagaa ctgcatgaac    360

tgccataccc tgctcggcaa tggcgcttat tatgcgcccg acttgaccaa ggcctggctg    420

gaccagggct ggatcgccaa ggagtcgcgc gagcaaatga tggtcaattt cctgctcgat    480

cccgagaaaa atgcccgcac cttcggctcc aaccgcaaga tgccgaatct cgacatcacg    540

caacaggagg ccgagggcat cgtcgccttt ttgaaatgga tggcatccat cgacaccaat    600

ggttttccgc ataatttcat cgcgctgggc gaagaggaca aa                       642


<210> SEQ ID NO 54
<211> LENGTH: 214
<212> TYPE: PRT
<213> ORGANISM: Methylomonas 16a
<220> FEATURE:
<223> OTHER INFORMATION: NorC

<400> SEQUENCE: 54

Met ala Thr Lys Pro Asn Ile His Ile Asn Leu Glu Val Val Met Thr
  1               5                  10                  15

Glu Gln Val Pro Arg Trp Ala Ser Glu Thr Phe Trp Lys Lys Thr Ala
             20                  25                  30
```

```
Ile Trp Val Thr Gly Gly Ser Phe Val Leu Leu Val Ile Leu Thr Phe
        35                  40                  45

Asp Ser Leu Ala Lys Ile Ser Ala Gly Gly Pro Arg Val Pro Ala Phe
    50                  55                  60

Asp Val Ile Asn Lys Asp Val Ser Tyr Arg Phe Asp Lys Glu Lys Gln
65                  70                  75                  80

Arg Tyr Gln Pro Val Ile Gly Asp Asp Ala Pro Leu Phe Gly Lys Thr
                85                  90                  95

Leu Ser Glu Glu Glu Ala Glu Lys Leu Val Asp Leu Gly Lys Lys Thr
            100                 105                 110

Val Gln Ala Lys Asn Cys Met Asn Cys His Thr Leu Leu Gly Asn Gly
        115                 120                 125

Ala Tyr Tyr Ala Pro Asp Leu Thr Lys Ala Trp Leu Asp Gln Gly Trp
    130                 135                 140

Ile Ala Lys Glu Ser Arg Glu Gln Met Met Val Asn Phe Leu Leu Asp
145                 150                 155                 160

Pro Glu Lys Asn Ala Arg Thr Phe Gly Ser Asn Arg Lys Met Pro Asn
                165                 170                 175

Leu Asp Ile Thr Gln Gln Glu Ala Glu Gly Ile Val Ala Phe Leu Lys
            180                 185                 190

Trp Met ala Ser Ile Asp Thr Asn Gly Phe Pro His Asn Phe Ile Ala
        195                 200                 205

Leu Gly Glu Glu Asp Lys
    210
```

<210> SEQ ID NO 55
<211> LENGTH: 1503
<212> TYPE: DNA
<213> ORGANISM: Methylomonas 16a
<220> FEATURE:
<223> OTHER INFORMATION: ORF9
<223> OTHER INFORMATION: norB gene

<400> SEQUENCE: 55

```
atgacgctac aagcctatca agaaaaagcc gctgtctgct gggccggttg caagcaacgc     60

cacgccgact tcatggccaa tccgcatttg accggcggcc aaaagctggc ggtgcattac    120

ttcaccgtcg ccatggtgct gttcatggcg caattgctgt tcggcctgct ggccggcctg    180

caattcatct tcccgagttt tttatacgaa atcctggatt tcaacgtcaa ccgcatggtg    240

cacatcaatg ccatggtggt gtggatgctg tacggctttt tgggctcggt gtactggttt    300

ctggaagacg agagcggcgt cgagatcgtc ggcttgaaat gggggcaact ggcgttttgg    360

gtgctgaccg gtgcggtcgc gctggtcgtg ctggtgtatt tgttcatcca gatcggcgcc    420

ggcaacgaca cttcgctgtg gctgatcaac gaaggccgcg aatacatcga agccccgcgc    480

tgggccgaca tcggcatcgt cgccgtggta ttgaccttct tttacaacgt cgccgccacc    540

ttcgccaaag gcaaatggtc cggcattgcc ggcgtgttga ccctggatct ggtggccctg    600

gccggcttgt atctggccgg catgttctac gtcaccaata tttcggtcga ccaatactgg    660

tggtggtggg tgatccatct atgggtcgaa gcgacctggg aagtgctggt tggctgcatc    720

atggcctgga gcctgatgaa gctgctgggc gtgcgccgcc aggtcgtaca aacttggttg    780

tacatcgaag ttgctttgat gttcggctcc ggcattcttg gcctgggtca tcactatttc    840

tggatcggca cgccggaata ctggttcagc atcggcggct tcttctcggc gctggaaccg    900

attccgctgg tagcaatggt cgtgcattcc atttacgatt ccggcgtgca caagtttaaa    960
```

```
aacagcaatc accccgccct ggcctggatc atcgcccata ctttcggcaa cttcctgggc   1020

gccggcgttt ggggattcat gcacacgctg ccgcaaatca acctgtacac ccacggcacg   1080

caatggtcgg cctcgcacgg ccacctggcc ttcttcggcg cctatgcgac catcaacatc   1140

gccttcttct acctggcggc gcagcaggcg cgcggcaacg tctggatggg cggtgacttg   1200

atcaacggct ggcgctggaa agcggcggcg attttgctaa atctgggcgt gttgggcatg   1260

accgtggcgc tattgatcgc cggttacgag caatcgttta tcgaacgcgc cgtcgaaggc   1320

tcgacctggg ccggttactt cgccgcgcaa aaccacccgt ggttcatgca agccatggtc   1380

tggcgcatgg tattcggctt gatgacggcc gtcggcggcg gcctgttgtt ctgggacttg   1440

ctggaaatcg gcaaaggcga acagcggccc gcggcggtga ttgccggtgg aacggttgcg   1500

gaa                                                                 1503
```

```
<210> SEQ ID NO 56
<211> LENGTH: 501
<212> TYPE: PRT
<213> ORGANISM: Methylomonas 16a
<220> FEATURE:
<223> OTHER INFORMATION: NorB

<400> SEQUENCE: 56

Met Thr Leu Gln Ala Tyr Gln Glu Lys Ala Ala Val Cys Trp Ala Gly
  1               5                  10                  15

Cys Lys Gln Arg His Ala Asp Phe Met ala Asn Pro His Leu Thr Gly
             20                  25                  30

Gly Gln Lys Leu Ala Val His Tyr Phe Thr Val Ala Met Val Leu Phe
         35                  40                  45

Met ala Gln Leu Leu Phe Gly Leu Leu Ala Gly Leu Gln Phe Ile Phe
     50                  55                  60

Pro Ser Phe Leu Tyr Glu Ile Leu Asp Phe Asn Val Asn Arg Met Val
 65                  70                  75                  80

His Ile Asn Ala Met Val Val Trp Met Leu Tyr Gly Phe Leu Gly Ser
                 85                  90                  95

Val Tyr Trp Phe Leu Glu Asp Glu Ser Gly Val Glu Ile Val Gly Leu
            100                 105                 110

Lys Trp Gly Gln Leu Ala Phe Trp Val Leu Thr Gly Ala Val Ala Leu
        115                 120                 125

Val Val Leu Val Tyr Leu Phe Ile Gln Ile Gly Ala Gly Asn Asp Thr
    130                 135                 140

Ser Leu Trp Leu Ile Asn Glu Gly Arg Glu Tyr Ile Glu Ala Pro Arg
145                 150                 155                 160

Trp Ala Asp Ile Gly Ile Val Ala Val Val Leu Thr Phe Phe Tyr Asn
                165                 170                 175

Val Ala Ala Thr Phe Ala Lys Gly Lys Trp Ser Gly Ile Ala Gly Val
            180                 185                 190

Leu Thr Leu Asp Leu Val Ala Leu Ala Gly Leu Tyr Leu Ala Gly Met
        195                 200                 205

Phe Tyr Val Thr Asn Ile Ser Val Asp Gln Tyr Trp Trp Trp Trp Val
    210                 215                 220

Ile His Leu Trp Val Glu Ala Thr Trp Glu Val Leu Val Gly Cys Ile
225                 230                 235                 240

Met ala Trp Ser Leu Met Lys Leu Leu Gly Val Arg Arg Gln Val Val
                245                 250                 255
```

-continued

```
Gln Thr Trp Leu Tyr Ile Glu Val Ala Leu Met Phe Gly Ser Gly Ile
            260                 265                 270

Leu Gly Leu Gly His His Tyr Phe Trp Ile Gly Thr Pro Glu Tyr Trp
        275                 280                 285

Phe Ser Ile Gly Gly Phe Phe Ser Ala Leu Glu Pro Ile Pro Leu Val
    290                 295                 300

Ala Met Val Val His Ser Ile Tyr Asp Ser Gly Val His Lys Phe Lys
305                 310                 315                 320

Asn Ser Asn His Pro Ala Leu Ala Trp Ile Ile Ala His Thr Phe Gly
                325                 330                 335

Asn Phe Leu Gly Ala Gly Val Trp Gly Phe Met His Thr Leu Pro Gln
            340                 345                 350

Ile Asn Leu Tyr Thr His Gly Thr Gln Trp Ser Ala Ser His Gly His
        355                 360                 365

Leu Ala Phe Phe Gly Ala Tyr Ala Thr Ile Asn Ile Ala Phe Phe Tyr
    370                 375                 380

Leu Ala Ala Gln Gln Ala Arg Gly Asn Val Trp Met Gly Gly Asp Leu
385                 390                 395                 400

Ile Asn Gly Trp Arg Trp Lys Ala Ala Ala Ile Leu Leu Asn Leu Gly
                405                 410                 415

Val Leu Gly Met Thr Val Ala Leu Leu Ile Ala Gly Tyr Glu Gln Ser
            420                 425                 430

Phe Ile Glu Arg Ala Val Glu Gly Ser Thr Trp Ala Gly Tyr Phe Ala
        435                 440                 445

Ala Gln Asn His Pro Trp Phe Met Gln Ala Met Val Trp Arg Met Val
    450                 455                 460

Phe Gly Leu Met Thr Ala Val Gly Gly Gly Leu Leu Phe Trp Asp Leu
465                 470                 475                 480

Leu Glu Ile Gly Lys Gly Glu Gln Arg Pro Ala Ala Val Ile Ala Gly
                485                 490                 495

Gly Thr Val Ala Glu
            500
```

<210> SEQ ID NO 57
<211> LENGTH: 2253
<212> TYPE: DNA
<213> ORGANISM: Methylomonas 16a
<220> FEATURE:
<223> OTHER INFORMATION: ORF10
<223> OTHER INFORMATION: norZ gene

<400> SEQUENCE: 57

```
atgacaaaaa ctcctgattt gtctccttgg tggctgcgca cggtgctgat cgtgatggtg      60

ctgggctttg caggcctgat cgtcatcaca tcgctggcct atcgtaatgc tccgccgatt     120

ccggcccaaa tcgttgatgc acaaggtgtt cgcctgtttt ccggtgacga aatcaaagaa     180

ggccaggcta tctttctcaa atacgggttg atgaacaacg gcagtatctg ggtcatggc      240

gcatacttgg ggccagatta ttcggccgag gcattgcacc gaatcggcga gaacaccgcc     300

actatcattg cccagcagca ataccaacag ccactttcct cactcacgcc cggccaattg     360

gccgccgtgt atgcacaaac cgcagtcgag ctaaagacca atcattatga tgccgccagc     420

gcaacgttgc gtctgaccgt gccggagaca tccgcctatc gtaagcagat cgcttattgg     480

acggattatt tcctgaatcc tgaacggaat ggcggactca aacgtggatt gatcagcgat     540

ccgactgaac tgcgccagtt taccgccttc atcacatgga ctgcctgggc ctcggtggcc     600
```

-continued

```
aaccgccccg gcgagaacta ctcctacacc aacaattttc catacgaccc cagcgtcggg    660
aatatgcccg ttcccggtgc gctgttatgg agtgcgttga gccttatcgt gctgctggcc    720
ggtattggaa tcgtacttct gatgtttgga aaattcgatt atcttggctg gattagcaca    780
ggacatcatg tacatcctca tctgttgcct gggcaagcca gtgccggtca actagcactg    840
gtgaaatttt tcgtggtggt ggcgctgctg tttcttgctc agaccttggt gggcggtgca    900
acggcgcact atcgcgccga tccaggcagt ttttacggcc ttgagctgga gaagctattt    960
cccagcaatc tgatgcgcac ctggcatcta caaaccgcgg ttttctggat tgccaccgct   1020
tttgtcgccg cagccttgtt tctcggtcgt tcactgcgca atgatgaacc tcgctggttc   1080
gcgggctggg ttcatctgct gttcggtgct ttcgccgtgg tcataggcgg tagcctgtta   1140
ggcgagtggg cggggatttc acaaatgctg gatcaatggt ggttctggct tggcaaccag   1200
ggttgggaat acctggagct cggccgtctg tggcagtacc tgcttatcgc cggtctgctg   1260
gcgtggttta cgcttttatt taagttgcta cagcctgata ccctgaacga ctcagaagcg   1320
aaacctttag tcaggctgtt cctgctagct tccttggcga ttccgctgtt ctacatcccg   1380
gcactcttct tcggcgcaaa gaccaacttc acagtggtcg atacctggcg cttctggatc   1440
attcatttat gggtcgaagg tttctttgaa ttctttgcca ccacgctggt ggcgctgctg   1500
ttttatcaac tgggtcttac ccagcgcaac gttgcgcttc gagtgattta cctcgacgcc   1560
atcctctatt tcgtcggcgg cctgattggt accggccatc actggtattt taccggccag   1620
agcagcgtca acatggcgct gtcggcaatg gtctcggtac tggaagtagt gcccttgacg   1680
ctgctgactc tggacgcctg ggatttcgtg cgcaccacac gcgctgactg cgacgtctgc   1740
ggcaaaccgg tagccatacc gcataaatgg acgttctatt tcttgatggc cgtcggcttc   1800
tggaatttcg tcggtgccgg catcttcggc tttctaatca acctgcctat cgtcagctat   1860
tatgaagtcg gaacccaact gacacccaac catggccatg ccgcgatgat gggggtattc   1920
ggcatgctgg cactggcact gatggtattc gtgttgcgcc agaccagctc cgatttgcgc   1980
tgggtcgaca tcgagaaata cgtaagggtc ggattttggg gctccaatgt tggcctggct   2040
ctgatgttaa tcatgagctt gttccccagt ggcgtgttgc aagtttggga tgtcgttcag   2100
catggatact ggcatgcgcg cagccttgat tacatcggca gcgaaaggtc gcgcctgatc   2160
gaatggctac gtctgcccgg tgatctggta tttatcctgt ttggcgccat accgttggca   2220
atcgcatcca tcaaaggctg gctggatgtg cat                                2253
```

<210> SEQ ID NO 58
<211> LENGTH: 751
<212> TYPE: PRT
<213> ORGANISM: Methylomonas 16a
<220> FEATURE:
<223> OTHER INFORMATION: NorZ

<400> SEQUENCE: 58

```
Met Thr Lys Thr Pro Asp Leu Ser Pro Trp Trp Leu Arg Thr Val Leu
  1               5                  10                  15

Ile Val Met Val Leu Gly Phe Ala Gly Leu Ile Val Ile Thr Ser Leu
             20                  25                  30

Ala Tyr Arg Asn Ala Pro Pro Ile Pro Ala Gln Ile Val Asp Ala Gln
         35                  40                  45

Gly Val Arg Leu Phe Ser Gly Asp Glu Ile Lys Glu Gly Gln Ala Ile
     50                  55                  60

Phe Leu Lys Tyr Gly Leu Met Asn Asn Gly Ser Ile Trp Gly His Gly
```

-continued

```
65                  70                  75                  80

Ala Tyr Leu Gly Pro Asp Tyr Ser Ala Glu Ala Leu His Arg Ile Gly
                85                  90                  95

Glu Asn Thr Ala Thr Ile Ile Ala Gln Gln Gln Tyr Gln Gln Pro Leu
            100                 105                 110

Ser Ser Leu Thr Pro Gly Gln Leu Ala Ala Val Tyr Ala Gln Thr Ala
        115                 120                 125

Val Glu Leu Lys Thr Asn His Tyr Asp Ala Ala Ser Ala Thr Leu Arg
    130                 135                 140

Leu Thr Val Pro Glu Thr Ser Ala Tyr Arg Lys Gln Ile Ala Tyr Trp
145                 150                 155                 160

Thr Asp Tyr Phe Leu Asn Pro Glu Arg Asn Gly Gly Leu Lys Arg Gly
                165                 170                 175

Leu Ile Ser Asp Pro Thr Glu Leu Arg Gln Phe Thr Ala Phe Ile Thr
            180                 185                 190

Trp Thr Ala Trp Ala Ser Val Ala Asn Arg Pro Gly Glu Asn Tyr Ser
        195                 200                 205

Tyr Thr Asn Asn Phe Pro Tyr Asp Pro Ser Val Gly Asn Met Pro Val
    210                 215                 220

Pro Gly Ala Leu Leu Trp Ser Ala Leu Ser Leu Ile Val Leu Leu Ala
225                 230                 235                 240

Gly Ile Gly Ile Val Leu Leu Met Phe Gly Lys Phe Asp Tyr Leu Gly
                245                 250                 255

Trp Ile Ser Thr Gly His His Val His Pro His Leu Leu Pro Gly Gln
            260                 265                 270

Ala Ser Ala Gly Gln Leu Ala Leu Val Lys Phe Phe Val Val Val Ala
        275                 280                 285

Leu Leu Phe Leu Ala Gln Thr Leu Val Gly Gly Ala Thr Ala His Tyr
    290                 295                 300

Arg Ala Asp Pro Gly Ser Phe Tyr Gly Leu Glu Leu Glu Lys Leu Phe
305                 310                 315                 320

Pro Ser Asn Leu Met Arg Thr Trp His Leu Gln Thr Ala Val Phe Trp
                325                 330                 335

Ile Ala Thr Ala Phe Val Ala Ala Ala Leu Phe Leu Gly Arg Ser Leu
            340                 345                 350

Arg Asn Asp Glu Pro Arg Trp Phe Ala Gly Trp Val His Leu Leu Phe
        355                 360                 365

Gly Ala Phe Ala Val Val Ile Gly Gly Ser Leu Leu Gly Glu Trp Ala
    370                 375                 380

Gly Ile Ser Gln Met Leu Asp Gln Trp Trp Phe Trp Leu Gly Asn Gln
385                 390                 395                 400

Gly Trp Glu Tyr Leu Glu Leu Gly Arg Leu Trp Gln Tyr Leu Leu Ile
                405                 410                 415

Ala Gly Leu Leu Ala Trp Phe Thr Leu Leu Phe Lys Leu Leu Gln Pro
            420                 425                 430

Asp Thr Leu Asn Asp Ser Glu Ala Lys Pro Leu Val Arg Leu Phe Leu
        435                 440                 445

Leu Ala Ser Leu Ala Ile Pro Leu Phe Tyr Ile Pro Ala Leu Phe Phe
    450                 455                 460

Gly Ala Lys Thr Asn Phe Thr Val Val Asp Thr Trp Arg Phe Trp Ile
465                 470                 475                 480

Ile His Leu Trp Val Glu Gly Phe Phe Glu Phe Phe Ala Thr Thr Leu
                485                 490                 495
```

-continued

```
Val Ala Leu Leu Phe Tyr Gln Leu Gly Leu Thr Gln Arg Asn Val Ala
            500                 505                 510

Leu Arg Val Ile Tyr Leu Asp Ala Ile Leu Tyr Phe Val Gly Gly Leu
        515                 520                 525

Ile Gly Thr Gly His His Trp Tyr Phe Thr Gly Gln Ser Ser Val Asn
    530                 535                 540

Met ala Leu Ser Ala Met Val Ser Val Leu Glu Val Val Pro Leu Thr
545                 550                 555                 560

Leu Leu Thr Leu Asp Ala Trp Asp Phe Val Arg Thr Thr Arg Ala Asp
                565                 570                 575

Cys Asp Val Cys Gly Lys Pro Val Ala Ile Pro His Lys Trp Thr Phe
            580                 585                 590

Tyr Phe Leu Met ala Val Gly Phe Trp Asn Phe Val Gly Ala Gly Ile
        595                 600                 605

Phe Gly Phe Leu Ile Asn Leu Pro Ile Val Ser Tyr Tyr Glu Val Gly
    610                 615                 620

Thr Gln Leu Thr Pro Asn His Gly His Ala Ala Met Met Gly Val Phe
625                 630                 635                 640

Gly Met Leu Ala Leu Ala Leu Met Val Phe Val Leu Arg Gln Thr Ser
                645                 650                 655

Ser Asp Leu Arg Trp Val Asp Ile Glu Lys Tyr Val Arg Val Gly Phe
            660                 665                 670

Trp Gly Ser Asn Val Gly Leu Ala Leu Met Leu Ile Met Ser Leu Phe
        675                 680                 685

Pro Ser Gly Val Leu Gln Val Trp Asp Val Val Gln His Gly Tyr Trp
    690                 695                 700

His Ala Arg Ser Leu Asp Tyr Ile Gly Ser Glu Arg Ser Arg Leu Ile
705                 710                 715                 720

Glu Trp Leu Arg Leu Pro Gly Asp Leu Val Phe Ile Leu Phe Gly Ala
                725                 730                 735

Ile Pro Leu Ala Ile Ala Ser Ile Lys Gly Trp Leu Asp Val His
            740                 745                 750
```

<210> SEQ ID NO 59
<211> LENGTH: 1581
<212> TYPE: DNA
<213> ORGANISM: Methylomonas 16a
<220> FEATURE:
<223> OTHER INFORMATION: ORF11
<223> OTHER INFORMATION: norS gene

<400> SEQUENCE: 59

```
atgatgaaaa caacaactaa aagacgactg aatcaatccc ttctggcgag tgctatcgcc      60

gcgttactgt cgtccggtgc ggtgctggcg aaatccgaca gcccacacga catctacatg     120

gataattgcg ccagctgcca cggcgcggat cacggtggct atctggcgcc agccttgaat     180

gccgatacct tgaaaggtcg tagccctacg gcgttgcgta ccatcgtcat ggccggcagc     240

ttcgatacgc tgatgcctcc cttctacggc aaactgagcg acgacgagat tcgcggcgtg     300

atcaagcatt tgcaggaaac cccgaaacag ccgaatccgg cctggaccat cgacgacatg     360

aagaagtcct tgaaggttta cgtcaaggat gagagcaccc tgcctggcaa gccgactttc     420

caaatcgata acatcgataa tctgatcggc gtggcggcac gcggcaaata cggccgtggc     480

gaaggctcca aagctatttt catcaacagc accaaccatc aaaaagtcgg cgaagtggct     540

accggcaccg ccgcgcatat catcgacttc aatcctgcca acccgcgctg ggcttacgta     600
```

-continued

```
aaaaccgaca ccgccgagat tttcaaggta gatttgtatt cgatgcaggc ggtccgcagc    660

atcaagacag gttacaacgg ccccggcatg gggtatccc gcgacggcaa atacatcatg    720

gccggctcct tcgtgccgca taacgccgta atcctggatg ccgaaaccct ggaaccgttg    780

aaaaccttcg aactggaagg catcgatccc gacggtaaac atgtttcttc cgactcgggc    840

atgatcatcg gtacccctta tgccgacgtg ttcgcgattg cgctggaaaa tgccggccag    900

gtctggatcg tcgattacaa caaagaaggc ttcccggtca ccaaaatcga gaaagtgggc    960

cgtcacttgc acgacgcctt cctgacgcat ggcggcaaga aactgatggt ggcgtcttat   1020

gacgacagca tcgtcgccgc gatcgatctg gaaaaacgcg aactgatcaa gcaattgcca   1080

gcgggttgtg tgccgcacgt cggtggcggc gcggcggtcg tggttgatgg tcgtaccttg   1140

ggcttcggta ccaactttgg cgattgcgac aagatggtcg tcagcgtttg ggatttggac   1200

aaaatggaag tcgtcaaaca agtaccggtt tcaggtggca ctgaatcgcc tgcggctcat   1260

gccaacgcac cttatgtcgc ggttgacatc atcagcaaag acagacgtgc acgcaccatt   1320

cagttgatcg acaagaaaac cctggaagtt gccaaaactc tggatgtcgg cggccacgcc   1380

tacttcccgg aatatagcgc cgacggcaaa ttcctctatg tcagtgccgg ctacaatggc   1440

gacgaagtcg tggtttacga ttccaatacc ttgcaaaaag tggcgaccgt gccgatggaa   1500

agtcctgctg gtatcttctc cagaggccgt gtcaaataca tgactcgcgg tctgtcacct   1560

gacgaaatgg agcaaggcaa a                                              1581
```

<210> SEQ ID NO 60
<211> LENGTH: 527
<212> TYPE: PRT
<213> ORGANISM: Methylomonas 16a
<220> FEATURE:
<223> OTHER INFORMATION: NorS

<400> SEQUENCE: 60

```
Met Met Lys Thr Thr Thr Lys Arg Arg Leu Asn Gln Ser Leu Leu Ala
  1               5                  10                  15

Ser Ala Ile Ala Ala Leu Leu Ser Ser Gly Ala Val Leu Ala Lys Ser
             20                  25                  30

Asp Ser Pro His Asp Ile Tyr Met Asp Asn Cys Ala Ser Cys His Gly
         35                  40                  45

Ala Asp His Gly Gly Tyr Leu Ala Pro Ala Leu Asn Ala Asp Thr Leu
     50                  55                  60

Lys Gly Arg Ser Pro Thr Ala Leu Arg Thr Ile Val Met ala Gly Ser
 65                  70                  75                  80

Phe Asp Thr Leu Met Pro Pro Phe Tyr Gly Lys Leu Ser Asp Asp Glu
                 85                  90                  95

Ile Arg Gly Val Ile Lys His Leu Gln Glu Thr Pro Lys Gln Pro Asn
            100                 105                 110

Pro Ala Trp Thr Ile Asp Asp Met Lys Lys Ser Leu Lys Val Tyr Val
        115                 120                 125

Lys Asp Glu Ser Thr Leu Pro Gly Lys Pro Thr Phe Gln Ile Asp Asn
    130                 135                 140

Ile Asp Asn Leu Ile Gly Val Ala Ala Arg Gly Lys Tyr Gly Arg Gly
145                 150                 155                 160

Glu Gly Ser Lys Ala Ile Phe Ile Asn Ser Thr Asn His Gln Lys Val
                165                 170                 175

Gly Glu Val Ala Thr Gly Thr Ala Ala His Ile Ile Asp Phe Asn Pro
```

-continued

```
            180                 185                 190

Ala Asn Pro Arg Trp Ala Tyr Val Lys Thr Asp Thr Ala Glu Ile Phe
        195                 200                 205

Lys Val Asp Leu Tyr Ser Met Gln Ala Val Arg Ser Ile Lys Thr Gly
    210                 215                 220

Tyr Asn Gly Pro Gly Met Gly Val Ser Arg Asp Gly Lys Tyr Ile Met
225                 230                 235                 240

Ala Gly Ser Phe Val Pro His Asn Ala Val Ile Leu Asp Ala Glu Thr
                245                 250                 255

Leu Glu Pro Leu Lys Thr Phe Glu Leu Glu Gly Ile Asp Pro Asp Gly
            260                 265                 270

Lys His Val Ser Ser Asp Ser Gly Met Ile Ile Gly Thr Pro Tyr Ala
        275                 280                 285

Asp Val Phe Ala Ile Ala Leu Glu Asn Ala Gly Gln Val Trp Ile Val
    290                 295                 300

Asp Tyr Asn Lys Glu Gly Phe Pro Val Thr Lys Ile Glu Lys Val Gly
305                 310                 315                 320

Arg His Leu His Asp Ala Phe Leu Thr His Gly Gly Lys Lys Leu Met
                325                 330                 335

Val Ala Ser Tyr Asp Asp Ser Ile Val Ala Ala Ile Asp Leu Glu Lys
            340                 345                 350

Arg Glu Leu Ile Lys Gln Leu Pro Ala Gly Cys Val Pro His Val Gly
        355                 360                 365

Gly Gly Ala Ala Val Val Val Asp Gly Arg Thr Leu Gly Phe Gly Thr
    370                 375                 380

Asn Phe Gly Asp Cys Asp Lys Met Val Val Ser Val Trp Asp Leu Asp
385                 390                 395                 400

Lys Met Glu Val Val Lys Gln Val Pro Val Ser Gly Gly Thr Glu Ser
                405                 410                 415

Pro Ala Ala His Ala Asn Ala Pro Tyr Val Ala Val Asp Ile Ile Ser
            420                 425                 430

Lys Asp Arg Arg Ala Arg Thr Ile Gln Leu Ile Asp Lys Lys Thr Leu
        435                 440                 445

Glu Val Ala Lys Thr Leu Asp Val Gly Gly His Ala Tyr Phe Pro Glu
    450                 455                 460

Tyr Ser Ala Asp Gly Lys Phe Leu Tyr Val Ser Ala Gly Tyr Asn Gly
465                 470                 475                 480

Asp Glu Val Val Val Tyr Asp Ser Asn Thr Leu Gln Lys Val Ala Thr
                485                 490                 495

Val Pro Met Glu Ser Pro Ala Gly Ile Phe Ser Arg Gly Arg Val Lys
            500                 505                 510

Tyr Met Thr Arg Gly Leu Ser Pro Asp Glu Met Glu Gln Gly Lys
        515                 520                 525
```

<210> SEQ ID NO 61
<211> LENGTH: 1860
<212> TYPE: DNA
<213> ORGANISM: Methylomonas 16a
<220> FEATURE:
<223> OTHER INFORMATION: DXS

<400> SEQUENCE: 61

```
atgaaactga ccaccgacta tcccttgctt aaaaacatcc acacgccggc ggacatacgc     60

gcgctgtcca aggaccagct ccagcaactg gctgacgagg tgcgcggcta tctgacccac    120
```

-continued

```
acggtcagca tttccggcgg ccattttgcg gccggcctcg gcaccgtgga actgaccgtg    180

gccttgcatt atgtgttcaa tacccccgtc gatcagttgg tctgggacgt gggccatcag    240

gcctatccgc acaagattct gaccggtcgc aaggagcgca tgccgaccat tcgcaccctg    300

ggcggggtgt cagcctttcc ggcgcgggac gagagcgaat acgatgcctt cggcgtcggc    360

cattccagca cctcgatcag cgcggcactg ggcatggcca ttgcgtcgca gctgcgcggc    420

gaagacaaga agatggtagc catcatcggc gacggttcca tcaccggcgg catggcctat    480

gaggcgatga atcatgccgg cgatgtgaat gccaacctgc tggtgatctt gaacgacaac    540

gatatgtcga tctcgccgcc ggtcggggcg atgaacaatt atctgaccaa ggtgttgtcg    600

agcaagtttt attcgtcggt gcgggaagag agcaagaaag ctctggccaa gatgccgtcg    660

gtgtgggaac tggcgcgcaa gaccgaggaa cacgtgaagg gcatgatcgt gcccggtacc    720

ttgttcgagg aattgggctt caattatttc ggcccgatcg acggccatga tgtcgagatg    780

ctggtgtcga ccctggaaaa tctgaaggat ttgaccgggc cggtattcct gcatgtggtg    840

accaagaagg gcaaaggcta tgcgccagcc gagaaagacc cgttggccta ccatggcgtg    900

ccggctttcg atccgaccaa ggatttcctg cccaaggcgg cgccgtcgcc gcatccgacc    960

tataccgagg tgttcggccg ctggctgtgc gacatggcgg ctcaagacga gcgcttgctg   1020

ggcatcacgc cggcgatgcg cgaaggctct ggtttggtgg aattctcaca gaaatttccg   1080

aatcgctatt tcgatgtcgc catcgccgag cagcatgcgg tgaccttggc cgccggccag   1140

gcctgccagg gcgccaagcc ggtggtggcg atttattcca ccttcctgca acgcggttac   1200

gatcagttga tccacgacgt ggccttgcag aacttagata tgctctttgc actggatcgt   1260

gccggcttgg tcggcccgga tggaccgacc catgctggcg cctttgatta cagctacatg   1320

cgctgtattc cgaacatgct gatcatggct ccagccgacg agaacgagtg caggcagatg   1380

ctgaccaccg gcttccaaca ccatggcccg gcttcggtgc gctatccgcg cggcaaaggg   1440

cccggggcgg caatcgatcc gaccctgacc gcgctggaga tcggcaaggc cgaagtcaga   1500

caccacggca gccgcatcgc cattctggcc tggggcagca tggtcacgcc tgccgtcgaa   1560

gccggcaagc agctgggcgc gacggtggtg aacatgcgtt tcgtcaagcc gttcgatcaa   1620

gccttggtgc tggaattggc caggacgcac gatgtgttcg tcaccgtcga ggaaaacgtc   1680

atcgccggcg gcgctggcag tgcgatcaac accttcctgc aggcgcagaa ggtgctgatg   1740

ccggtctgca acatcggcct gcccgaccgc ttcgtcgagc aaggtagtcg cgaggaattg   1800

ctcagcctgg tcggcctcga cagcaagggc atcctcgcca ccatcgaaca gttttgcgct   1860
```

<210> SEQ ID NO 62
<211> LENGTH: 620
<212> TYPE: PRT
<213> ORGANISM: Methylomonas 16a
<220> FEATURE:
<223> OTHER INFORMATION: Amino acid sequences encoded by DXS

<400> SEQUENCE: 62

```
Met Lys Leu Thr Thr Asp Tyr Pro Leu Leu Lys Asn Ile His Thr Pro
  1               5                  10                  15

Ala Asp Ile Arg Ala Leu Ser Lys Asp Gln Leu Gln Gln Leu Ala Asp
             20                  25                  30

Glu Val Arg Gly Tyr Leu Thr His Thr Val Ser Ile Ser Gly Gly His
         35                  40                  45

Phe Ala Ala Gly Leu Gly Thr Val Glu Leu Thr Val Ala Leu His Tyr
     50                  55                  60
```

-continued

```
Val Phe Asn Thr Pro Val Asp Gln Leu Val Trp Asp Val Gly His Gln
 65                  70                  75                  80

Ala Tyr Pro His Lys Ile Leu Thr Gly Arg Lys Glu Arg Met Pro Thr
                85                  90                  95

Ile Arg Thr Leu Gly Gly Val Ser Ala Phe Pro Ala Arg Asp Glu Ser
            100                 105                 110

Glu Tyr Asp Ala Phe Gly Val Gly His Ser Ser Thr Ser Ile Ser Ala
        115                 120                 125

Ala Leu Gly Met ala Ile Ala Ser Gln Leu Arg Gly Glu Asp Lys Lys
    130                 135                 140

Met Val Ala Ile Ile Gly Asp Gly Ser Ile Thr Gly Gly Met ala Tyr
145                 150                 155                 160

Glu Ala Met Asn His Ala Gly Asp Val Asn Ala Asn Leu Leu Val Ile
                165                 170                 175

Leu Asn Asp Asn Asp Met Ser Ile Ser Pro Pro Val Gly Ala Met Asn
            180                 185                 190

Asn Tyr Leu Thr Lys Val Leu Ser Ser Lys Phe Tyr Ser Ser Val Arg
        195                 200                 205

Glu Glu Ser Lys Lys Ala Leu Ala Lys Met Pro Ser Val Trp Glu Leu
    210                 215                 220

Ala Arg Lys Thr Glu Glu His Val Lys Gly Met Ile Val Pro Gly Thr
225                 230                 235                 240

Leu Phe Glu Glu Leu Gly Phe Asn Tyr Phe Gly Pro Ile Asp Gly His
                245                 250                 255

Asp Val Glu Met Leu Val Ser Thr Leu Glu Asn Leu Lys Asp Leu Thr
            260                 265                 270

Gly Pro Val Phe Leu His Val Val Thr Lys Lys Gly Lys Gly Tyr Ala
        275                 280                 285

Pro Ala Glu Lys Asp Pro Leu Ala Tyr His Gly Val Pro Ala Phe Asp
    290                 295                 300

Pro Thr Lys Asp Phe Leu Pro Lys Ala Ala Pro Ser Pro His Pro Thr
305                 310                 315                 320

Tyr Thr Glu Val Phe Gly Arg Trp Leu Cys Asp Met ala Ala Gln Asp
                325                 330                 335

Glu Arg Leu Leu Gly Ile Thr Pro Ala Met Arg Glu Gly Ser Gly Leu
            340                 345                 350

Val Glu Phe Ser Gln Lys Phe Pro Asn Arg Tyr Phe Asp Val Ala Ile
        355                 360                 365

Ala Glu Gln His Ala Val Thr Leu Ala Ala Gly Gln Ala Cys Gln Gly
    370                 375                 380

Ala Lys Pro Val Val Ala Ile Tyr Ser Thr Phe Leu Gln Arg Gly Tyr
385                 390                 395                 400

Asp Gln Leu Ile His Asp Val Ala Leu Gln Asn Leu Asp Met Leu Phe
                405                 410                 415

Ala Leu Asp Arg Ala Gly Leu Val Gly Pro Asp Gly Pro Thr His Ala
            420                 425                 430

Gly Ala Phe Asp Tyr Ser Tyr Met Arg Cys Ile Pro Asn Met Leu Ile
        435                 440                 445

Met ala Pro Ala Asp Glu Asn Glu Cys Arg Gln Met Leu Thr Thr Gly
    450                 455                 460

Phe Gln His His Gly Pro Ala Ser Val Arg Tyr Pro Arg Gly Lys Gly
465                 470                 475                 480
```

-continued

```
Pro Gly Ala Ala Ile Asp Pro Thr Leu Thr Ala Leu Glu Ile Gly Lys
                485                 490                 495

Ala Glu Val Arg His His Gly Ser Arg Ile Ala Ile Leu Ala Trp Gly
            500                 505                 510

Ser Met Val Thr Pro Ala Val Glu Ala Gly Lys Gln Leu Gly Ala Thr
        515                 520                 525

Val Val Asn Met Arg Phe Val Lys Pro Phe Asp Gln Ala Leu Val Leu
    530                 535                 540

Glu Leu Ala Arg Thr His Asp Val Phe Val Thr Val Glu Glu Asn Val
545                 550                 555                 560

Ile Ala Gly Gly Ala Gly Ser Ala Ile Asn Thr Phe Leu Gln Ala Gln
                565                 570                 575

Lys Val Leu Met Pro Val Cys Asn Ile Gly Leu Pro Asp Arg Phe Val
            580                 585                 590

Glu Gln Gly Ser Arg Glu Glu Leu Leu Ser Leu Val Gly Leu Asp Ser
        595                 600                 605

Lys Gly Ile Leu Ala Thr Ile Glu Gln Phe Cys Ala
    610                 615                 620
```

<210> SEQ ID NO 63
<211> LENGTH: 1182
<212> TYPE: DNA
<213> ORGANISM: Methylomonas 16a
<220> FEATURE:
<223> OTHER INFORMATION: DXR

<400> SEQUENCE: 63

```
atgaaaggta tttgcatatt gggcgctacc ggttcgatcg gtgtcagcac gctggatgtc     60

gttgccaggc atccggataa atatcaagtc gttgcgctga ccgccaacgg caatatcgac    120

gcattgtatg aacaatgcct ggcccaccat ccggagtatg cggtggtggt catggaaagc    180

aaggtagcag agttcaaaca gcgcattgcc gcttcgccgg tagcggatat caaggtcttg    240

tcgggtagcg aggccttgca acaggtggcc acgctggaaa acgtcgatac ggtgatggcg    300

gctatcgtcg gcgcggccgg attgttgccg accttggccg cggccaaggc cggcaaaacc    360

gtgctgttgg ccaacaagga agccttggtg atgtcgggac aaatcttcat gcaggccgtc    420

agcgattccg gcgctgtgtt gctgccgata gacagcgagc acaacgccat ctttcagtgc    480

atgccggcgg gttatacgcc aggccataca gccaaacagg cgcgccgcat tttattgacc    540

gcttccggtg gcccatttcg acggacgccg atagaaacgt tgtccagcgt cacgccggat    600

caggccgttg cccatcctaa atgggacatg ggcgcaaga tttcggtcga ttccgccacc    660

atgatgaaca aggtctcga actgatcgaa gcctgcttgt tgttcaacat ggagcccgac    720

cagattgaag tcgtcattca tccgcagagc atcattcatt cgatggtgga ctatgtcgat    780

ggttcggttt tggcgcagat gggtaatccc gacatgcgca cgccgatagc gcacgcgatg    840

gcctggccgg aacgctttga ctctggtgtg gcgccgctgg atattttcga agtagggcac    900

atggatttcg aaaaacccga cttgaaacgg tttccttgtc tgagattggc ttatgaagcc    960

atcaagtctg gtggaattat gccaacggta ttgaacgcag ccaatgaaat tgctgtcgaa   1020

gcgtttttaa atgaagaagt caaattcact gacatcgcgg tcatcatcga gcgcagcatg   1080

gcccagttta aaccggacga tgccggcagc ctcgaattgg ttttgcaggc cgatcaagat   1140

gcgcgcgagg tggctagaga catcatcaag accttggtag ct                      1182
```

<210> SEQ ID NO 64

-continued

```
<211> LENGTH: 394
<212> TYPE: PRT
<213> ORGANISM: Methylomonas 16a
<220> FEATURE:
<223> OTHER INFORMATION: Amino acid sequences encoded by DXR

<400> SEQUENCE: 64

Met Lys Gly Ile Cys Ile Leu Gly Ala Thr Gly Ser Ile Gly Val Ser
  1               5                  10                  15

Thr Leu Asp Val Val Ala Arg His Pro Asp Lys Tyr Gln Val Val Ala
             20                  25                  30

Leu Thr Ala Asn Gly Asn Ile Asp Ala Leu Tyr Glu Gln Cys Leu Ala
         35                  40                  45

His His Pro Glu Tyr Ala Val Val Val Met Glu Ser Lys Val Ala Glu
     50                  55                  60

Phe Lys Gln Arg Ile Ala Ala Ser Pro Val Ala Asp Ile Lys Val Leu
 65                  70                  75                  80

Ser Gly Ser Glu Ala Leu Gln Gln Val Ala Thr Leu Glu Asn Val Asp
                 85                  90                  95

Thr Val Met ala Ala Ile Val Gly Ala Ala Gly Leu Leu Pro Thr Leu
            100                 105                 110

Ala Ala Ala Lys Ala Gly Lys Thr Val Leu Leu Ala Asn Lys Glu Ala
        115                 120                 125

Leu Val Met Ser Gly Gln Ile Phe Met Gln Ala Val Ser Asp Ser Gly
    130                 135                 140

Ala Val Leu Leu Pro Ile Asp Ser Glu His Asn Ala Ile Phe Gln Cys
145                 150                 155                 160

Met Pro Ala Gly Tyr Thr Pro Gly His Thr Ala Lys Gln Ala Arg Arg
                165                 170                 175

Ile Leu Leu Thr Ala Ser Gly Gly Pro Phe Arg Arg Thr Pro Ile Glu
            180                 185                 190

Thr Leu Ser Ser Val Thr Pro Asp Gln Ala Val Ala His Pro Lys Trp
        195                 200                 205

Asp Met Gly Arg Lys Ile Ser Val Asp Ser Ala Thr Met Met Asn Lys
    210                 215                 220

Gly Leu Glu Leu Ile Glu Ala Cys Leu Leu Phe Asn Met Glu Pro Asp
225                 230                 235                 240

Gln Ile Glu Val Val Ile His Pro Gln Ser Ile Ile His Ser Met Val
                245                 250                 255

Asp Tyr Val Asp Gly Ser Val Leu Ala Gln Met Gly Asn Pro Asp Met
            260                 265                 270

Arg Thr Pro Ile Ala His Ala Met ala Trp Pro Glu Arg Phe Asp Ser
        275                 280                 285

Gly Val Ala Pro Leu Asp Ile Phe Glu Val Gly His Met Asp Phe Glu
    290                 295                 300

Lys Pro Asp Leu Lys Arg Phe Pro Cys Leu Arg Leu Ala Tyr Glu Ala
305                 310                 315                 320

Ile Lys Ser Gly Gly Ile Met Pro Thr Val Leu Asn Ala Ala Asn Glu
                325                 330                 335

Ile Ala Val Glu Ala Phe Leu Asn Glu Glu Val Lys Phe Thr Asp Ile
            340                 345                 350

Ala Val Ile Ile Glu Arg Ser Met ala Gln Phe Lys Pro Asp Asp Ala
        355                 360                 365

Gly Ser Leu Glu Leu Val Leu Gln Ala Asp Gln Asp Ala Arg Glu Val
    370                 375                 380
```

```
Ala Arg Asp Ile Ile Lys Thr Leu Val Ala
385                 390


<210> SEQ ID NO 65
<211> LENGTH: 471
<212> TYPE: DNA
<213> ORGANISM: Methylomonas 16a
<220> FEATURE:
<223> OTHER INFORMATION: ISPF

<400> SEQUENCE: 65

atgatacgcg taggcatggg ttacgacgtg caccgtttca acgacggcga ccacatcatt      60

ttgggcggcg tcaaaatccc ttatgaaaaa ggcctggaag cccattccga cggcgacgtg     120

gtgctgcacg cattggccga cgccatcttg ggagccgccg ctttgggcga catcggcaaa     180

catttcccgg acaccgaccc caatttcaag ggcgccgaca gcagggtgct actgcgccac     240

gtgtacggca tcgtcaagga aaaaggctat aaactggtca acgccgacgt gaccatcatc     300

gctcaggcgc cgaagatgct gccacacgtg cccggcatgc gcgccaacat tgccgccgat     360

ctggaaaccg atgtcgattt cattaatgta aaagccacga cgaccgagaa actgggcttt     420

gagggccgta aggaaggcat cgccgtgcag gctgtggtgt tgatagaacg c              471


<210> SEQ ID NO 66
<211> LENGTH: 157
<212> TYPE: PRT
<213> ORGANISM: Methylomonas 16a
<220> FEATURE:
<223> OTHER INFORMATION: Amino acid sequences encoded by ISPF

<400> SEQUENCE: 66

Met Ile Arg Val Gly Met Gly Tyr Asp Val His Arg Phe Asn Asp Gly
  1               5                  10                  15

Asp His Ile Ile Leu Gly Gly Val Lys Ile Pro Tyr Glu Lys Gly Leu
             20                  25                  30

Glu Ala His Ser Asp Gly Asp Val Val Leu His Ala Leu Ala Asp Ala
         35                  40                  45

Ile Leu Gly Ala Ala Ala Leu Gly Asp Ile Gly Lys His Phe Pro Asp
     50                  55                  60

Thr Asp Pro Asn Phe Lys Gly Ala Asp Ser Arg Val Leu Leu Arg His
 65                  70                  75                  80

Val Tyr Gly Ile Val Lys Glu Lys Gly Tyr Lys Leu Val Asn Ala Asp
                 85                  90                  95

Val Thr Ile Ile Ala Gln Ala Pro Lys Met Leu Pro His Val Pro Gly
            100                 105                 110

Met Arg Ala Asn Ile Ala Ala Asp Leu Glu Thr Asp Val Asp Phe Ile
        115                 120                 125

Asn Val Lys Ala Thr Thr Thr Glu Lys Leu Gly Phe Glu Gly Arg Lys
    130                 135                 140

Glu Gly Ile Ala Val Gln Ala Val Val Leu Ile Glu Arg
145                 150                 155


<210> SEQ ID NO 67
<211> LENGTH: 693
<212> TYPE: DNA
<213> ORGANISM: Methylomonas 16a
<220> FEATURE:
<223> OTHER INFORMATION: ISPD

<400> SEQUENCE: 67
```

```
atgaacccaa ccatccaatg ctgggccgtc gtgcccgcag ccggcgtcgg caaacgcatg     60

caagccgatc gccccaaaca atatttaccg cttgccggta aaacggtcat cgaacacaca    120

ctgactcgac tacttgagtc cgacgccttc caaaaagttg cggtggcgat ttccgtcgaa    180

gacccttatt ggcctgaact gtccatagcc aaacaccccg acatcatcac cgcgcctggc    240

ggcaaggaac gcgccgactc ggtgctgtct gcactgaagg ctttagaaga tatagccagc    300

gaaaatgatt gggtgctggt acacgacgcc gcccgcccct gcttgacggg cagcgacatc    360

caccttcaaa tcgatacctt aaaaaatgac ccggtcggcg gcatcctggc cttgagttcg    420

cacgacacat tgaaacacgt ggatggtgac acgatcaccg caaccataga cagaaagcac    480

gtctggcgcg ccttgacgcc gcaaatgttc aaatacggca tgttgcgcga cgcgttgcaa    540

cgaaccgaag gcaatccggc cgtcaccgac gaagccagtg cgctggaact tttgggccat    600

aaacccaaaa tcgtggaagg ccgcccggac aacatcaaaa tcacccgccc ggaagatttg    660

gccctggcac aattttatat ggagcaacaa gca                                 693


<210> SEQ ID NO 68
<211> LENGTH: 231
<212> TYPE: PRT
<213> ORGANISM: Methylomonas 16a
<220> FEATURE:
<223> OTHER INFORMATION: Amino acid sequences encoded by ISPD

<400> SEQUENCE: 68

Met Asn Pro Thr Ile Gln Cys Trp Ala Val Val Pro Ala Ala Gly Val
  1               5                  10                  15

Gly Lys Arg Met Gln Ala Asp Arg Pro Lys Gln Tyr Leu Pro Leu Ala
             20                  25                  30

Gly Lys Thr Val Ile Glu His Thr Leu Thr Arg Leu Leu Glu Ser Asp
         35                  40                  45

Ala Phe Gln Lys Val Ala Val Ala Ile Ser Val Glu Asp Pro Tyr Trp
     50                  55                  60

Pro Glu Leu Ser Ile Ala Lys His Pro Asp Ile Ile Thr Ala Pro Gly
 65                  70                  75                  80

Gly Lys Glu Arg Ala Asp Ser Val Leu Ser Ala Leu Lys Ala Leu Glu
                 85                  90                  95

Asp Ile Ala Ser Glu Asn Asp Trp Val Leu Val His Asp Ala Ala Arg
            100                 105                 110

Pro Cys Leu Thr Gly Ser Asp Ile His Leu Gln Ile Asp Thr Leu Lys
        115                 120                 125

Asn Asp Pro Val Gly Gly Ile Leu Ala Leu Ser Ser His Asp Thr Leu
    130                 135                 140

Lys His Val Asp Gly Asp Thr Ile Thr Ala Thr Ile Asp Arg Lys His
145                 150                 155                 160

Val Trp Arg Ala Leu Thr Pro Gln Met Phe Lys Tyr Gly Met Leu Arg
                165                 170                 175

Asp Ala Leu Gln Arg Thr Glu Gly Asn Pro Ala Val Thr Asp Glu Ala
            180                 185                 190

Ser Ala Leu Glu Leu Leu Gly His Lys Pro Lys Ile Val Glu Gly Arg
        195                 200                 205

Pro Asp Asn Ile Lys Ile Thr Arg Pro Glu Asp Leu Ala Leu Ala Gln
    210                 215                 220

Phe Tyr Met Glu Gln Gln Ala
225                 230
```

<210> SEQ ID NO 69
<211> LENGTH: 1632
<212> TYPE: DNA
<213> ORGANISM: Methylomonas 16a
<220> FEATURE:
<223> OTHER INFORMATION: PYRG

<400> SEQUENCE: 69

```
atgacaaaat tcatctttat caccggcggc gtggtgtcat ccttgggaaa agggatagcc     60

gcctcctccc tggcggcgat tctggaagac cgcggcctca aagtcactat cacaaaactc    120

gatccctaca tcaacgtcga ccccggcacc atgagcccgt ttcaacacgg cgaggtgttc    180

gtgaccgaag acggtgccga aaccgatttg gaccttggcc attacgaacg gtttttgaaa    240

accacgatga ccaagaaaaa caacttcacc accggtcagg tttacgagca ggtattacgc    300

aacgagcgca aaggtgatta tcttggcgcg accgtgcaag tcattccaca tatcaccgac    360

gaaatcaaac gccgggtgta tgaaagcgcc gaagggaaag atgtggcatt gatcgaagtc    420

ggcggcacgg tgggcgacat cgaatcgtta ccgtttctgg aaaccatacg ccagatgggc    480

gtggaactgg gtcgtgaccg cgccttgttc attcatttga cgctggtgcc ttacatcaaa    540

tcggccggcg aactgaaaac caagcccacc cagcattcgg tcaaagaact gcgcaccatc    600

gggattcagc cggacatttt gatctgtcgt tcagaacaac cgatcccggc cagtgaacgc    660

cgcaagatcg cgctatttac caatgtcgcc gaaaaggcgg tgatttccgc gatcgatgcc    720

gacaccattt accgcattcc gctattgctg cgcgaacaag gcctggacga cctggtggtc    780

gatcagttgc gcctggacgt accagcggcg gatttatcgg cctgggaaaa ggtcgtcgat    840

ggcctgactc atccgaccga cgaagtcagc attgcgatcg tcggtaaata tgtcgaccac    900

accgatgcct acaaatcgct gaatgaagcc ctgattcatg ccggcattca cacgcgccac    960

aaggtgcaaa tcagctacat cgactccgaa accatagaag ccgaaggcac cgccaaattg   1020

aaaaacgtcg atgcgatcct ggtgccgggt ggtttcggcg aacgcggcgt ggaaggcaag   1080

atttctaccg tgcgttttgc ccgcgagaac aaaatcccgt atttgggcat ttgcttgggc   1140

atgcaatcgg cggtaatcga attcgcccgc aacgtggttg gcctggaagg cgcgcacagc   1200

accgaattcc tgccgaaatc gccacaccct gtgatcggct tgatcaccga atggatggac   1260

gaagccggcg aactggtcac acgcgacgaa gattccgatc tgggcggcac gatgcgtctg   1320

ggcgcgcaaa aatgccgcct gaaggctgat tccttggctt ttcagttgta tcaaaaagac   1380

gtcatcaccg agcgtcaccg ccaccgctac gaattcaaca atcaatattt aaaacaactg   1440

gaagcggccg gcatgaaatt ttccggtaaa tcgctggacg gccgcctggt ggagatcatc   1500

gagctacccg aacacccctg gttcctggcc tgccagttcc atcccgaatt cacctcgacg   1560

ccgcgtaacg gccacgccct attttcgggc ttcgtcgaag cggccgccaa acacaaaaca   1620

caaggcacag ca                                                       1632
```

<210> SEQ ID NO 70
<211> LENGTH: 544
<212> TYPE: PRT
<213> ORGANISM: Methylomonas 16a
<220> FEATURE:
<223> OTHER INFORMATION: Amino acid sequences encoded by ORF6 - PYRG

<400> SEQUENCE: 70

```
Met Thr Lys Phe Ile Phe Ile Thr Gly Gly Val Val Ser Ser Leu Gly
  1               5                  10                  15
```

-continued

```
Lys Gly Ile Ala Ala Ser Ser Leu Ala Ala Ile Leu Glu Asp Arg Gly
            20                  25                  30

Leu Lys Val Thr Ile Thr Lys Leu Asp Pro Tyr Ile Asn Val Asp Pro
        35                  40                  45

Gly Thr Met Ser Pro Phe Gln His Gly Glu Val Phe Val Thr Glu Asp
    50                  55                  60

Gly Ala Glu Thr Asp Leu Asp Leu Gly His Tyr Glu Arg Phe Leu Lys
65                  70                  75                  80

Thr Thr Met Thr Lys Lys Asn Asn Phe Thr Thr Gly Gln Val Tyr Glu
                85                  90                  95

Gln Val Leu Arg Asn Glu Arg Lys Gly Asp Tyr Leu Gly Ala Thr Val
            100                 105                 110

Gln Val Ile Pro His Ile Thr Asp Glu Ile Lys Arg Arg Val Tyr Glu
        115                 120                 125

Ser Ala Glu Gly Lys Asp Val Ala Leu Ile Glu Val Gly Gly Thr Val
    130                 135                 140

Gly Asp Ile Glu Ser Leu Pro Phe Leu Glu Thr Ile Arg Gln Met Gly
145                 150                 155                 160

Val Glu Leu Gly Arg Asp Arg Ala Leu Phe Ile His Leu Thr Leu Val
                165                 170                 175

Pro Tyr Ile Lys Ser Ala Gly Glu Leu Lys Thr Lys Pro Thr Gln His
            180                 185                 190

Ser Val Lys Glu Leu Arg Thr Ile Gly Ile Gln Pro Asp Ile Leu Ile
        195                 200                 205

Cys Arg Ser Glu Gln Pro Ile Pro Ala Ser Glu Arg Arg Lys Ile Ala
    210                 215                 220

Leu Phe Thr Asn Val Ala Glu Lys Ala Val Ile Ser Ala Ile Asp Ala
225                 230                 235                 240

Asp Thr Ile Tyr Arg Ile Pro Leu Leu Leu Arg Glu Gln Gly Leu Asp
                245                 250                 255

Asp Leu Val Val Asp Gln Leu Arg Leu Asp Val Pro Ala Ala Asp Leu
            260                 265                 270

Ser Ala Trp Glu Lys Val Val Asp Gly Leu Thr His Pro Thr Asp Glu
        275                 280                 285

Val Ser Ile Ala Ile Val Gly Lys Tyr Val Asp His Thr Asp Ala Tyr
    290                 295                 300

Lys Ser Leu Asn Glu Ala Leu Ile His Ala Gly Ile His Thr Arg His
305                 310                 315                 320

Lys Val Gln Ile Ser Tyr Ile Asp Ser Glu Thr Ile Glu Ala Glu Gly
                325                 330                 335

Thr Ala Lys Leu Lys Asn Val Asp Ala Ile Leu Val Pro Gly Gly Phe
            340                 345                 350

Gly Glu Arg Gly Val Glu Gly Lys Ile Ser Thr Val Arg Phe Ala Arg
        355                 360                 365

Glu Asn Lys Ile Pro Tyr Leu Gly Ile Cys Leu Gly Met Gln Ser Ala
    370                 375                 380

Val Ile Glu Phe Ala Arg Asn Val Val Gly Leu Glu Gly Ala His Ser
385                 390                 395                 400

Thr Glu Phe Leu Pro Lys Ser Pro His Pro Val Ile Gly Leu Ile Thr
                405                 410                 415

Glu Trp Met Asp Glu Ala Gly Glu Leu Val Thr Arg Asp Glu Asp Ser
            420                 425                 430
```

-continued

```
Asp Leu Gly Gly Thr Met Arg Leu Gly Ala Gln Lys Cys Arg Leu Lys
        435                 440                 445

Ala Asp Ser Leu Ala Phe Gln Leu Tyr Gln Lys Asp Val Ile Thr Glu
    450                 455                 460

Arg His Arg His Arg Tyr Glu Phe Asn Asn Gln Tyr Leu Lys Gln Leu
465                 470                 475                 480

Glu Ala Ala Gly Met Lys Phe Ser Gly Lys Ser Leu Asp Gly Arg Leu
                485                 490                 495

Val Glu Ile Ile Glu Leu Pro Glu His Pro Trp Phe Leu Ala Cys Gln
            500                 505                 510

Phe His Pro Glu Phe Thr Ser Thr Pro Arg Asn Gly His Ala Leu Phe
        515                 520                 525

Ser Gly Phe Val Glu Ala Ala Ala Lys His Lys Thr Gln Gly Thr Ala
    530                 535                 540
```

<210> SEQ ID NO 71
<211> LENGTH: 891
<212> TYPE: DNA
<213> ORGANISM: Methylomonas 16a
<220> FEATURE:
<223> OTHER INFORMATION: ORF7 ISPa

<400> SEQUENCE: 71

```
atgagtaaat tgaaagccta cctgaccgtc tgccaagaac gcgtcgagcg cgcgctggac      60

gcccgtctgc ctgccgaaaa catactgcca caaaccttgc atcaggccat gcgctattcc     120

gtattgaacg gcggcaaacg cacccggccc ttgttgactt atgcgaccgg tcaggctttg     180

ggcttgccgg aaaacgtgct ggatgcgccg gcttgcgcgg tagaattcat ccatgtgtat     240

tcgctgattc acgacgatct gccggccatg gacaacgatg atctgcgccg cggcaaaccg     300

acctgtcaca aggcttacga cgaggccacc gccattttgg ccggcgacgc actgcaggcg     360

ctggcctttg aagttctggc caacgacccc ggcatcaccg tcgatgcccc ggctcgcctg     420

aaaatgatca cggctttgac ccgcgccagc ggctctcaag gcatggtggg cggtcaagcc     480

atcgatctcg gctccgtcgg ccgcaaattg acgctgccgg aactcgaaaa catgcatatc     540

cacaagactg gcgccctgat ccgcgccagc gtcaatctgg cggcattatc caaacccgat     600

ctggatactt gcgtcgccaa gaaactggat cactatgcca aatgcatagg cttgtcgttc     660

caggtcaaag acgacattct cgacatcgaa gccgacaccg cgacactcgg caagactcag     720

ggcaaggaca tcgataacga caaaccgacc taccctgcgc tattgggcat ggctggcgcc     780

aaacaaaaag cccaggaatt gcacgaacaa gcagtcgaaa gcttaacggg atttggcagc     840

gaagccgacc tgctgcgcga actatcgctt tacatcatcg agcgcacgca c              891
```

<210> SEQ ID NO 72
<211> LENGTH: 297
<212> TYPE: PRT
<213> ORGANISM: Methylomonas 16a
<220> FEATURE:
<223> OTHER INFORMATION: Amino acid sequences encoded by ORF7 - ISPa

<400> SEQUENCE: 72

```
Met Ser Lys Leu Lys Ala Tyr Leu Thr Val Cys Gln Glu Arg Val Glu
  1               5                  10                  15

Arg Ala Leu Asp Ala Arg Leu Pro Ala Glu Asn Ile Leu Pro Gln Thr
            20                  25                  30

Leu His Gln Ala Met Arg Tyr Ser Val Leu Asn Gly Gly Lys Arg Thr
        35                  40                  45
```

-continued

```
Arg Pro Leu Leu Thr Tyr Ala Thr Gly Gln Ala Leu Gly Leu Pro Glu
     50                  55                  60

Asn Val Leu Asp Ala Pro Ala Cys Ala Val Glu Phe Ile His Val Tyr
 65                  70                  75                  80

Ser Leu Ile His Asp Asp Leu Pro Ala Met Asp Asn Asp Asp Leu Arg
                 85                  90                  95

Arg Gly Lys Pro Thr Cys His Lys Ala Tyr Asp Glu Ala Thr Ala Ile
            100                 105                 110

Leu Ala Gly Asp Ala Leu Gln Ala Leu Ala Phe Glu Val Leu Ala Asn
        115                 120                 125

Asp Pro Gly Ile Thr Val Asp Ala Pro Ala Arg Leu Lys Met Ile Thr
    130                 135                 140

Ala Leu Thr Arg Ala Ser Gly Ser Gln Gly Met Val Gly Gly Gln Ala
145                 150                 155                 160

Ile Asp Leu Gly Ser Val Gly Arg Lys Leu Thr Leu Pro Glu Leu Glu
                165                 170                 175

Asn Met His Ile His Lys Thr Gly Ala Leu Ile Arg Ala Ser Val Asn
            180                 185                 190

Leu Ala Ala Leu Ser Lys Pro Asp Leu Asp Thr Cys Val Ala Lys Lys
        195                 200                 205

Leu Asp His Tyr Ala Lys Cys Ile Gly Leu Ser Phe Gln Val Lys Asp
    210                 215                 220

Asp Ile Leu Asp Ile Glu Ala Asp Thr Ala Thr Leu Gly Lys Thr Gln
225                 230                 235                 240

Gly Lys Asp Ile Asp Asn Asp Lys Pro Thr Tyr Pro Ala Leu Leu Gly
                245                 250                 255

Met ala Gly Ala Lys Gln Lys Ala Gln Glu Leu His Glu Gln Ala Val
            260                 265                 270

Glu Ser Leu Thr Gly Phe Gly Ser Glu Ala Asp Leu Leu Arg Glu Leu
        275                 280                 285

Ser Leu Tyr Ile Ile Glu Arg Thr His
    290                 295
```

<210> SEQ ID NO 73
<211> LENGTH: 855
<212> TYPE: DNA
<213> ORGANISM: Methylomonas 16a
<220> FEATURE:
<223> OTHER INFORMATION: ISPE

<400> SEQUENCE: 73

```
atggattatg cggctgggtg gggcgaaaga tggcctgctc cggcaaaatt gaacttaatg     60

ttgaggatta ccggtcgcag gccagatggc tatcatctgt tgcaaacggt gtttcaaatg    120

ctcgatctat gcgattggtt gacgtttcat ccggttgatg atggccgcgt gacgctgcga    180

aatccaatct ccggcgttcc agagcaggat gacttgactg ttcgggcggc taatttgttg    240

aagtctcata ccggctgtgt gcgcggagtt tgtatcgata tcgagaaaaa tctgcctatg    300

ggtggtggtt tgggtggtgg aagttccgat gctgctacaa ccttggtagt tctaaatcgg    360

ctttggggct tgggcttgtc gaagcgtgag ttgatggatt tgggcttgag gcttggtgcc    420

gatgtgcctg tgtttgtgtt tggttgttcg gcctggggcg aaggtgtgag cgaggatttg    480

caggcaataa cgttgccgga acaatggttt gtcatcatta aaccggattg ccatgtgaat    540

actggagaaa ttttttctgc agaaaatttg acaaggaata gtgcagtcgt tacaatgagc    600
```

-continued

```
gactttcttg caggggataa tcggaatgat tgttcggaag tggtttgcaa gttatatcga    660

ccggtgaaag atgcaatcga tgcgttgtta tgctatgcgg aagcgagatt gacggggacc    720

ggtgcatgtg tgttcgctca gttttgtaac aaggaagatg ctgagagtgc gttagaagga    780

ttgaaagatc ggtggctggt gttcttggct aaaggcttga atcagtctgc gctctacaag    840

aaattagaac aggga                                                      855
```

<210> SEQ ID NO 74
<211> LENGTH: 285
<212> TYPE: PRT
<213> ORGANISM: Methylomonas 16a
<220> FEATURE:
<223> OTHER INFORMATION: Amino acid sequences encoded by ISPE

<400> SEQUENCE: 74

```
Met Asp Tyr Ala Ala Gly Trp Gly Glu Arg Trp Pro Ala Pro Ala Lys
  1               5                  10                  15

Leu Asn Leu Met Leu Arg Ile Thr Gly Arg Arg Pro Asp Gly Tyr His
             20                  25                  30

Leu Leu Gln Thr Val Phe Gln Met Leu Asp Leu Cys Asp Trp Leu Thr
         35                  40                  45

Phe His Pro Val Asp Asp Gly Arg Val Thr Leu Arg Asn Pro Ile Ser
     50                  55                  60

Gly Val Pro Glu Gln Asp Asp Leu Thr Val Arg Ala Ala Asn Leu Leu
 65                  70                  75                  80

Lys Ser His Thr Gly Cys Val Arg Gly Val Cys Ile Asp Ile Glu Lys
                 85                  90                  95

Asn Leu Pro Met Gly Gly Gly Leu Gly Gly Gly Ser Ser Asp Ala Ala
            100                 105                 110

Thr Thr Leu Val Val Leu Asn Arg Leu Trp Gly Leu Gly Leu Ser Lys
        115                 120                 125

Arg Glu Leu Met Asp Leu Gly Leu Arg Leu Gly Ala Asp Val Pro Val
    130                 135                 140

Phe Val Phe Gly Cys Ser Ala Trp Gly Glu Gly Val Ser Glu Asp Leu
145                 150                 155                 160

Gln Ala Ile Thr Leu Pro Glu Gln Trp Phe Val Ile Ile Lys Pro Asp
                165                 170                 175

Cys His Val Asn Thr Gly Glu Ile Phe Ser Ala Glu Asn Leu Thr Arg
            180                 185                 190

Asn Ser Ala Val Val Thr Met Ser Asp Phe Leu Ala Gly Asp Asn Arg
        195                 200                 205

Asn Asp Cys Ser Glu Val Val Cys Lys Leu Tyr Arg Pro Val Lys Asp
    210                 215                 220

Ala Ile Asp Ala Leu Leu Cys Tyr Ala Glu Ala Arg Leu Thr Gly Thr
225                 230                 235                 240

Gly Ala Cys Val Phe Ala Gln Phe Cys Asn Lys Glu Asp Ala Glu Ser
                245                 250                 255

Ala Leu Glu Gly Leu Lys Asp Arg Trp Leu Val Phe Leu Ala Lys Gly
            260                 265                 270

Leu Asn Gln Ser Ala Leu Tyr Lys Lys Leu Glu Gln Gly
        275                 280                 285
```

<210> SEQ ID NO 75
<211> LENGTH: 1533
<212> TYPE: DNA
<213> ORGANISM: Methylomonas 16a -continued

<220> FEATURE:
<223> OTHER INFORMATION: CRTN1

<400> SEQUENCE: 75

```
atggccaaca ccaaacacat catcatcgtc ggcgcgggtc ccggcggact ttgcgccggc     60

atgttgctga gccagcgcgg cttcaaggta tcgattttcg acaaacatgc agaaatcggc    120

ggccgcaacc gcccgatcaa catgaacggc tttaccttcg ataccggtcc gacattcttg    180

ttgatgaaag gcgtgctgga cgaaatgttc gaactgtgcg agcgccgtag cgaggattat    240

ctggaattcc tgccgctaag cccgatgtac cgcctgctgt acgacgaccg cgacatcttc    300

gtctattccg accgcgagaa catgcgcgcc gaattgcaac gggtattcga cgaaggcacg    360

gacggctacg aacagttcat ggaacaggaa cgcaaacgct tcaacgcgct gtatccctgc    420

atcacccgcg attattccag cctgaaatcc tttttgtcgc tggacttgat caaggccctg    480

ccgtggctgg cttttccgaa aagcgtgttc aataatctcg gccagtattt caaccaggaa    540

aaaatgcgcc tggccttttg ctttcagtcc aagtatctgg gcatgtcgcc gtgggaatgc    600

ccggcactgt ttacgatgct gccctatctg gagcacgaat acggcattta tcacgtcaaa    660

ggcggcctga accgcatcgc ggcggcgatg gcgcaagtga tcgcggaaaa cggcggcgaa    720

attcacttga acagcgaaat cgagtcgctg atcatcgaaa acggcgctgc caagggcgtc    780

aaattacaac atggcgcgga gctgcgcggc gacgaagtca tcatcaacgc ggattttgcc    840

cacgcgatga cgcatctggt caaaccgggc gtcttgaaaa aatacacccc ggaaaacctg    900

aagcagcgcg agtattcctg ttcgaccttc atgctgtatc tgggtttgga caagatttac    960

gatctgccgc accataccat cgtgtttgcc aaggattaca ccaccaatat ccgcaacatt   1020

ttcgacaaca aaccctgac ggacgatttt tcgttttacg tgcaaaacgc cagcgccagc    1080

gacgacagcc tagcgccagc cggcaaatcg gcgctgtacg tgctggtgcc gatgcccaac   1140

aacgacagcg gcctggactg gcaggcgcat tgccaaaacg tgcgcgaaca ggtgttggac   1200

acgctgggcg cgcgactggg attgagcgac atcagagccc atatcgaatg cgaaaaaatc   1260

atcacgccgc aaacctggga aacggacgaa cacgtttaca agggcgccac tttcagtttg   1320

tcgcacaagt tcagccaaat gctgtactgg cggccgcaca accgtttcga ggaactggcc   1380

aattgctatc tggtcggcgg cggcacgcat cccggtagcg gtttgccgac catctacgaa   1440

tcggcgcgga tttcggccaa gctgatttcc cagaaacatc gggtgaggtt caaggacata   1500

gcacacagcg cctggctgaa aaaagccaaa gcc                                 1533
```

<210> SEQ ID NO 76
<211> LENGTH: 511
<212> TYPE: PRT
<213> ORGANISM: Methylomonas 16a
<220> FEATURE:
<223> OTHER INFORMATION: Amino acid sequences encoded by CRTN1

<400> SEQUENCE: 76

```
Met ala Asn Thr Lys His Ile Ile Ile Val Gly Ala Gly Pro Gly Gly
  1               5                  10                  15

Leu Cys Ala Gly Met Leu Leu Ser Gln Arg Gly Phe Lys Val Ser Ile
             20                  25                  30

Phe Asp Lys His Ala Glu Ile Gly Gly Arg Asn Arg Pro Ile Asn Met
         35                  40                  45

Asn Gly Phe Thr Phe Asp Thr Gly Pro Thr Phe Leu Leu Met Lys Gly
     50                  55                  60
```

-continued

```
Val Leu Asp Glu Met Phe Glu Leu Cys Glu Arg Arg Ser Glu Asp Tyr
 65                  70                  75                  80

Leu Glu Phe Leu Pro Leu Ser Pro Met Tyr Arg Leu Leu Tyr Asp Asp
                 85                  90                  95

Arg Asp Ile Phe Val Tyr Ser Asp Arg Glu Asn Met Arg Ala Glu Leu
            100                 105                 110

Gln Arg Val Phe Asp Glu Gly Thr Asp Gly Tyr Glu Gln Phe Met Glu
        115                 120                 125

Gln Glu Arg Lys Arg Phe Asn Ala Leu Tyr Pro Cys Ile Thr Arg Asp
    130                 135                 140

Tyr Ser Ser Leu Lys Ser Phe Leu Ser Leu Asp Leu Ile Lys Ala Leu
145                 150                 155                 160

Pro Trp Leu Ala Phe Pro Lys Ser Val Phe Asn Asn Leu Gly Gln Tyr
                165                 170                 175

Phe Asn Gln Glu Lys Met Arg Leu Ala Phe Cys Phe Gln Ser Lys Tyr
            180                 185                 190

Leu Gly Met Ser Pro Trp Glu Cys Pro Ala Leu Phe Thr Met Leu Pro
        195                 200                 205

Tyr Leu Glu His Glu Tyr Gly Ile Tyr His Val Lys Gly Gly Leu Asn
    210                 215                 220

Arg Ile Ala Ala Ala Met ala Gln Val Ile Ala Glu Asn Gly Gly Glu
225                 230                 235                 240

Ile His Leu Asn Ser Glu Ile Glu Ser Leu Ile Ile Glu Asn Gly Ala
                245                 250                 255

Ala Lys Gly Val Lys Leu Gln His Gly Ala Glu Leu Arg Gly Asp Glu
            260                 265                 270

Val Ile Ile Asn Ala Asp Phe Ala His Ala Met Thr His Leu Val Lys
        275                 280                 285

Pro Gly Val Leu Lys Lys Tyr Thr Pro Glu Asn Leu Lys Gln Arg Glu
    290                 295                 300

Tyr Ser Cys Ser Thr Phe Met Leu Tyr Leu Gly Leu Asp Lys Ile Tyr
305                 310                 315                 320

Asp Leu Pro His His Thr Ile Val Phe Ala Lys Asp Tyr Thr Thr Asn
                325                 330                 335

Ile Arg Asn Ile Phe Asp Asn Lys Thr Leu Thr Asp Asp Phe Ser Phe
            340                 345                 350

Tyr Val Gln Asn Ala Ser Ala Ser Asp Asp Ser Leu Ala Pro Ala Gly
        355                 360                 365

Lys Ser Ala Leu Tyr Val Leu Val Pro Met Pro Asn Asn Asp Ser Gly
    370                 375                 380

Leu Asp Trp Gln Ala His Cys Gln Asn Val Arg Glu Gln Val Leu Asp
385                 390                 395                 400

Thr Leu Gly Ala Arg Leu Gly Leu Ser Asp Ile Arg Ala His Ile Glu
                405                 410                 415

Cys Glu Lys Ile Ile Thr Pro Gln Thr Trp Glu Thr Asp Glu His Val
            420                 425                 430

Tyr Lys Gly Ala Thr Phe Ser Leu Ser His Lys Phe Ser Gln Met Leu
        435                 440                 445

Tyr Trp Arg Pro His Asn Arg Phe Glu Glu Leu Ala Asn Cys Tyr Leu
    450                 455                 460

Val Gly Gly Gly Thr His Pro Gly Ser Gly Leu Pro Thr Ile Tyr Glu
465                 470                 475                 480

Ser Ala Arg Ile Ser Ala Lys Leu Ile Ser Gln Lys His Arg Val Arg
```

-continued

```
                485                 490                 495

Phe Lys Asp Ile Ala His Ser Ala Trp Leu Lys Lys Ala Lys Ala
            500                 505                 510


<210> SEQ ID NO 77
<211> LENGTH: 1491
<212> TYPE: DNA
<213> ORGANISM: Methylomonas 16a
<220> FEATURE:
<223> OTHER INFORMATION: CRTN2

<400> SEQUENCE: 77

atgaactcaa atgacaacca acgcgtgatc gtgatcggcg ccggcctcgg cggcctgtcc      60

gccgctattt cgctggccac ggccggcttt tccgtgcaac tcatcgaaaa aaacgacaag     120

gtcggcggca agctcaacat catgaccaaa gacggcttta ccttcgatct ggggccgtcc     180

attttgacga tgccgcacat ctttgaggcc ttgttcacag ggccggcaa  aaacatggcc     240

gattacgtgc aaatccagaa agtcgaaccg cactggcgca atttcttcga ggacggtagc     300

gtgatcgact tgtgcgaaga cgccgaaacc cagcgccgcg agctggataa acttggcccc     360

ggcacttacg cgcaattcca gcgctttctg gactattcga aaaacctctg cacggaaacc     420

gaagccggtt acttcgccaa gggcctggac ggcttttggg atttactcaa gttttacggc     480

ccgctccgca gcctgctgag tttcgacgtc ttccgcagca tggaccaggg cgtgcgccgc     540

tttatttccg atcccaagtt ggtcgaaatc ctgaattact tcatcaaata cgtcggctcc     600

tcgccttacg atgcgcccgc cttgatgaac ctgctgcctt acattcaata tcattacggc     660

ctgtggtacg tgaaaggcgg catgtatggc atggcgcagg ccatggaaaa actggccgtg     720

gaattgggcg tcgagattcg tttagatgcc gaggtgtcgg aaatccaaaa acaggacggc     780

agagcctgcg ccgtaaagtt ggcgaacggc gacgtgctgc cggccgacat cgtggtgtcg     840

aacatggaag tgattccggc gatggaaaaa ctgctgcgca gcccggccag cgaactgaaa     900

aaaatgcagc gcttcgagcc tagctgttcc ggcctggtgc tgcacttggg cgtggacagg     960

ctgtatccgc aactggcgca ccacaatttc ttttattccg atcatccgcg cgaacatttc    1020

gatgcggtat tcaaaagcca tcgcctgtcg gacgatccga ccatttatct ggtcgcgccg    1080

tgcaagaccg accccgccca ggcgccggcc ggctgcgaga tcatcaaaat cctgccccat    1140

atcccgcacc tcgaccccga caaactgctg accgccgagg attattcagc cttgcgcgag    1200

cgggtgctgg tcaaactcga acgcatgggc ctgacggatt tacgccaaca catcgtgacc    1260

gaagaatact ggacgccgct ggatattcag gccaaatatt attcaaacca gggctcgatt    1320

tacggcgtgg tcgccgaccg cttcaaaaac ctgggtttca aggcacctca acgcagcagc    1380

gaattatcca atctgtattt cgtcggcggc agcgtcaatc ccggcggcgg catgccgatg    1440

gtgacgctgt ccgggcaatt ggtgagggac aagattgtgg cggatttgca a             1491


<210> SEQ ID NO 78
<211> LENGTH: 497
<212> TYPE: PRT
<213> ORGANISM: Methylomonas 16a
<220> FEATURE:
<223> OTHER INFORMATION: Amino acid sequences encoded by CRTN2

<400> SEQUENCE: 78

Met Asn Ser Asn Asp Asn Gln Arg Val Ile Val Ile Gly Ala Gly Leu
  1               5                  10                  15

Gly Gly Leu Ser Ala Ala Ile Ser Leu Ala Thr Ala Gly Phe Ser Val
```

-continued

```
            20                  25                  30

Gln Leu Ile Glu Lys Asn Asp Lys Val Gly Gly Lys Leu Asn Ile Met
        35                  40                  45

Thr Lys Asp Gly Phe Thr Phe Asp Leu Gly Pro Ser Ile Leu Thr Met
    50                  55                  60

Pro His Ile Phe Glu Ala Leu Phe Thr Gly Ala Gly Lys Asn Met ala
65                  70                  75                  80

Asp Tyr Val Gln Ile Gln Lys Val Glu Pro His Trp Arg Asn Phe Phe
                85                  90                  95

Glu Asp Gly Ser Val Ile Asp Leu Cys Glu Asp Ala Glu Thr Gln Arg
            100                 105                 110

Arg Glu Leu Asp Lys Leu Gly Pro Gly Thr Tyr Ala Gln Phe Gln Arg
        115                 120                 125

Phe Leu Asp Tyr Ser Lys Asn Leu Cys Thr Glu Thr Glu Ala Gly Tyr
    130                 135                 140

Phe Ala Lys Gly Leu Asp Gly Phe Trp Asp Leu Leu Lys Phe Tyr Gly
145                 150                 155                 160

Pro Leu Arg Ser Leu Leu Ser Phe Asp Val Phe Arg Ser Met Asp Gln
                165                 170                 175

Gly Val Arg Arg Phe Ile Ser Asp Pro Lys Leu Val Glu Ile Leu Asn
            180                 185                 190

Tyr Phe Ile Lys Tyr Val Gly Ser Ser Pro Tyr Asp Ala Pro Ala Leu
        195                 200                 205

Met Asn Leu Leu Pro Tyr Ile Gln Tyr His Tyr Gly Leu Trp Tyr Val
    210                 215                 220

Lys Gly Gly Met Tyr Gly Met ala Gln Ala Met Glu Lys Leu Ala Val
225                 230                 235                 240

Glu Leu Gly Val Glu Ile Arg Leu Asp Ala Glu Val Ser Glu Ile Gln
                245                 250                 255

Lys Gln Asp Gly Arg Ala Cys Ala Val Lys Leu Ala Asn Gly Asp Val
            260                 265                 270

Leu Pro Ala Asp Ile Val Val Ser Asn Met Glu Val Ile Pro Ala Met
        275                 280                 285

Glu Lys Leu Leu Arg Ser Pro Ala Ser Glu Leu Lys Lys Met Gln Arg
    290                 295                 300

Phe Glu Pro Ser Cys Ser Gly Leu Val Leu His Leu Gly Val Asp Arg
305                 310                 315                 320

Leu Tyr Pro Gln Leu Ala His His Asn Phe Phe Tyr Ser Asp His Pro
                325                 330                 335

Arg Glu His Phe Asp Ala Val Phe Lys Ser His Arg Leu Ser Asp Asp
            340                 345                 350

Pro Thr Ile Tyr Leu Val Ala Pro Cys Lys Thr Asp Pro Ala Gln Ala
        355                 360                 365

Pro Ala Gly Cys Glu Ile Ile Lys Ile Leu Pro His Ile Pro His Leu
    370                 375                 380

Asp Pro Asp Lys Leu Leu Thr Ala Glu Asp Tyr Ser Ala Leu Arg Glu
385                 390                 395                 400

Arg Val Leu Val Lys Leu Glu Arg Met Gly Leu Thr Asp Leu Arg Gln
                405                 410                 415

His Ile Val Thr Glu Glu Tyr Trp Thr Pro Leu Asp Ile Gln Ala Lys
            420                 425                 430

Tyr Tyr Ser Asn Gln Gly Ser Ile Tyr Gly Val Val Ala Asp Arg Phe
        435                 440                 445
```

-continued

```
Lys Asn Leu Gly Phe Lys Ala Pro Gln Arg Ser Ser Glu Leu Ser Asn
    450                 455                 460

Leu Tyr Phe Val Gly Gly Ser Val Asn Pro Gly Gly Gly Met Pro Met
465                 470                 475                 480

Val Thr Leu Ser Gly Gln Leu Val Arg Asp Lys Ile Val Ala Asp Leu
                485                 490                 495

Gln
497
```

<210> SEQ ID NO 79
<211> LENGTH: 1455
<212> TYPE: DNA
<213> ORGANISM: METHYLOMONAS SP.

<400> SEQUENCE: 79

```
agacgttgct cctgtatcag cgttcttctc cggcttcgtt tctatcatca tttacttctt     60

gtggcacttc ttcggccgtt ggttctcaaa aaccgacttc atcgccgacg atgcttctta    120

attgaagatt tgagaaaaat gacggctggc atgacttgca gtagattgcc agaagatctt    180

aattacaaat tctctagtaa tagaggagga aatatgaaaa taattaaaga cagagttgca    240

aaactgtcct ttgtcgcact gctgatcact atgacagcag cgatgttcta cgctccaaca    300

gcatctgctc acggtgaaaa gtctcaagcg gctttcatgc gtatgcgtac cattcactgg    360

tttgacttga actggtcagc cgatgaagtt gctgtaaacg ataccatgac aatttccggt    420

aaattccacg ttttcgctgg atggcctgaa actgttgata aaccagaagt ttctttcttg    480

aacatcggta ttcctggccc tgtatttatc cgtgcaggtt cttggatcgg tggtcaattg    540

gttcctcgtt ctgtatcttt ggaactgggc gaaacttacg agtttaaagt actgttgaaa    600

gcacgtcgcc caggcgactg gcacgttcac accatgatga acgttcaagg cggtggtcct    660

atcattggac caggtaaatg ggtaaccatt actggtaaaa tgagcgattt cgttaaccca    720

gttactactc tgactggcca aacgatcgac ctcgaagact acgcgctgga caacgtttac    780

ttctggcacg cagtatggtt tgcaattggc tttgcttggt tgattttctg gatcaaacgt    840

ccaatctttg ttccacgtca catcgctgtt agcactggta aagcagactc tctgatctct    900

gctggcgaca aaaaagtagc catgatcttc ggtgttggta ctctggttat cgttgctgct    960

tctatgggcg caaccaacga aaaataccca gtaaccactc ctctgcaagc tggtttgttg   1020

cgtggtatga agccttatca aatgccagaa tctactgttt ctgttaaagt tgatgacgct   1080

acctaccgtg taccaggtcg tgctatgcaa atgactctga ccatcaccaa caatggtgac   1140

tcagctgttc gtttgggtga gttcaacact gctggcgttc gtttcctgga ctcttctgtt   1200

catgaagatg aaaccggtta tccagatgac ttgttggctg aagatggttt gtctgttagc   1260

gacaacagcc cgattgctcc aggtgagact cgtactgttg aagttacagc ttctgacgct   1320

gcttgggaag tatatcgtct ggctgacttg atctatgacc cagacagccg cttcgcaggt   1380

ctgatgttct tctgggacga aaacggcaac cgtcaaatga ctatggttga cgctcctctg   1440

atcccaactt tcatc                                                    1455
```

<210> SEQ ID NO 80
<211> LENGTH: 485
<212> TYPE: PRT
<213> ORGANISM: METHYLOMONAS SP.

<400> SEQUENCE: 80

-continued

```
Arg Arg Cys Ser Cys Ile Ser Val Leu Leu Arg Leu Arg Phe Tyr His
  1               5                  10                  15

His Leu Leu Leu Val Ala Leu Leu Arg Pro Leu Val Leu Lys Asn Arg
             20                  25                  30

Leu His Arg Arg Arg Cys Phe Leu Ile Glu Asp Leu Arg Lys Met Thr
         35                  40                  45

Ala Gly Met Thr Cys Ser Arg Leu Pro Glu Asp Leu Asn Tyr Lys Phe
     50                  55                  60

Ser Ser Asn Arg Gly Gly Asn Met Lys Ile Ile Lys Asp Arg Val Ala
 65                  70                  75                  80

Lys Leu Ser Phe Val Ala Leu Leu Ile Thr Met Thr Ala Ala Met Phe
                 85                  90                  95

Tyr Ala Pro Thr Ala Ser Ala His Gly Glu Lys Ser Gln Ala Ala Phe
            100                 105                 110

Met Arg Met Arg Thr Ile His Trp Phe Asp Leu Asn Trp Ser Ala Asp
        115                 120                 125

Glu Val Ala Val Asn Asp Thr Met Thr Ile Ser Gly Lys Phe His Val
    130                 135                 140

Phe Ala Gly Trp Pro Glu Thr Val Asp Lys Pro Glu Val Ser Phe Leu
145                 150                 155                 160

Asn Ile Gly Ile Pro Gly Pro Val Phe Ile Arg Ala Gly Ser Trp Ile
                165                 170                 175

Gly Gly Gln Leu Val Pro Arg Ser Val Ser Leu Glu Leu Gly Glu Thr
            180                 185                 190

Tyr Glu Phe Lys Val Leu Leu Lys Ala Arg Arg Pro Gly Asp Trp His
        195                 200                 205

Val His Thr Met Met Asn Val Gln Gly Gly Gly Pro Ile Ile Gly Pro
    210                 215                 220

Gly Lys Trp Val Thr Ile Thr Gly Lys Met Ser Asp Phe Val Asn Pro
225                 230                 235                 240

Val Thr Thr Leu Thr Gly Gln Thr Ile Asp Leu Glu Asp Tyr Ala Leu
                245                 250                 255

Asp Asn Val Tyr Phe Trp His Ala Val Trp Phe Ala Ile Gly Phe Ala
            260                 265                 270

Trp Leu Ile Phe Trp Ile Lys Arg Pro Ile Phe Val Pro Arg His Ile
        275                 280                 285

Ala Val Ser Thr Gly Lys Ala Asp Ser Leu Ile Ser Ala Gly Asp Lys
    290                 295                 300

Lys Val Ala Met Ile Phe Gly Val Gly Thr Leu Val Ile Val Ala Ala
305                 310                 315                 320

Ser Met Gly Ala Thr Asn Glu Lys Tyr Pro Val Thr Thr Pro Leu Gln
                325                 330                 335

Ala Gly Leu Leu Arg Gly Met Lys Pro Tyr Gln Met Pro Glu Ser Thr
            340                 345                 350

Val Ser Val Lys Val Asp Asp Ala Thr Tyr Arg Val Pro Gly Arg Ala
        355                 360                 365

Met Gln Met Thr Leu Thr Ile Thr Asn Asn Gly Asp Ser Ala Val Arg
    370                 375                 380

Leu Gly Glu Phe Asn Thr Ala Gly Val Arg Phe Leu Asp Ser Ser Val
385                 390                 395                 400

His Glu Asp Glu Thr Gly Tyr Pro Asp Asp Leu Leu Ala Glu Asp Gly
                405                 410                 415

Leu Ser Val Ser Asp Asn Ser Pro Ile Ala Pro Gly Glu Thr Arg Thr
```

-continued

```
            420                 425                 430

Val Glu Val Thr Ala Ser Asp Ala Ala Trp Glu Val Tyr Arg Leu Ala
        435                 440                 445

Asp Leu Ile Tyr Asp Pro Asp Ser Arg Phe Ala Gly Leu Met Phe Phe
    450                 455                 460

Trp Asp Glu Asn Gly Asn Arg Gln Met Thr Met Val Asp Ala Pro Leu
465                 470                 475                 480

Ile Pro Thr Phe Ile
                485


<210> SEQ ID NO 81
<211> LENGTH: 1429
<212> TYPE: DNA
<213> ORGANISM: METHYLOMONAS SP.

<400> SEQUENCE: 81

cggtatgctt aacacatgca agtcgaacgc tgaagggtgc ttgcacctgg atgagtggcg      60

gacgggtgag taatgcatag gaatctgcct attagtgggg gataacgtgg ggaaactcac     120

gctaataccg catacgctct acggaggaaa gccggggacc ttcgggcctg gcgctaatag     180

atgagcctat gtcggattag ctagttggtg gggtaaaggc ctaccaaggc gacgatccgt     240

agctggtctg agaggatgat cagccacact gggactgaga cacggcccag actcctacgg     300

gaggcagcag tggggaatat tggacaatgg gcgcaagcct gatccagcaa taccgcgtgt     360

gtgaagaagg cctgagggtt gtaaagcact ttcaatggga aggaacacct atcggttaat     420

acccggtaga ctgacattac ccatacaaga agcaccggct aactccgtgc cagcagccgc     480

ggtaatacgg agggtgcaag cgttaatcgg aattactggg cgtaaagcgt gcgtaggcgg     540

ttttttaagt cagatgtgaa agccctgggc ttaacctggg aactgcattt gatactgggg     600

aactagagtt gagtagagga gagtggaatt tcaggtgtag cggtgaaatg cgtagagatc     660

tgaaggaaca ccagtggcga aggcggctct ctggactcaa actgacgctg aggtacgaaa     720

gcgtgggtag caaacaggat tagataccct ggtagtccac gccgtaaacg atgtcaacta     780

accgttgggt tcttaaagaa cttagtggtg gagctaacgt attaagttga ccgcctgggg     840

agtacggccg caaggctaaa actcaaatga attgacgggg gcccgcacaa gcggtggagc     900

atgtggttta attcgatgca acgcgaagaa ccttacctac ccttgacatc ctcggaactt     960

gtcagagatg acttggtgcc ttcgggaacc gagagacagg tgctgcatgg ctgtcgtcag    1020

ctcgtgtcgt gagatgttgg gttaagtccc gtaacgagcg caacccttat ccttagttgc    1080

cagcgcgtca tggcgggaac tctagggaga ctgccggtga taaaccggag gaaggtgggg    1140

acgacgtcaa gtcatcatgg cccttatggg tagggctaca cacgtgctac aatggtcggt    1200

acagagggtt gcgaactcgc gagagccagc caatcccaaa aagccgatcc tagtccggat    1260

tgcagtctgc aactcgactt gcatgaagtc ggaatcgcta gtaatcgcgg atcagaatgc    1320

cgcggtgaat acgttcccgg gccttgtaca caccgcccgt cacaccatgg gagtgggttg    1380

caaaagaagt aggtagttta accttcggga gggcgcttac cactttgtg                1429
```